(12) United States Patent
Yadidi

(10) Patent No.: US 11,077,058 B2
(45) Date of Patent: *Aug. 3, 2021

(54) DRY POWDER COMPOSITIONS WITH MAGNESIUM STEARATE

(71) Applicant: OTITOPIC INC., Los Angeles, CA (US)

(72) Inventor: Kambiz Yadidi, Los Angeles, CA (US)

(73) Assignee: OTITOPIC INC., Beverly Hills, CA (US)

(*) Notice: Subject to any disclaimer, the term of this patent is extended or adjusted under 35 U.S.C. 154(b) by 177 days.

This patent is subject to a terminal disclaimer.

(21) Appl. No.: 16/266,042

(22) Filed: Feb. 2, 2019

(65) Prior Publication Data

US 2019/0336448 A1 Nov. 7, 2019

Related U.S. Application Data

(63) Continuation of application No. 15/716,492, filed on Sep. 26, 2017, now Pat. No. 10,195,147.

(60) Provisional application No. 62/562,295, filed on Sep. 22, 2017.

(51) Int. Cl.

| *A61K 9/14* | (2006.01) |
| *A61K 9/00* | (2006.01) |
| *A61K 31/616* | (2006.01) |
| *A61K 31/4365* | (2006.01) |
| *A61M 15/00* | (2006.01) |
| *A61M 16/14* | (2006.01) |
| *A61M 11/00* | (2006.01) |

(52) U.S. Cl.
CPC ............ *A61K 9/145* (2013.01); *A61K 9/008* (2013.01); *A61K 9/0075* (2013.01); *A61K 31/4365* (2013.01); *A61K 31/616* (2013.01); *A61M 15/003* (2014.02); *A61M 15/0021* (2014.02); *A61M 15/0035* (2014.02); *A61M 15/0041* (2014.02); *A61M 15/0086* (2013.01); *A61M 16/14* (2013.01); *A61M 11/003* (2014.02); *A61M 15/0023* (2014.02); *A61M 2202/064* (2013.01); *A61M 2205/582* (2013.01); *A61M 2206/16* (2013.01)

(58) Field of Classification Search
None
See application file for complete search history.

(56) References Cited

U.S. PATENT DOCUMENTS

| 4,069,819 A | 1/1978 | Valentini et al. |
| 4,849,417 A | 7/1989 | Bertrand et al. |
| 4,995,385 A | 2/1991 | Valentini et al. |
| 5,006,516 A | 4/1991 | Helbig et al. |
| 5,327,883 A | 7/1994 | Williams et al. |
| 5,533,502 A | 7/1996 | Piper |
| 5,875,776 A | 3/1999 | Vaghefi |
| 6,884,794 B2 | 4/2005 | Staniforth et al. |
| 6,979,437 B2 | 12/2005 | Bartus et al. |
| 6,994,842 B2 | 2/2006 | Lee et al. |
| 7,025,059 B2 | 4/2006 | Pera |
| 7,041,286 B2 | 5/2006 | Nerenberg |
| 7,089,934 B2 | 8/2006 | Staniforth et al. |
| 7,189,750 B2 | 3/2007 | Assaf et al. |
| 7,405,207 B2 | 7/2008 | Leonard et al. |
| 7,431,916 B2 | 10/2008 | Nilsson et al. |
| 7,435,720 B2 | 10/2008 | Quay et al. |
| 7,516,741 B2 | 4/2009 | Glusker et al. |
| 7,534,914 B2 | 5/2009 | Koike et al. |
| 7,559,325 B2 | 7/2009 | Dunkley et al. |
| 7,651,770 B2 | 1/2010 | Berkland et al. |
| 7,682,614 B2 | 3/2010 | Strober et al. |
| 7,744,906 B2 | 6/2010 | Coates |
| 8,069,851 B2 | 12/2011 | Dunkley et al. |
| 8,236,786 B2 | 8/2012 | Finch et al. |
| 8,530,463 B2 | 9/2013 | Cartt et al. |
| 8,561,609 B2 | 10/2013 | Donovan et al. |
| 8,614,255 B2 | 12/2013 | Blizzard et al. |
| 8,623,419 B2 | 1/2014 | Malakhov et al. |
| 8,771,744 B2 | 7/2014 | Ruecroft et al. |
| 8,790,648 B2 | 7/2014 | Tocker et al. |
| 8,795,634 B2 | 8/2014 | Illum et al. |
| 8,940,683 B2 | 1/2015 | Levitt |
| 8,985,102 B2 | 3/2015 | Hodson et al. |
| 8,997,799 B2 | 4/2015 | Hodson et al. |

(Continued)

FOREIGN PATENT DOCUMENTS

| CA | 1246597 | 12/1988 |
| CN | 102058886 | 5/2011 |

(Continued)

OTHER PUBLICATIONS

Clark et., "The Relationship Between Power Inhaler Resistance and Peak Inspiration Conditions in Healthy Volunteers—Inplications for In Vitro Testing", Journal of Aerosol Med, 1993, 6(2), p. 99-110.
Dalby et al., "Inhalation Aerosols Physical and Biological Basis for Therapy", edited by Hickey, Informa Healthcare USA, 2007, p. 437.
Dehaan et al., "Predicting extrathoracic deposition from dry powder inhalers", Journal of Aerosol Science, 2003, 35 (3), p. 309-331.

(Continued)

*Primary Examiner* — Robert A Wax
*Assistant Examiner* — Randeep Singh
(74) *Attorney, Agent, or Firm* — FisherBroyles, LLP; James W. Hill

(57) ABSTRACT

A stable dry powder composition for inhalation includes acetylsalicylic acid in particles having a mass median aerodynamic diameter (MMAD) in a range of about 1 μm to about 5 μm. The dry powder composition may contain a pharmaceutically acceptable excipient, such as a stearate, in an amount ranging from about 0.04% (w/w) to about 0.06% (w/w), or from about 0.4% (w/w) to about 0.6% (w/w), of the composition.

17 Claims, 22 Drawing Sheets

(56) References Cited

U.S. PATENT DOCUMENTS

| | | |
|---|---|---|
| 9,051,302 B2 | 6/2015 | Winssinger et al. |
| 9,061,352 B2 | 6/2015 | Lipp et al. |
| 9,085,632 B2 | 7/2015 | Coates et al. |
| 9,101,539 B2 | 8/2015 | Nagata et al. |
| 9,125,999 B2 | 9/2015 | Rolfs et al. |
| 9,138,407 B2 | 9/2015 | Caponetti et al. |
| 2003/0176421 A1 | 9/2003 | Watson et al. |
| 2003/0186843 A1 | 10/2003 | Staniforth et al. |
| 2003/0232019 A1 | 12/2003 | Basu et al. |
| 2004/0049022 A1 | 3/2004 | Nyce et al. |
| 2004/0092470 A1 | 5/2004 | Leonard et al. |
| 2004/0105821 A1 | 6/2004 | Bernstein et al. |
| 2005/0004079 A1 | 1/2005 | Benjamin et al. |
| 2005/0148555 A1 | 7/2005 | Gupta et al. |
| 2005/0249697 A1 | 11/2005 | Uhrich et al. |
| 2006/0002995 A1 | 1/2006 | Harwigsson |
| 2006/0030550 A1 | 2/2006 | Lithgow et al. |
| 2006/0257987 A1 | 11/2006 | Gonzalez Valcarcel et al. |
| 2006/0293217 A1 | 12/2006 | Barker et al. |
| 2007/0072939 A1 | 3/2007 | Kupper |
| 2007/0116761 A1 | 5/2007 | Desai et al. |
| 2007/0123571 A1 | 5/2007 | Raj et al. |
| 2007/0178166 A1 | 8/2007 | Bernstein et al. |
| 2007/0232575 A1 | 10/2007 | Baulieu et al. |
| 2008/0066741 A1 | 3/2008 | Lemahieu et al. |
| 2008/0127972 A1 | 6/2008 | Morton |
| 2008/0220078 A1 | 9/2008 | Morton et al. |
| 2009/0011030 A1 | 1/2009 | Jouhikainen et al. |
| 2009/0110679 A1 | 4/2009 | Li et al. |
| 2009/0136561 A1 | 5/2009 | Von Rechenberg et al. |
| 2009/0220435 A1 | 9/2009 | Quay et al. |
| 2009/0312380 A1 | 12/2009 | Becker |
| 2010/0158819 A1 | 6/2010 | Kligerman et al. |
| 2010/0168710 A1 | 7/2010 | Braithwaite |
| 2010/0234442 A1 | 9/2010 | Duarte-Vazquez et al. |
| 2010/0258118 A1 | 10/2010 | Morton |
| 2010/0319694 A1 | 12/2010 | Cook et al. |
| 2011/0038931 A1 | 2/2011 | Kim et al. |
| 2011/0112134 A1 | 5/2011 | Hutchinson et al. |
| 2011/0142914 A1 | 6/2011 | Persaud et al. |
| 2011/0146678 A1 | 6/2011 | Ruecroft et al. |
| 2011/0166133 A1 | 7/2011 | Albaugh et al. |
| 2011/0189106 A1 | 8/2011 | Danzig et al. |
| 2011/0200657 A1 | 8/2011 | Baker |
| 2011/0250130 A1 | 10/2011 | Benatuil et al. |
| 2011/0263610 A1 | 10/2011 | Wan et al. |
| 2012/0017892 A1 | 1/2012 | Ludwig |
| 2012/0046251 A1 | 2/2012 | Schaefer et al. |
| 2012/0125325 A1 | 5/2012 | Bannister et al. |
| 2012/0263680 A1 | 10/2012 | Lander et al. |
| 2012/0276193 A1 | 11/2012 | Graversen et al. |
| 2012/0306613 A1 | 12/2012 | Staniforth et al. |
| 2012/0308566 A1 | 12/2012 | Martin et al. |
| 2012/0308613 A1 | 12/2012 | Staniforth et al. |
| 2012/0309809 A1 | 12/2012 | Green et al. |
| 2013/0004969 A1 | 1/2013 | Peschon et al. |
| 2013/0028942 A1 | 1/2013 | Surber et al. |
| 2013/0316001 A1 | 11/2013 | Popov et al. |
| 2014/0065219 A1 | 3/2014 | Bosch et al. |
| 2014/0079784 A1 | 3/2014 | Burnier et al. |
| 2014/0174437 A1 | 6/2014 | Yadidi |
| 2014/0213560 A1 | 7/2014 | Vakkalanka |
| 2014/0234330 A1 | 8/2014 | Budelsky et al. |
| 2014/0239525 A1 | 8/2014 | Mcconville et al. |
| 2014/0242174 A1 | 8/2014 | Walker |
| 2014/0322238 A1 | 10/2014 | Budelsky et al. |
| 2014/0322328 A1 | 10/2014 | Yadidi |
| 2014/0364837 A1 | 12/2014 | Boyes et al. |
| 2015/0005230 A1 | 1/2015 | Eliasof |
| 2015/0045332 A1 | 2/2015 | Swenson |
| 2015/0050713 A1 | 2/2015 | Malakhov et al. |
| 2015/0059746 A1 | 3/2015 | Green |
| 2015/0093338 A1 | 4/2015 | Farber |
| 2015/0132386 A1 | 5/2015 | Heng et al. |
| 2015/0136130 A1 | 5/2015 | Dehaan et al. |
| 2015/0224129 A1 | 8/2015 | Trottein et al. |
| 2015/0239866 A1 | 8/2015 | Machacek et al. |
| 2015/0239966 A1 | 8/2015 | Baciu et al. |
| 2015/0239987 A1 | 8/2015 | Liang et al. |
| 2015/0284381 A1 | 10/2015 | Andresen et al. |
| 2015/0320694 A1 | 11/2015 | Gu et al. |
| 2015/0322070 A1 | 11/2015 | Rao et al. |

FOREIGN PATENT DOCUMENTS

| | | |
|---|---|---|
| CN | 105833399 | 8/2016 |
| EP | 200628 | 7/1988 |
| EP | 1177805 | 2/2002 |
| WO | 2000027359 | 5/2000 |
| WO | 2003047598 | 6/2003 |
| WO | 2003047628 | 6/2003 |
| WO | 2005040163 | 5/2005 |
| WO | 2005041886 | 5/2005 |
| WO | 2006017354 | 2/2006 |
| WO | 2007072503 | 6/2007 |
| WO | 2009019598 | 2/2009 |
| WO | 2012107364 | 8/2012 |
| WO | 2012107765 | 8/2012 |
| WO | 2013004999 | 1/2013 |
| WO | 2014131851 | 9/2014 |
| WO | 2014155103 | 10/2014 |
| WO | 2015002703 | 1/2015 |
| WO | 2015011244 | 1/2015 |
| WO | 2015054574 | 4/2015 |
| WO | 2015096668 | 7/2015 |
| WO | 2015127315 | 8/2015 |
| WO | 2015148415 | 10/2015 |
| WO | 2015153838 | 10/2015 |
| WO | 2015155544 | 10/2015 |
| WO | 2016019253 | 2/2016 |

OTHER PUBLICATIONS

Geller, M.D., et al., "Development of an inhaled drypowder formulation of tobramycin using pulmosphere™ technology", J Aerosol Med Pulm Drug Deliv. Aug. 2011; 24(4), p. 175-82.

Gonda, I. "Aerosols for delivery of therapeutic and diagnostic agents to the respiratory tract", in Critical Reviews in Therapeutic Drug Carrier Systems, 1990, 6: 273-313.

Hadinoto et al., "Drug Release Study of Large Hollow Nanoparticulate Aggregates Carrier Particles for Pulmonary Delivery", International Journal of Pharmaceutics, 2007, 341(1-2), p. 195-206.

Kupczyk, et al. "Lipoxin A4 Generation is Decreased in Aspirin-Sensitive Patients in Lysine-Aspirin Nasal Challenge in Vivo Model", Allergy (Oxford, United Kingdom), 2009, 64(12), p. 1746-1752.

Moren et al., "Aerosol Dosage Forms and Formulations", Aerosols in Medicine, Principles, Diagnosis and Therapy, 1985, pp. 261-287, Esevier Science Publishers B.V., Amsterdam.

Stank et al., "Physico-chemical characterization of surface modified particles for inhalation", International Journal of Pharmaceutics, 2013, 448:9-18.

Tiddens et al., "Effect of Dry Powder Inhaler Resistance on the Inspiratory Flow Rates and Volumes of Cystic Fibrosis Patients of Six Years and Older", Journal of Aerosol Med, 2006, 19, (4), p. 456-465.

United States Patent and Trademark Office, International Search Report and Written Opinion for International Application No. PCT/US2017/053569, dated Nov. 27, 2017, 9 pages.

USP Bulk Density and Tapped Density, United States Pharmacopia convention, Rockville, MD, 10th Supplement, 1999, p. 4950-4951.

USP Section 30 601 Aerosols, Metered-Dose Inhalers and Dry Powder Inhalers, Delivered-Dose Uniformity, Sampling the Delivered Dose from Dry Powder Inhalers, United States Pharmacopeia Convention, 2007, 13th Revision, p. 222-225, Rockville, MD.

Connors et al., "Chemical Stability of Pharmaceuticals", A Handbook for Pharmacists, Oct. 1986, 864 pages, 2nd Edition.

Bharate et al., "Interactions and incompatibilities of pharmaceutical excipients with active pharmaceutical Ingredients: a comprehensive review," J. Excipients and Food Chem., Nov. 3, 2010, pp. 3-26, 1(3).

(56) References Cited

OTHER PUBLICATIONS

Li et al., "Lubricants in Pharmaceutical Solid Dosage Forms", Lubricants, Feb. 25, 2014, pp. 21-43, 2.
Swaminathan et al., "Effect of Magnesium Stearate on the Content Uniformity of Active Ingredient in Pharmaceutical Powder Mixtures", AAPS PharmSciTech 2002, pp. 1-5, 3(3), Article 19, https://www.ncbi.nlm.nih.gov/pmc/articles/PMC2784048/pdf/12249_2008_Article_BF02830617.pdf.

DRY POWDER COMPOSITIONS WITH MAGNESIUM STEARATE

CROSS REFERENCE TO RELATED APPLICATIONS

This application is a continuation of U.S. patent application Ser. No. 15/716,492, filed Sep. 26, 2017, now U.S. Pat. No. 10,195,147, issued Feb. 5, 2019, which claims the benefit of U.S. Provisional Patent Application No. 62/562,295, filed Sep. 22, 2017, the disclosures of which are incorporated by reference in their entirety.

FIELD

The subject technology relates generally to dry powder compositions comprising magnesium stearate (MgST) and an active pharmaceutical ingredient (API) such as a non-steroidal anti-inflammatory drug (NSAID) (e.g., aspirin or acetylsalicylic acid (ASA)), and preparation methods thereof. The subject technology also relates generally to apparatuses and methods for delivery of API to the lungs by inhalation for treating disease, such as ischemic or thromboembolic events, including cardiovascular disease.

BACKGROUND

Pulmonary delivery of therapeutic agents offers several advantages over other modes of delivery. These advantages include rapid onset of action, convenience of patient self-administration, potential for reduced drug side effects, ease of delivery by inhalation, and the elimination of needle. Inhalation therapy is capable of providing a drug delivery system that is easy to use in an inpatient or outpatient setting, results in very rapid onset of drug action, and produces minimal side effects.

MgST is a common excipient used in pharmaceutical formulations. However, MgST is known to catalyze acid-based hydrolysis. Thus, MgST is not compatible with active ingredients susceptible to acid-based hydrolysis, e.g., ASA. Unexpectedly, ASA/MgST formulations disclosed herein showed high ASA stability under various conditions for months. Similar compositions of MgST with other API previously known to be incompatible may also possess unexpected high API stability in the presence of MgST.

SUMMARY

In certain embodiments of the invention, stable dry powder compositions comprising an active pharmaceutical ingredient (API) and magnesium stearate (MgST) are provided herein, with preparation methods thereof. Examples of API include, without limitations, APIs susceptible to acid-based hydrolysis, such as non-steroidal anti-inflammatory drugs (NSAID), e.g., acetylsalicylic acid (ASA).

In certain embodiments of the invention, the dry powder compositions of API (e.g., ASA) and MgST (e.g., ASA/MgST) disclosed herein have one or more characters selected from the group consisting of mass medium aerodynamic diameter (MMAD) of about 0.5 µm to about 10 µm, about 0.5 µm to about 3 µm, about 2 µm to about 3 µm, or about 3 µm or lower, a fine particle fraction (FPF) % of about 40% to about 90%, from about 40% to about 80%, from about 40% to about 70%, from about 40% to about 60%, from about 40% to about 50%, from about 30% to about 40%, from about 20% to about 30%, from about 30% to about 50%, or from about 30% to about 60%, geometric standard deviation (GSD) of about 2.5 µm or lower, about 2 µm to about 2.5 µm, or about 1.7 µm to about 2 µm, and an emitted dose (ED) of about 55% to about 85%, about 58% to about 85%, about 60% to about 65%, about 70% to about 85%, about 75% or higher, or about 90% or higher.

In certain embodiments of the invention, a method for treating a disease, e.g., by reducing the risk of a thromboembolic event, comprises administering the dry powder composition of NSAID/MgST (e.g., ASA/MgST) disclosed herein. In certain embodiments, the dry powder composition of NSAID/MgST (e.g., ASA/MgST) disclosed herein is administered via a dry powder inhaler (DPI) or a metered dose inhaler (MDI).

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIG. 1A: HPLC chromatograms of co-micronized ASA compositions with 10% w/w of MgST prepared according to Example 1 and stored at a condition of 15-20° C./35-45% RH for 12 months.

FIG. 1B: HPLC chromatograms of co-micronized ASA compositions with 5% w/w of MgST prepared according to Example 1 and stored at a condition of 15-20° C./35-45% RH for 12 months.

FIG. 1C: HPLC chromatograms of co-micronized ASA compositions with 1% w/w of MgST prepared according to Example 1 and stored at a condition of 15-20° C./35-45% RH for 12 months.

FIG. 1D: HPLC chromatograms of co-micronized ASA compositions with 0.5% w/w of MgST prepared according to Example 1 and stored at a condition of 15-20° C./35-45% RH for 12 months.

FIG. 1E: HPLC chromatograms of co-micronized ASA compositions with 0.25% w/w of MgST prepared according to Example 1 and stored at a condition of 15-20° C./35-45% RH for 12 months.

FIG. 1F: HPLC chromatograms of co-micronized ASA compositions with 0.1% w/w of MgST prepared according to Example 1 and stored at a condition of 15-20° C./35-45% RH for 12 months.

FIG. 1G: HPLC chromatograms of co-micronized ASA compositions with 0.05% w/w of MgST prepared according to Example 1 and stored at a condition of 15-20° C./35-45% RH for 12 months.

FIG. 1H: HPLC chromatograms of co-micronized ASA compositions with 0.01% w/w of MgST prepared according to Example 1 and stored at a condition of 15-20° C./35-45% RH for 12 months.

FIG. 2A: Aerodynamic particle size distribution stability profile of ASA/MgST 0.5% w/w formulation at 50° C./75% RH.

FIG. 2B: Aerodynamic particle size distribution stability profile of ASA/MgST 0.05% w/w formulation at 50° C./75% RH.

FIG. 2C: Aerodynamic particle size distribution stability profile of ASA/MgST 0.01% w/w formulation at 50° C./75% RH.

FIG. 2D: Aerodynamic particle size distribution stability profile of ASA/MgST 0.1% w/w Formulation at 50° C./75% RH.

FIG. 4A: APSD performance of co-micronized ASA with different concentrations (0.01-0.25% w/w) of MgST (Co-M).

FIG. 4B: APSD performance of co-micronized ASA with different concentrations (0.5-10.0% w/w) of MgST (Co-M).

FIG. 4C: APSD performance of co-micronized ASA with different concentrations (0.01-0.25% w/w) of MgST (Co-M).

FIG. 4D: APSD performance of co-micronized ASA with different concentrations (0.5-10.0% w/w) of MgST (Co-M).

DETAILED DESCRIPTION

Figure 1A:
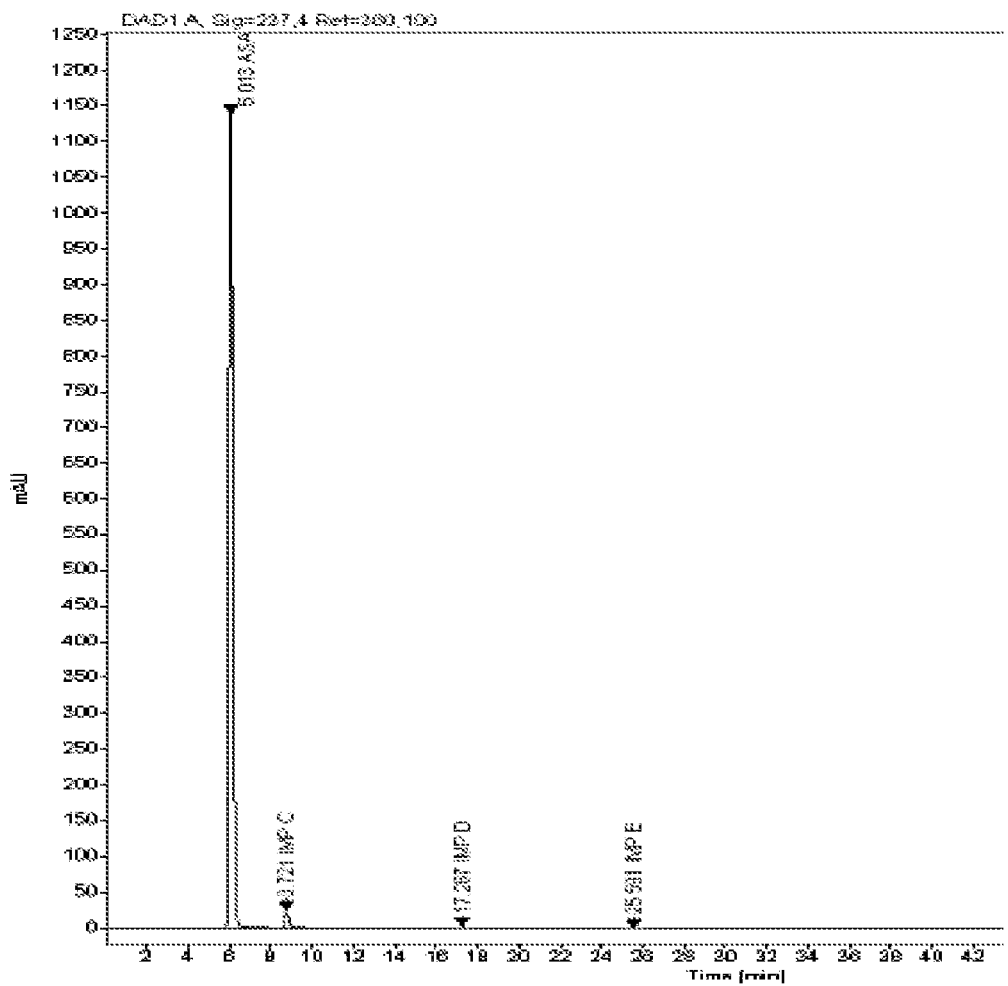
FIGS. 1A-1H: HPLC chromatograms of examples of co-micronized ASA compositions with various concentration of MgST prepared according to Example 1 and stored at a condition of 15-20° C./35-45% RH for 12 months.
Figure 1B:
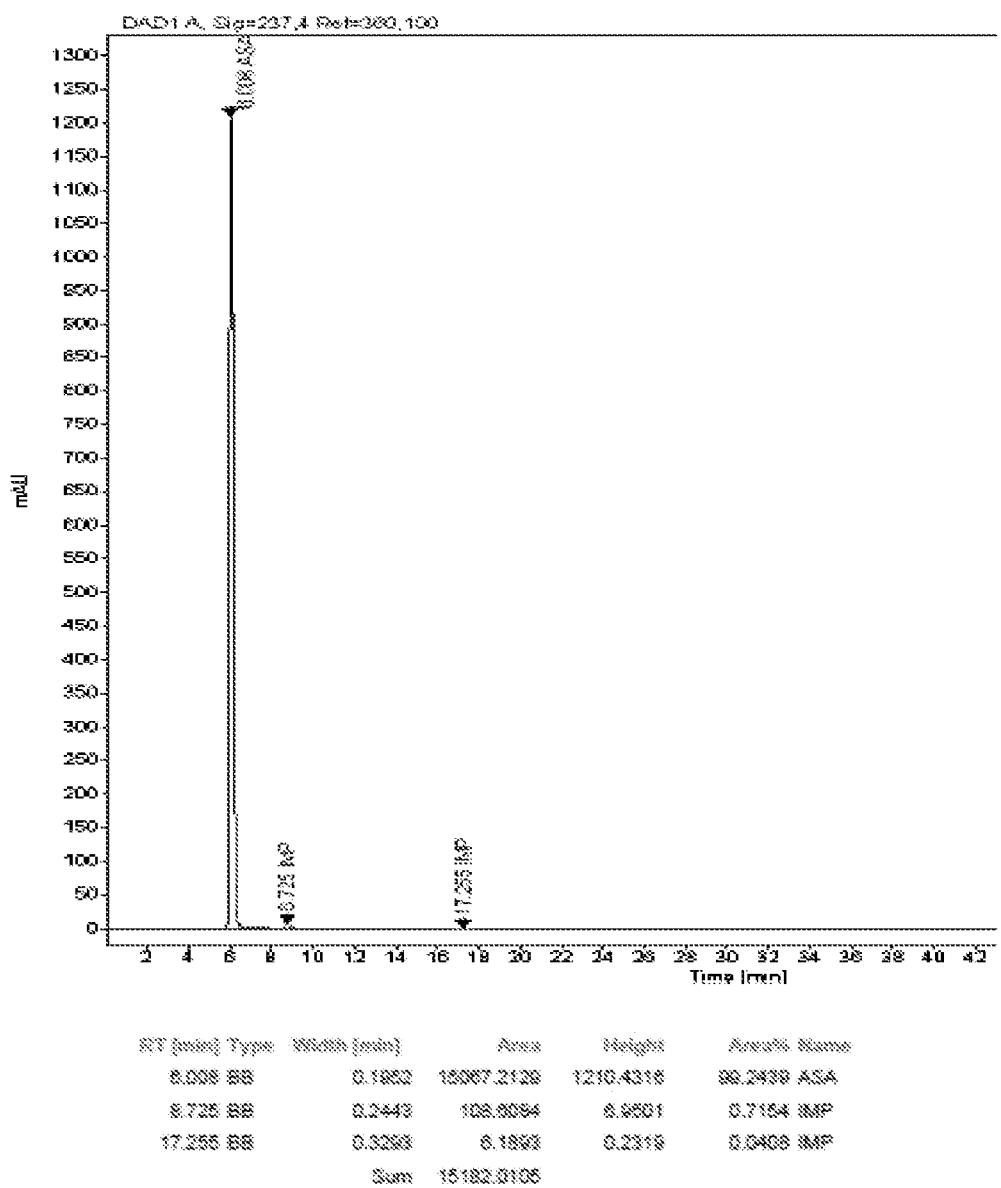
Figure 1C:
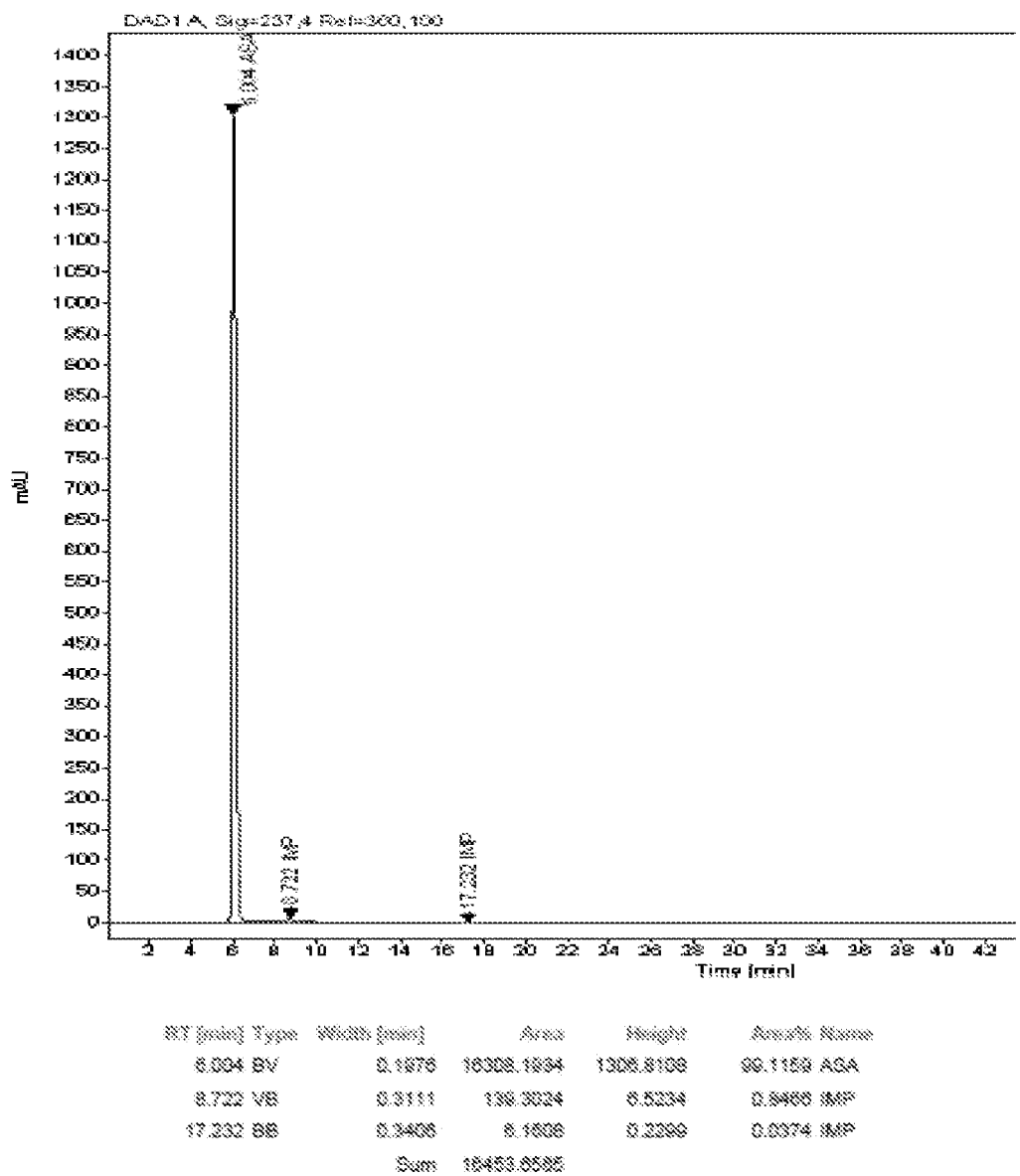
Figure 1D:
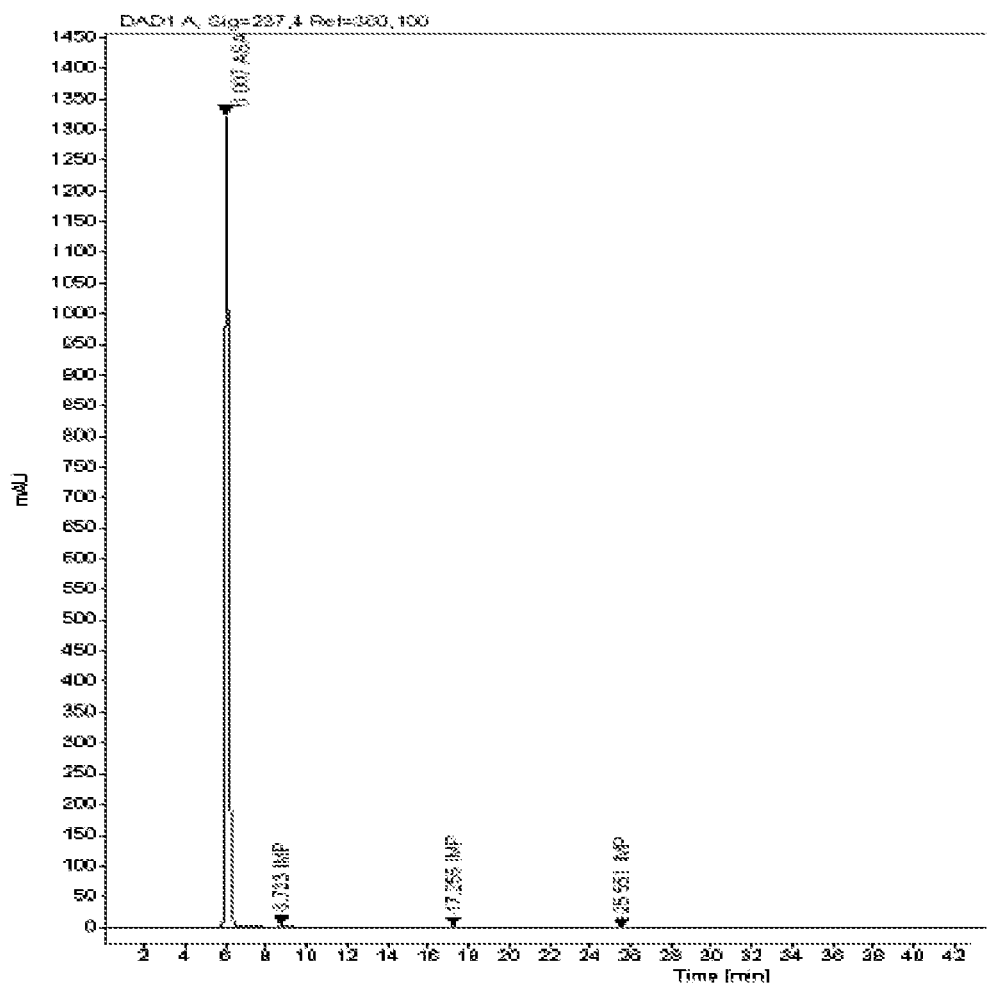
Figure 1E:
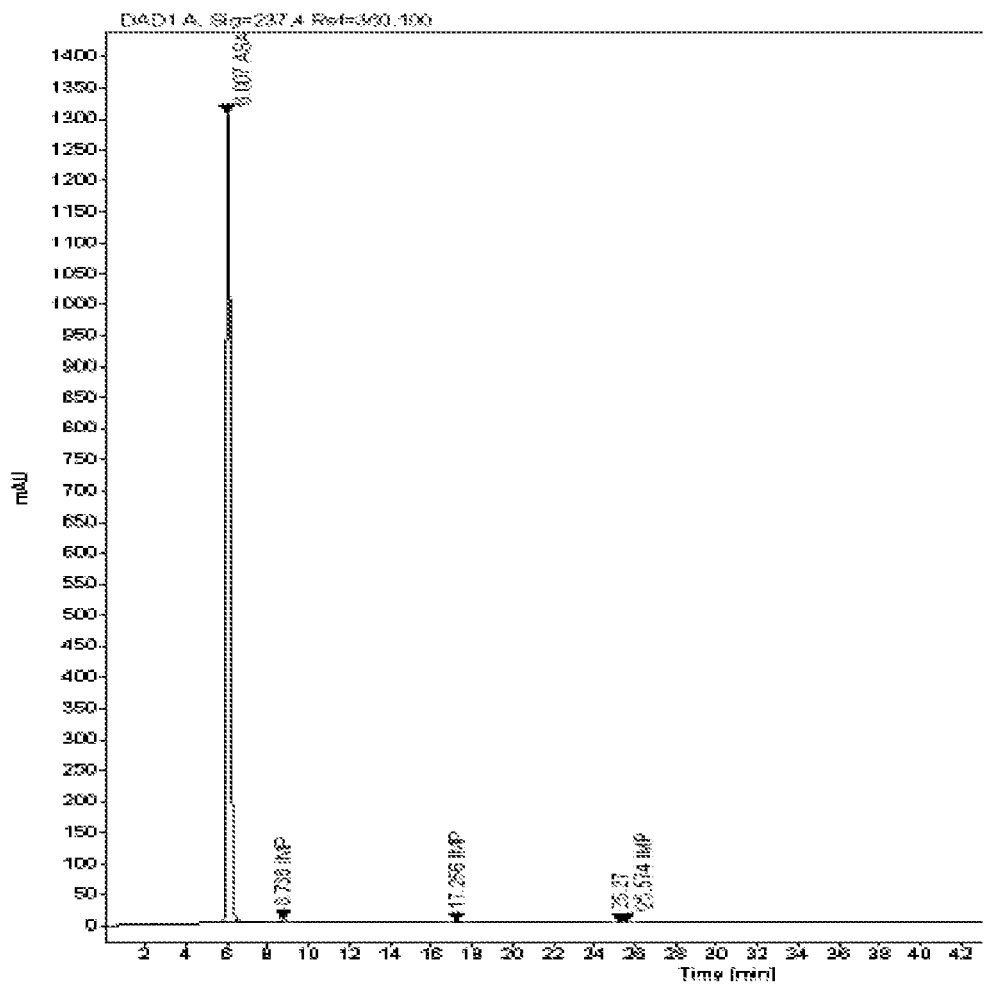
Figure 1F:
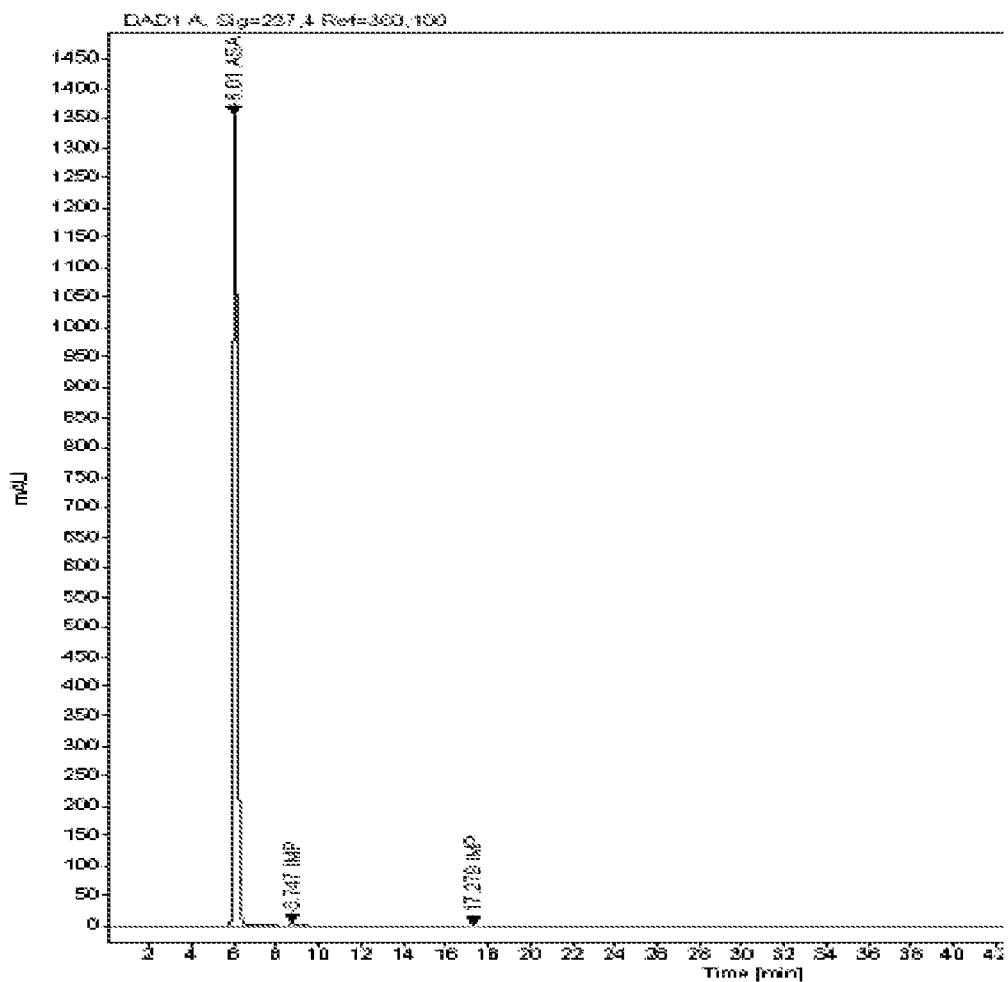
Figure 1G:
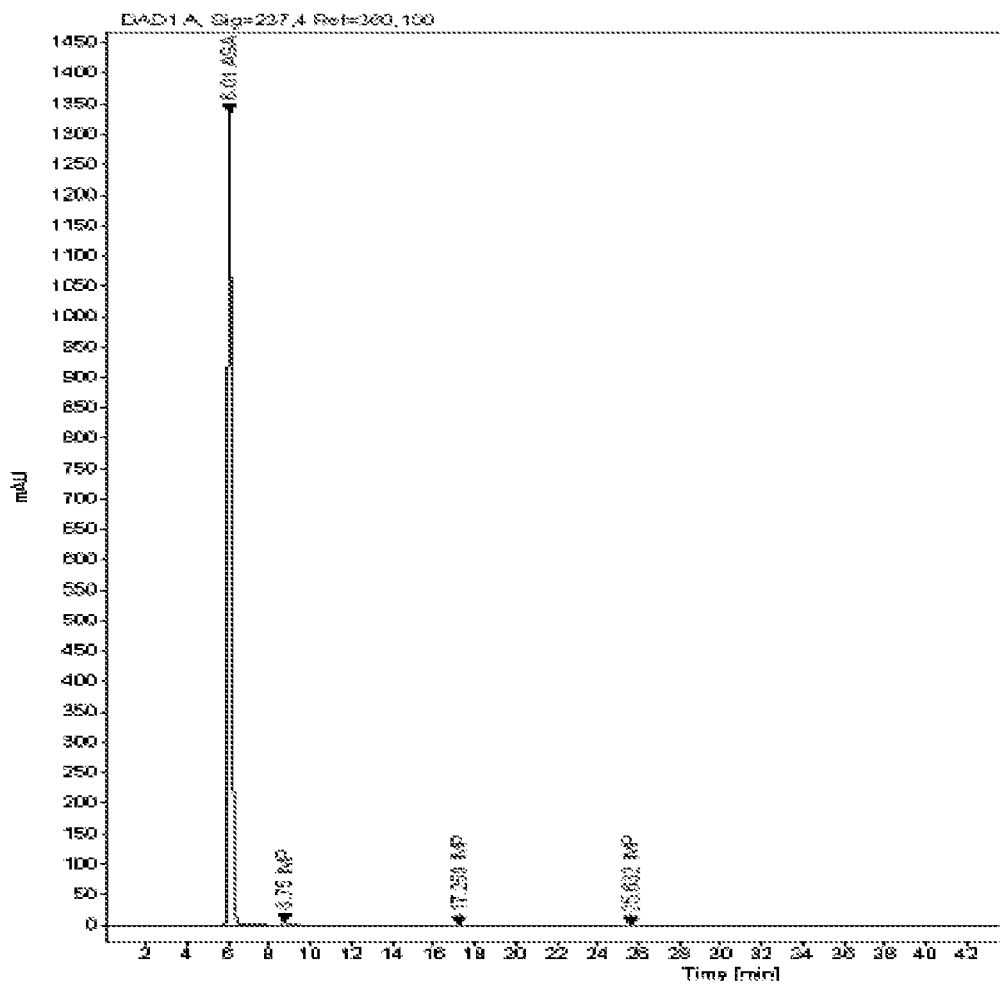
Figure 1H:
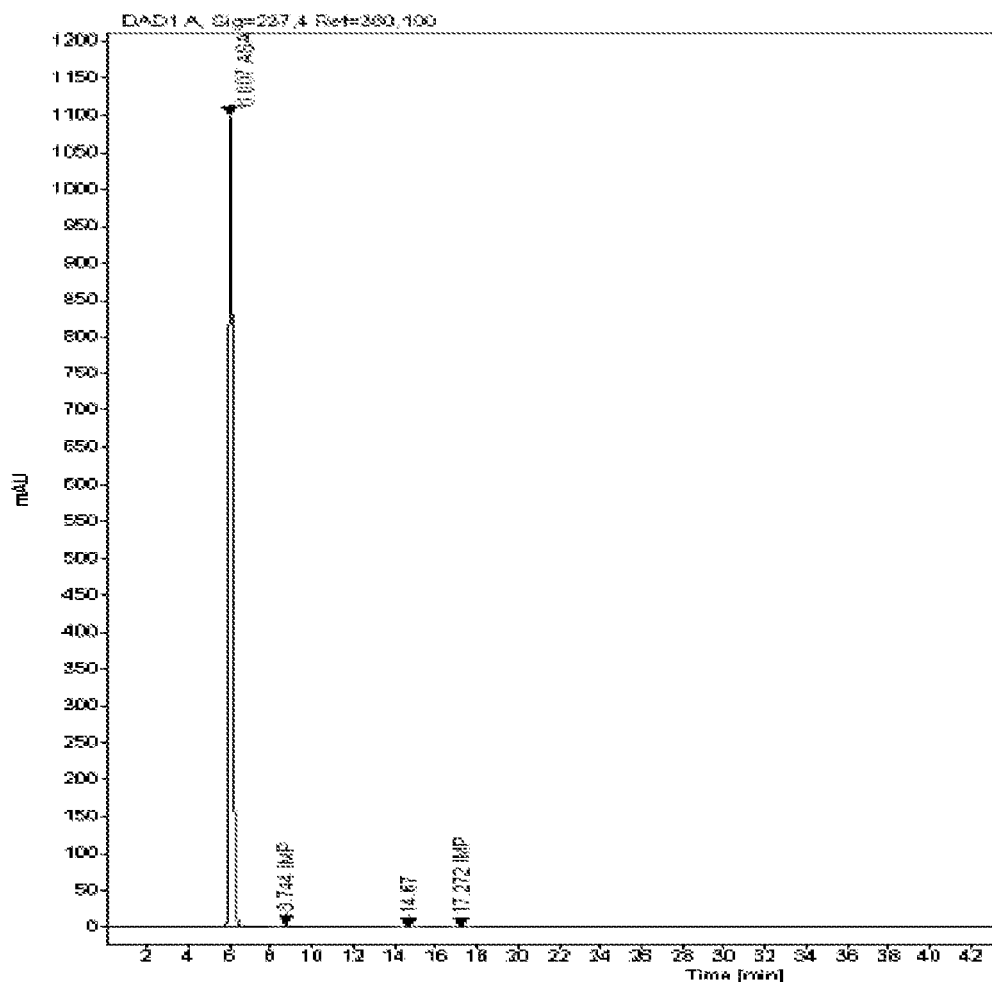

Magnesium stearate (MgST) is known to be an incompatible excipient for drugs that are susceptible to acid-based degradation (e.g., hydrolysis). Examples of drugs incompatible with MgST include, without limitation, NSAIDs (e.g., ASA, ibuproxam, indomethacin, ketoprofen), antiviral drug (e.g., acyclovir), antidiabetic drugs (e.g., glipizide, chlorpropamide, glimepiride and glibenclamide), antihypertensive drugs (e.g., captopril, fosinopril, moexipril, oxprenolol and quinapril), antibiotic drugs (e.g., cephalexin, erythromycin, nalidixic acid, oxacillin, and penicillin G), antimalarial drug (e.g., primaquine), antiemetic drug (e.g., promethazine), antiamoebic drug (e.g., albendazole), anticancer drug (e.g., β-lapachone), anticoagulant (e.g., clopidogrel), antihistaminic drug (e.g., doxylamine), and hypnotic drug (e.g., temazepam) (Bharate et al., "Interactions and incompatibilities of pharmaceutical excipients with active pharmaceutical ingredients: a comprehensive review," J. Excipients and Food Chem., 2010, 1 (3), pp. 3-26, which is incorporated herein by reference in its entirety).

Unexpectedly, dry powder compositions comprising ASA and MgST disclosed herein showed unexpectedly high stability of ASA after storage under various conditions (e.g., 15-20° C./35-45% RH, 20° C./40% RH, 30° C./60% RH, and 40° C./75% RH) for months (Examples 2-3). In certain embodiments, dry powder compositions comprising ASA and MgST disclosed herein showed unexpectedly high stability (e.g., particle stability) after storage under 40° C./75% RH for up to 30 days.

Accordingly, provided herein are stable dry powder compositions comprising an active pharmaceutical ingredient (API) and a stearate (e.g., MgST and calcium stearate). Examples of API include, without limitations, NSAIDs (e.g., ASA, ibuproxam, indomethacin, ketoprofen), antiviral drug (e.g., acyclovir), antidiabetic drugs (e.g., glipizide, chlorpropamide, glimepiride and glibenclamide), antihypertensive drugs (e.g., captopril, fosinopril, moexipril, oxprenolol and quinapril), antibiotic drugs (e.g., cephalexin, erythromycin, nalidixic acid, oxacillin, and penicillin G), antimalarial drug (e.g., primaquine), antiemetic drug (e.g., promethazine), antiamoebic drug (e.g., albendazole), anticancer drug (e.g., β-lapachone), anticoagulant (e.g., clopidogrel), antihistaminic drug (e.g., doxylamine), and hypnotic drug (e.g., temazepam).

Unless otherwise specified, as used herein, the w/w concentration of API in an API/stearate (e.g., MgST) dry powder composition is represented by the wt % of API in the total weight of API and stearate (e.g., MgST), and the w/w ratio of stearate (e.g., MgST), in an API/stearate (e.g., MgST), dry powder composition is represented by the wt % of stearate (e.g., MgST), in the total weight of API and stearate (e.g., MgST). In certain embodiments, the w/w concentration of Mg stearate (e.g., MgST), ST in the API/stearate (e.g., MgST), dry powder composition is up to about 15% w/w, up to about 10% w/w, up to about 7.5% w/w, up to about 5.0% w/w, up to about 2.5% w/w, up to about 1% w/w, up to about 0.5% w/w, up to about 0.25% w/w, up to about 0.1% w/w, up to about 0.05% w/w, up to about 0.01% w/w, from about 0.04% (w/w) to about 0.06% (w/w), or from about 0.4% (w/w) to about 0.6% (w/w).

In certain embodiments, the API of the API/MgST dry powder compositions disclosed herein (e.g., ASA/MgST) is over 99.5%, over 99%, over 98.5%, over 98%, over 97.5%, over 97%, over 96.5%, over 96%, over 95.5%, over 95%, over 90%, or over 85% stable after stored at 15-20° C./35-45% RH, 20° C./40% RH, 30° C./60% RH, 40° C./75% RH, or 50° C./75% RH, for up to 2 weeks, up to 4 weeks, up to 30 days, up to 6 weeks, up to 8 weeks, and up to 12 months. In certain embodiments, the term "stable" means the chemical stability of ASA. In certain embodiments, the term "stable" means the stability of the particle parameters, e.g., APSD and PSD characterizations disclosed herein.

In certain embodiments, the MMAD of the API/MgST dry powder compositions disclosed herein (e.g., ASA/MgST) varies less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1%, after the composition is stored at 15-20° C./35-45% RH, 20° C./40% RH, 30° C./60% RH, 40° C./75% RH, or 50° C./75% RH, for up to 2 weeks, up to 4 weeks, up to 30 days, up to 6 weeks, up to 8 weeks, and up to 12 months (e.g., MMAD, FPF, DV, GSD, ED, etc.).

In certain embodiments, the DV90, DV50 and/or DV10 of the API/MgST dry powder compositions disclosed herein (e.g., ASA/MgST) vary (varies) less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1%, after the composition is stored at 15-20° C./35-45% RH, 20° C./40% RH, 30° C./60% RH, 40° C./75% RH, or 50° C./75% RH, for up to 2 weeks, up to 4 weeks, up to 30 days, up to 6 weeks, up to 8 weeks, and up to 12 months.

Additionally, in certain embodiments containing acetylsalicylic acid. The dry particles of the dry powder may have one or more characters selected from the group consisting of:

a mass medium aerodynamic diameter (MMAD) of about 0.5 μm to about 10 μm, about 0.5 μm to about 3 μm, about 2 μm to about 3 μm, or about 3 μm or lower, a fine particle fraction (FPF) % of about 40% to about 90%, from about 40% to about 80%, from about 40% to about 70%, from about 40% to about 60%, from about 40% to about 50%, from about 30% to about 40%, from about 20% to about 30%, from about 30% to about 50%, or from about 30% to about 60%, a geometric standard deviation (GSD) of about 2.5 μm or lower, and an emitted dose (ED) of about 75% or higher.

The respirable dry powder may contain one or more other pharmaceutically acceptable excipients, such as phospholipid, fatty acids (e.g., with C10-C30 or C19-C30), and other hydrophobic excipients, in an amount ranging from about 0.1% (w/w) to about 10% (w/w) of the particles.

1A. Thromboembolic Symptoms and Events

A thromboembolic event, such as myocardial infarction, deep venous thrombosis, pulmonary embolism, thrombotic stroke, etc., can present with a group of symptoms that allow a patient or clinician to provide an initial therapy or treatment for the event, i.e., immediately, or within 1, 5, 10 or 15 minutes of onset of the thromboembolic event. In certain situations, an 81 mg, low dose, or "baby" acetylsalicylic acid or a regular acetylsalicylic acid (330 mg) may be orally administered in order to provide an initial treatment for the patient. However, oral administration may not act as quickly as necessary to provide a sufficient therapeutic effect and therefore, may lead to a less preferred outcome. Thus, the pulmonary drug delivery system and related methods or the present invention provide for an accelerated and more efficient pathway and treatment for reducing the risk of a thromboembolic event and/or providing treatment for a thromboembolic event. For example, certain embodiments provide systems and methods of administering a non-steroidal anti-inflammatory drug (NSAID) by inhalation, such as by a dry powder inhaler (DPI) or a metered dose inhaler (MDI).

1B. Dry Powder Inhaler

Delivery of a drug by inhalation in the early stages of an emergency situation can provide a fast-acting, effective form of preliminary treatment of certain medical conditions. For example, in one embodiment, upon receiving a complaint of a symptom of a serious thromboembolic event, a patient can be administered, by DPI, a therapeutic amount of a NSAID. The NSAID can address problems associated with or provide an initial treatment for the medical condition.

However, dry powder inhalation of drugs has generally been limited to dosages of less than a milligram. Recent developments in particle engineering, in particular the development of PulmoSphere® technology, have enabled the delivery of a larger amount of dry powder to the lungs in a single actuation. See David E. Geller, M. D., et al., Development of an inhaled dry-powder formulation of tobramycin using Pulmosphere™ technology, J Aerosol Med Pulm Drug Deliv. 2011 August; 24(4), pp. 175-82. In this publication, a dose of 112 mg tobramycin (in four capsules) was effectively delivered via PulmoSpheres®.

To date, there has been no single dose use of acetylsalicylic acid by dry powder inhaler to replace the traditional daily use of a NSAID (such as a baby acetylsalicylic acid) or emergency use of a NSAID as preventative care for symptoms of a thromboembolic event available on the market. Accordingly, in one embodiment, the methods provide for administering a NSAID by dry powder inhalation in an amount less than the dosage of a baby acetylsalicylic acid (e.g., less than 81 mg).

Therefore, a method for treating a condition, e.g., by reducing the risk of a thromboembolic event, comprises administering a NSAID, such as a salicylate, by a DPI or MDI. For example, the method can comprise administering acetylsalicylic acid by a DPI or MDI. The administered dose (e.g., a single dose) can be less than 25 mg of acetylsalicylic acid. Further, in various embodiments, the administered dosage (e.g., a single dose) can be less than 20 mg of acetylsalicylic acid. The administered dosage (e.g., a single dose) can be less than 80 mg, less than 70 mg, less than 60 mg, less than 50 mg, less than 40 mg, less than 30 mg, less than 20 mg, less than 15 mg of acetylsalicylic acid, less than 12 mg of acetylsalicylic acid, less than 10 mg of acetylsalicylic acid, less than 8 mg of acetylsalicylic acid, less than 5 mg of acetylsalicylic acid, or less than 2 mg of acetylsalicylic acid.

In other embodiments, the dosage of acetylsalicylic acid (e.g., a single dose) can be from about 2 mg to about 30 mg, about 4 mg to about 25 mg of acetylsalicylic acid, about 6 mg to about 20 mg of acetylsalicylic acid, about 8 mg to about 15 mg of acetylsalicylic acid, about 10 mg to about 13 mg of acetylsalicylic acid, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg of acetylsalicylic acid. Such dosages can provide a bioequivalent dosage when compared to typical dosages of about 81 mg to about 325 mg, while demonstrating few negative side effects.

Thus, a NSAID, such as acetylsalicylic acid, can be administered by DPI or MDI in a single dose or multiple dose that delivers much less than a traditional oral dose of acetylsalicylic acid, which can provide an equivalent treatment while tending to avoid the negative side effects associated with certain NSAIDs, such as acetylsalicylic acid. Further, systems (devices) of administering such treatments are also provided.

The NSAID, in particular acetylsalicylic acid, can be formulated to include pharmaceutically acceptable excipients that are effective to improve aerodynamic performance, bioavailability and/or pharmacokinetics as compared to prior art methods of administration.

The DPI or MDI apparatus can have a mouthpiece and an actuation member for making available the NSAID for inhalation by a patient to reduce the risk of the thromboembolic event.

DPI or MDI suitable for the dry powder compositions and methods disclosed herein can be a reusable device, a disposable device, a pre-filled device, a blistered device, a pre-metered device, or any apparatus that can deliver a dry powder composition for inhalation.

Examples of DPI or MDI include, without limitation, the inhalers disclosed is U.S. Pat. Nos. 4,995,385 and 4,069, 819, Spinhaler® (Fisons, Loughborough, U.K.), Rotahalers®, Diskhaler® and Diskus® (GlaxoSmithKline, Research Triangle Technology Park, N.C.), Ellipta™, Handihaler®, FlowCapss®, Neohaler®, Pressair™, Rotahaler®, Turbuhaler®, Twisthaler®, XCaps (Hovione, Loures, Portugal), Inhalators® (BoehringerIngelheim, Germany), Aerolizer® (Novartis, Switzerland), CDMHaler, Podhaler™, and others known to those skilled in the art.

An example of a DPI can be the DPI disclosed in U.S. Pat. No. 7,559,325, which is incorporated herein by reference in its entirety, including the drawings thereof.

Figure 8:
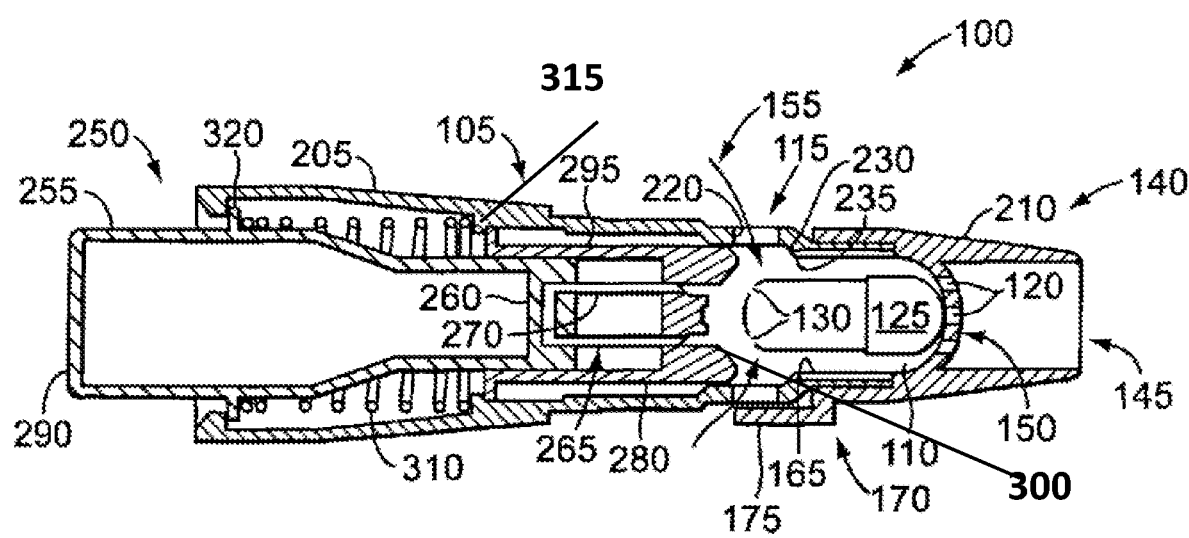
FIG. 8: A section view of an example of a dry powder inhaler (DPI).

As shown in FIG. 8, a DPI 100 comprises a housing 105 defining a chamber 110 having one or more air inlets 115, and one or more air outlets 120. The chamber 110 is sized to receive a capsule 125 which contains a dry powder composition as disclosed herein (e.g., ASA/MgST formulations); a puncturing mechanism 250 in the housing 105 for creating one or more openings 130 in the capsule 125; an optional shield 170 which covers at least two but not all of the air inlets 115, wherein the optional shield 170 comprises one or two or more covering portions 175, each covering portion 175 covering at least one inlet 115, whereby the optional shield 170 prevents blockage of at least two air inlets 115 by a user grasping the apparatus; and an end section 140 associated with the housing 105, the end section 140 sized and shaped to be received in a user's mouth or nose so that the user may inhale through the end section 140 (e.g., through the opening 145 thereof) to aerosolize the dry powder composition and to inhale aerosolized dry powder composition that has exited the capsule 125. The housing 105 comprises a body 205 and a removable endpiece 210. The endpiece 210 may be removed from the body 205 to insert a capsule 125 in the chamber 110 which is formed when the body 205 and the endpiece 210 are connected together. The endpiece 210 comprises a partition 150 which can take any shape (e.g., a dome-shaped shown in FIG. 8) and that blocks the forward end of the chamber 110, and the partition 150 has the one or more outlets 120 extending therethrough. Examples of aerosolization apparatus with a partition 150 and chamber configuration are described in U.S. Pat. Nos. 4,069,819 and 4,995,385, both of which are incorporated herein by reference in their entireties. The inlets 115 may comprise a plurality of tangentially oriented slots 220. When a user inhales through the endpiece 210, outside air is caused to flow through the inlets 115 (e.g., tangential slots 220). This airflow creates a swirling airflow within the chamber 110. The swirling airflow causes the capsule 125 to contact the partition 150 and then to move within the chamber 110 in a manner that causes the dry powder composition to exit the capsule 125 and become entrained within the swirling airflow. In one specific version, the chamber 110 comprises a tapered section 230 that terminates at an edge 235. During the flow of swirling air in the chamber 110, the forward end of the capsule 125 contacts and rests on the partition 150 and a sidewall of the capsule 125 contacts the edge 235 and slides and/or rotates along the edge 235. This motion of the capsule may be particularly effective in forcing a large amount of the dry powder composition through one or more openings 130 in the rear of the capsule 125. The puncturing mechanism 250 may comprises plunger 255 attached at its forward end 260 to a puncture member 265, which in the version shown in FIG. 8 is a U-shaped staple 270 having two sharpened tips 275. The puncturing mechanism 250 further comprises a seating member 280 which contacts the plunger 255 and/or the puncture member 265 and is slidable relative to the plunger 255 and the puncture member 265. To create the openings 130 in the capsule 125, the user applies a force to the plunger 255, such as by pressing against an end surface 290 of the plunger 255 with the user's finger or thumb. The force causes the plunger to slide within the body 205. A slight frictional contact between the plunger 255 and the a rear section 295 of the seating member 280 causes the seating member 280 to also slide within the body 205 until a forward seating surface 300 of the seating member 280 contacts the capsule 125. The forward seating surface 300, which may be shaped to generally match the shape of the capsule 125, secures the capsule 125 between the seating member 280 and the partition 150. The continued application of force causes the plunger 255 and the puncture member 265 to slide relative to the seating member 280 to advance the puncture member 135 through openings 305 in the forward seating surface 300 and into the capsule 125. Upon the removal of the force, a spring 310 or other biasing member urges the puncturing mechanism 250 back to its rest position. For example, the spring 310 may contact a shoulder 315 in the body 205 and press a flange 320 on the plunger 255 toward a rim 325 in the body 205. The frictional engagement between the plunger 255 and the seating member 280 also returns the seating member 280 to its retracted position when the plunger 255 is returned to its retracted position.

Another example of a DPI can be the DPI disclosed in U.S. Pat. No. 8,069,851, which is incorporated herein by reference in its entirety, including the drawings thereof.

Figure 9:
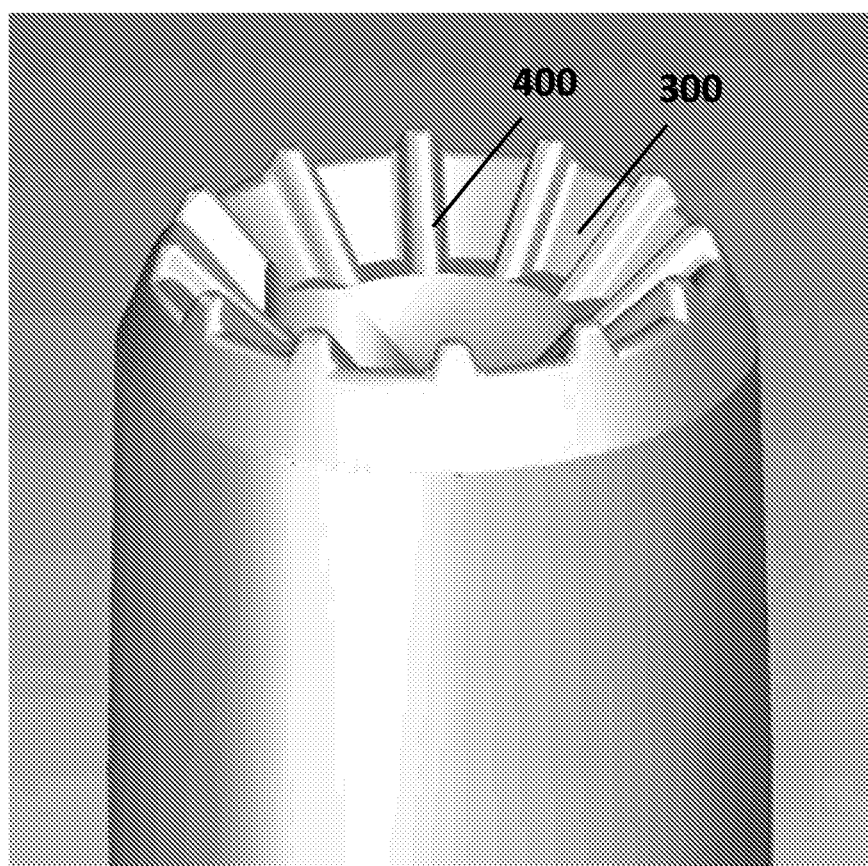
FIG. 9: A perspective view of an example of a forward seating surface comprises one or more protrusions for contacting a capsule.

In certain embodiments, a DPI comprises a housing 105 having one or more two air inlets 115, the inlets 115 configured and dimensioned to produce a swirling airflow (e.g., comprising a plurality of tangentially oriented slots 220); an endpiece 210 comprising a partion 150 (e.g., a perforated member having one or more dry powder composition outlets 120), the endpiece 210 being connectable to the housing to define a chamber 110, the chamber 110 being sized to receive a capsule 125 which contains a dry powder composition disclosed herein (e.g., ASA/MgST formulations), the endpiece 210 further comprising an optional shield 170 which covers at least one air inlet 115, wherein the optional shield 170 comprises at least one covering portion 175, whereby the covering portion 175 prevents blockage of at least one air inlet 115 by a user grasping the apparatus; and a puncturing mechanism 250 disposed within the housing 105 for creating one or more openings 130 in the capsule, the puncturing mechanism 250 comprising an seating member 280 and a puncture member (e.g., the U-shaped staple 270), wherein the seating member 280 comprises a forward seating surface 300 which advances to contact and align the capsule 125 while the seating member 280 and puncture member 270 are advanced into the capsule 125 to create one or more openings 130 in the capsule 125, and wherein the forward seating surface 300 comprises one or more protrusions 400 for contacting the capsule 125 (see, e.g., FIG. 9).

Another example of a DPI can be the DPI disclosed in U.S. Pat. No. 7,516,741, which is incorporated herein by reference in its entirety, including the drawings thereof.

Figure 10:
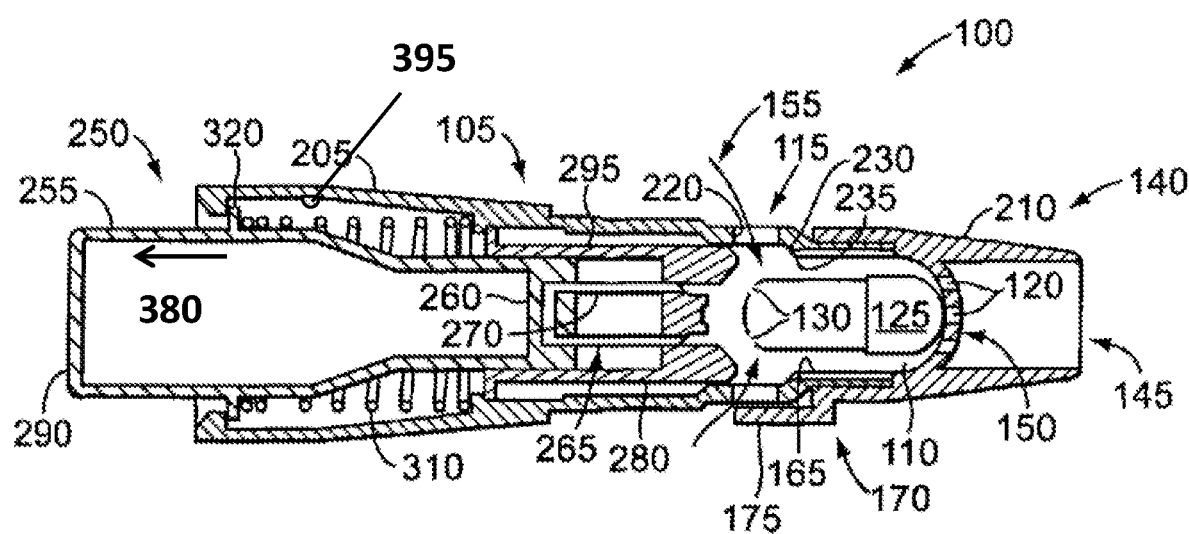
FIG. 10: A section view of an example of a dry powder inhaler (DPI) with a feedback mechanism.

In certain embodiments, a DPI comprises a housing 105 defining a chamber 110 having an air inlet 115 and an air outlet 120, wherein the chamber 110 is sized to receive a capsule 125 containing a dry powder composition disclosed herein (e.g., ASA/MgST formulations); a puncturing member 265 moveable within the chamber 110 to contact the capsule 125 and to provide an opening 130 in the capsule 125; and a feedback mechanism that provides a tactile indication 380 to a user only when the puncturing member 265 has been moved to a predetermined position (e.g., a position where it provides the opening into the capsule) wherein the puncture member 265 is movable beyond the predetermined position, whereby when air flows through the inlet 115, the dry powder composition is aerosolized and the aerosolized dry powder composition is delivered through the outlet 120. As shown in FIG. 10, one or more protrusions 395 may be provided on the body 205 that engages the flange 320 or other section of the plunger 255. In moving the puncturing mechanism 250 in use, resistance is provided by the contact of the flange 320 and the protrusion 395. The resistance is overcome by continued force, and the puncturing mechanism 250 punctures the capsule 125. The resistance and the passage of the flange 320 beyond the protrusion 395 can be detected by the user as a tactile indication 380 that the capsule 125 has been punctured. The protrusion 395 is positioned so that as the flange 320 passes over the protrusion 395, the puncture member 265 penetrates the capsule 125 a predetermined amount. Accordingly, the user is alerted that the puncture has occurred and can stop applying the force. In this way, excessive insertion is prevented. In another version, the arrangement may be reversed with the protrusion being on the plunger and the flange or other contacting member being on the body.

For example, a method of reducing the risk of a thromboembolic event is provided and can comprise administering a dose of a non-steroidal anti-inflammatory drug by a dry powder inhaler. The dose can be effective to reduce a risk of a thromboembolic event in a patient. The dry powder inhaler can have a mouthpiece and an actuation member for making available the dose of the non-steroidal anti-inflammatory drug for inhalation by the patient to reduce the risk of the thromboembolic event.

A drug delivery system can also be provided for treating a disease, for example, by reducing the risk of a thromboembolic (ischemic) event. The drug delivery system can comprise a dry powder composition disclosed herein comprising a dose of a non-steroidal anti-inflammatory drug. The dose can be effective to reduce the risk of a thromboembolic event in a patient. The system can also comprise a dry powder inhaler as disclosed herein. The dry powder inhaler can have a mouthpiece, a reservoir for receiving the dose of the non-steroidal anti-inflammatory drug, and an actuation member for making available the dose of the non-steroidal anti-inflammatory drug for inhalation by the patient through the mouthpiece.

The thromboembolic event may be a myocardial infarction, deep venous thrombosis, pulmonary embolism, or thrombotic stroke. The dose of the NSAID drug can be administered as a preliminary treatment in response to a symptom of a thromboembolic event. The NSAID may be acetylsalicylic acid and may be administered in a single dose or in multiple doses, e.g., 2, 3, 4, 5, 6, 7, 8, 9 or 10 or greater doses.

2. Definitions

The dry particles or dry powder compositions disclosed herein are suitable for delivery to the respiratory tract (e.g., pulmonary delivery) in a subject by inhalation. The dry particles may have a mass median aerodynamic diameter (MMAD) of less than about 20 µm, less than about 15 µm, less than about 10 µm, less than about 5 µm, from about 1 µm to about 10 µm, from about 1 µm to about 5 µm, from about 1 µm to about 3 µm, from about 2 µm to about 3 µm, from about 1.7 µm to about 2.7 µm, or less.

The term "dispersible" describes the characteristic of a dry powder or dry particles to be dispelled into a respirable aerosol. Dispersibility of a dry powder or dry particles is expressed herein as the quotient of the volume median geometric diameter (VMGD) measured at a dispersion (i.e., regulator) pressure of 1 bar divided by the VMGD measured at a dispersion (i.e., regulator) pressure of 4 bar, or VMGD at 0.5 bar divided by the VMGD at 4 bar as measured by HELOS/RODOS. These quotients are referred to herein as "¼ bar," and "0.5/4 bar," respectively, and dispersibility correlates with a low quotient. For example, ¼ bar refers to the VMGD of respirable dry particles or powders emitted from the orifice of a RODOS dry powder disperser (or equivalent technique) at about 1 bar, as measured by a HELOS or other laser diffraction system, divided the VMGD of the same respirable dry particles or powders measured at 4 bar by HELOS/RODOS. Thus, a highly dispersible dry powder or dry particles will have a ¼ bar or 0.5/4 bar ratio that is close to 1.0. Highly dispersible powders have a low tendency to agglomerate, aggregate or clump together and/or, if agglomerated, aggregated or clumped together, are easily dispersed or de-agglomerated as they emit from an inhaler and are breathed in by the subject. Dispersibility can also be assessed by measuring the size emitted from an inhaler as a function of flow rate.

The term "emitted dose" or "ED" refers to an indication of the delivery of the API of a drug formulation from a suitable inhaler device after a firing or dispersion event. More specifically, for dry powder compositions, the ED may be the mass of the API that is drawn out of a unit dose package and that exits the mouthpiece of an inhaler device. Alternatively, the ED may be the ratio of the ApI dose delivered by an inhaler device to the nominal dose (i.e., the mass of powder per unit dose placed into a suitable inhaler device prior to firing). The ED is an experimentally-measured parameter, and can be determined using the method of USP Section 601 Aerosols, Metered-Dose Inhalers and Dry Powder Inhalers, Delivered-Dose Uniformity, Sampling the Delivered Dose from Dry Powder Inhalers, United States Pharmacopeia Convention, Rockville, Md., 13th Revision, 222-225, 2007. This method utilizes an in vitro device set-up to mimic patient dosing.

The portion of the drug formulation falling within a size range is typically referred to as the fine particle fraction (FPF).

Unless otherwise specified, the term "FPF" or "fin particle fraction" is referred to the fraction of a sample of dry particles that have an aerodynamic diameter of less than 5.0 µm, which may also be referred to as "FPF (<5.0)," "FPF (<5.0 µm)," and "fine particle fraction of less than 5.0 µm."

The terms "FPF (<3.0)," "FPF (<3.0 µm)," and "fine particle fraction of less than 3.0 µm" refers to the fraction of a mass of respirable dry particles that have an aerodynamic diameter of less than 3.0 µm.

The term "about" as used herein, unless otherwise specified, means ±10% of the numeric value following the term "about."

3. Non-Steroidal Anti-Inflammatory Drugs (NSAIDs)

NSAIDs, such as acetylsalicylic acid, can provide various beneficial effects and contribute to reducing the risk of a cardiovascular disease (such as thrombosis). However, the use of NSAIDs, such as acetylsalicylic acid, in a clinical setting has traditionally been limited to oral administration. Oral administration of acetylsalicylic acid, for example, can result in the loss or inactivation of approximately ⅔ of the oral dosage due to the first pass effect in the gut and liver. While one third of the dosage reaches the systemic blood stream and provides the desired effect, the negative side effects created by the full dosage often deter patients from using acetylsalicylic acid on a regular or daily basis.

The methods and systems of the present invention allow for the beneficial effects of NSAIDs, such as acetylsalicylic acid, to be achieved on a regular basis and in emergency situations, while minimizing previous drawbacks associated with the use of NSAIDs.

Various studies have determined that acetylsalicylic acid has a significant effect on reducing the risk of myocardial infarction. These studies have used acetylsalicylic acid dosages of 325 mg. However, these studies have based their findings on oral administration of acetylsalicylic acid and have not suggested DPI or MDI administration.

Although inhaled dry powder compositions of acetylsalicylic acid have been developed, reports have stated that the formulation was not clinically feasible because it is difficult to meet the high dosage requirements of acetylsalicylic acid (~80 mg/day for low-dose prevention of coronary events and stroke, and at least 300 mg/day for pain or fever relief) via pulmonary delivery of dry powders.

In addition, these reports recognize that adverse effects of dry powder on the lungs, such as coughing, cannot be avoided unless the doses are less than a few tenths of a milligram in a single breath. Thus, prior teachings suggest that higher dosage requirements of acetylsalicylic acid would be impossible or difficult to meet using DPI (or MDI). Finally, there may be a higher incidence of acetylsalicylic acid intolerance in asthmatic patients when acetylsalicylic acid is delivered by inhalation than orally.

The methods and systems of the present invention provide for treating (including prophylactic treatment or reducing the risk of) a disease, for example, treating a cardiovascular disease (such as thrombosis) by administration of a low amount of a NSAID, such as a low dose of acetylsalicylic acid, by DPI. The dose can be much less than that of a baby acetylsalicylic acid (e.g., less than 81 mg). The administered dosage can be less than about 40 mg of acetylsalicylic acid. The administered dosage can be less than 25 mg of acetylsalicylic acid. Further, the administered dosage can be less than 20 mg of acetylsalicylic acid. The administered dosage can be less than 15 mg of acetylsalicylic acid. The administered dosage can also be less than 12 mg of acetylsalicylic acid. The administered dosage can be less than 10 mg of acetylsalicylic acid. Furthermore, the administered dosage can be less than 8 mg of acetylsalicylic acid. The administered dosage can be less than 5 mg of acetylsalicylic acid. In some embodiments, the administered dosage can be less than 2 mg of acetylsalicylic acid.

For example, the dosage can be from about 1 mg to about 40 mg. In various embodiments, the dosage can be from about 4 mg to about 25 mg of acetylsalicylic acid, about 6 mg to about 20 mg of acetylsalicylic acid, about 8 mg to about 15 mg of acetylsalicylic acid, about 10 mg to about 13 mg of acetylsalicylic acid or about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg of acetylsalicylic acid. Alternatively, the dose of acetylsalicylic acid can be less than about 80 mg, about 1 mg to about 75 mg, about 2 mg to about 60 mg, about 5 mg to about 40 mg, about 10 mg to about 30 mg, about 12 mg to about 25 mg, about 15 mg to about 20 mg, about 60 mg to about 95 mg, about 50 mg to about 100 mg, about 50 mg to about 80 mg, about 40 mg to about 80 mg, about 20 mg to about 30 mg, about 30 mg to about 40 mg, about 40 mg to about 50 mg, about 50 mg to about 60 mg, about 60 mg to about 70 mg, about 70 mg to about 80 mg, about 80 mg to about 90 mg, or about 90 mg to about 100 mg.

In certain embodiments, NSAIDs can be used in various methods and systems. In some embodiments, NSAIDs can include salicylates, i.e., the salts and esters of salicylic acid, which have anti-platelet action. Further, NSAIDs can also include one or more of the following compounds listed in Table 1.

TABLE 1

Examples of NSAIDs

Aspirin or acetylsalicylic acid
Celecoxib (Celebrex)
Dexdetoprofen (Keral)
Diclofenac (Voltaren, Cataflam, Voltaren-XR)
Diflunisal (Dolobid)
Etodolac (Lodine, Lodine XL)
Etoricoxib (Algix)
Fenoprofen (Fenopron, Nalfron)
Firocoxib (Equioxx, Previcox)
Flurbiprofen (Urbifen, Ansaid, Flurwood, Proben)
Ibuprofen (Advil, Brufen, Motrin, Nurofen, Medipren, Nuprin)
Indomethacin (Indocin, Indocin SR, Indocin IV)
Ketoprofen (Actron, Orudis, Oruvail, Ketoflam)
Ketorolac (Toradol, Sprix, Toradol IV/IM, Toradol IM)
Licofelone (under development)
Lornoxicam (Xefo)
Loxoprofen (Loxonin, Loxomac, Oxeno)
Lumiracoxib (Prexige)
Meclofenamic acid (Meclomen)
Mefenamic acid (Ponstel)
Meloxicam (Movalis, Mel ox, Recoxa, Mobic)
Nabumetone (Relafen)
Naproxen (Aleve, Anaprox, Midol Extended Relief, Naprosyn, Naprelan)
Nimesulide (Sulide, Nimalox, Mesulid)
Oxaporozin (Daypro, Dayrun, Duraprox)
Parecoxib (Dynastat)
Piroxicam (Feldene)
Rofecoxib (Vioxx, Ceoxx, Ceeoxx)
Salsalate (Mono-Gesic, Salflex, Disalcid, Salsitab)
Sulindac (Clinoril)
Tenoxicam (Mobi flex)
Tolfenamic acid (Clotam Rapid, Tufnil)
Valdecoxib (Bextra)

Other alternatives can also be used instead of a NSAID. Such alternatives include Plavix (clopidogrel), COX-2 inhibitors, other remedies such as Nattokinase (an enzyme (EC 3.4.21.62, extracted and purified from a Japanese food called nattō)). Further, other drugs that provide different beneficial effects, such as being effective to reduce a risk of a cardiovascular disease (such as thrombosis) in a patient, can also be used in some embodiments. Thus, the discussion of methods and systems shall apply generally to these various alternatives, although for discussion purposes, the present disclosure often refers to acetylsalicylic acid. It is contemplated that the methods, effects, pharmacokinetic data, and other considerations relating to acetylsalicylic acid can be equally applied to other NSAIDs.

4. Dry Powders and Dry Particles

The dry particles and dry powder compositions disclosed herein are dispersible. The size of the dry particles can be expressed in a variety of ways that are conventional in the art, such as, fine particle fraction (FPF), volumetric median geometric diameter (VMGD), mass median aerodynamic diameter (MMAD), geometric standard deviation (GSD), and emitted dose (ED).

The dry particles of the subject technology may have a VMGD as measured by HELOS/RODOS at 1.0 bar of about 10 μm or less (e.g., about 0.1 μm to about 10 μm). Preferably, the dry particles of the subject technology have a VMGD of about 9 μm or less (e.g., about 0.1 μm to about 9 μm), about 8 μm or less (e.g., about 0.1 μm to about 8 μm), about 7 μm or less (e.g., about 0.1 μm to about 7 μm), about 6 μm or less (e.g., about 0.1 μm to about 6 μm), about 5 μm or less (e.g., less than 5 μm, about 0.1 μm to about 5 μm), about 4 μm or less (e.g., 0.1 μm to about 4 μm), about 3 μm or less (e.g., 0.1 μm to about 3 μm), about 2 μm or less (e.g., 0.1 μm to about 2 μm), about 1 μm or less (e.g., 0.1 μm to about 1 μm), about 0.5 μm to about 6 μm, about 0.5 μm to about 5 μm, about 0.5 μm to about 4 μm, about 0.5 μm to about 3 μm, or about 0.5 μm to about 2 μm as measured by HELOS/RODOS at 1.0 bar. In an exemplary embodiment, the dry particles of the subject technology have a VMGD as measured by HELOS/RODOS at 1.0 bar of about 1.3 to about 1.7 μm. In another exemplary embodiment, the dry particles of the subject technology have a VMGD as measured by HELOS/RODOS at 1.0 bar of about 0.5 μm to about 2 μm.

Alternatively, the dry particles may have a VMGD as measured by HELOS/RODOS at 1.0 bar of about 30 μm or less (e.g., about 5 μm to about 30 μm). Preferably, the dry particles of the subject technology have a VMGD of about 25 μm or less (e.g., about 5 μm to about 25 μm), about 20 μm or less (e.g., about 5 μm to about 20 μm), about 15 μm or less (e.g., about 5 μm to about 15 μm), about 12 μm or less (e.g., about 5 μm to about 12 μm), about 10 μm or less (e.g., about 5 μm to about 10 μm), or about 8 μm or less (e.g., 6 μm to about 8 μm) as measured by HELOS/RODOS at 1.0 bar. The dry powders can comprise a mixture of particles having different sizes.

The respirable dry particles can have an MMAD of about 10 μm or less, such as an MMAD of about 0.5 μm to about 10 μm, about 1 μm to about 10 μm, about 0.5 μm to about 5 μm, about 2 μm to about 3 μm, or about 1 μm to about 5 μm. Preferably, the dry particles of the subject technology have an MMAD of about 5 μm or less (e.g. about 0.5 μm to about 5 μm, preferably about 1 μm to about 5 μm), about 4 μm or less (e.g., about 1 μm to about 4 μm), about 3.8 μm or less (e.g. about 1 μm to about 3.8 μm), about 3.5 μm or less (e.g. about 1 μm to about 3.5 μm), about 3.2 μm or less (e.g. about 1 μm to about 3.2 μm), about 3 μm or less (e.g. about 1 μm to about 3.0 μm), about 2.8 μm or less (e.g. about 1 μm to about 2.8 μm), about 2.2 μm or less (e.g. about 1 μm to about 2.2 μm), about 2.0 μm or less (e.g. about 1 μm to about 2.0 μm) or about 1.8 μm or less (e.g. about 1 micron to about 1.8 μm).

Alternatively, the dry powder compositions disclosed herein have a geometric standard deviation (GSD) of about 2.5 μm or lower.

Alternatively, the dry powder compositions disclosed herein have an emitted dose (ED) of about 75% or higher.

Alternatively, the dry powders and dry particles of the subject technology have a FPF of less than 5.0 μm (FPF_TD<5.0 μm) of at least about 20%, at least about 30%, at least about 45%, at least about 40%, at least about 45%, at least about 50%, at least about 60%, at least about 65% or at least about 70%. Alternatively or in addition, the dry powders and dry particles of the subject technology have a FPF of less than 5.0 μm of the emitted dose (FPF_ED<5.0 μm) of at least about 45%, at least about 50%, at least about 60%, at least about 65%, at least about 70%, at least about 75%, at least about 80%, or at least about 85%.

In another embodiment, the dry powders and dry particles of the invention can have an FPF of less than about 5.6 μm (FPF<5.6 μm) of at least about 20%, at least about 30%, at least about 40%, preferably at least about 45%, at least about 50%, at least about 55%, at least about 60%, at least about 65%, or at least about 70%.

In a third embodiment, embodiment, the dry powders and dry particles of the invention can have an FPF of less than about 3.4 μm (FPF<3.4 μm) of at least about 20%, preferably at least about 25%, at least about 30%, at least about 35%, at least about 40%, at least about 45%, at least about 50%, or at least about 55%.

The dry powders and dry particles may have a tap density of about 0.1 $g/cm^3$ to about 1.0 $g/cm^3$. For example, the small and dispersible dry particles have a tap density of about 0.1 $g/cm^3$ to about 0.9 $g/cm^3$, about 0.2 $g/cm^3$ to about 0.9 $g/cm^3$, about 0.2 $g/cm^3$ to about 0.9 $g/cm^3$, about 0.3 $g/cm^3$ to about 0.9 $g/cm^3$, about 0.4 $g/cm^3$ to about 0.9 $g/cm^3$, about 0.5 $g/cm^3$ to about 0.9 $g/cm^3$, or about 0.5 $g/cm^3$ to about 0.8 $g/cm^3$, greater than about 0.4 g/cc, greater than about 0.5 g/cc, greater than about 0.6 g/cc, greater than about 0.7 g/cc, about 0.1 $g/cm^3$ to about 0.8 $g/cm^3$, about 0.1 $g/cm^3$ to about 0.7 $g/cm^3$, about 0.1 $g/cm^3$ to about 0.6 $g/cm^3$, about 0.1 $g/cm^3$ to about 0.5 $g/cm^3$, about 0.1 $g/cm^3$ to about 0.4 $g/cm^3$, about 0.1 $g/cm^3$ to about 0.3 $g/cm^3$, less than 0.3 $g/cm^3$. In a preferred embodiment, tap density is greater than about 0.4 $g/cm^3$; in another preferred embodiment, tap density is greater than about 0.5 $g/cm^3$. Alternatively, tap density may be less than about 0.4 $g/cm^3$.

The dry powders and dry particles can have a water or solvent content of less than about 15% by weight of the dry particle. For example, the dry particles can have a water or solvent content of less than about 15% by weight, less than about 13% by weight, less than about 11.5% by weight, less than about 10% by weight, less than about 9% by weight, less than about 8% by weight, less than about 7% by weight, less than about 6% by weight, less than about 5% by weight, less than about 4% by weight, less than about 3% by weight, less than about 2% by weight, less than about 1% by weight or be anhydrous. In another embodiment, the dry particles of the subject technology can have a water or solvent content of less than about 6% and greater than about 1%, less than about 5.5% and greater than about 1.5%, less than about 5% and greater than about 2%, about 2%, about 2.5%, about 3%, about 3.5%, about 4%, about 4.5% about 5%.

Depending on the specific applications, the present composition (e.g., the present dry powders or dry particles) may contain a low or high percentage of API in the composition. For example, the dry particles may contain 3% or more, 5% or more, 10% or more, 15% or more, 20% or more, 25% or more, 30% or more, 35% or more, 40% or more, 50% or more, 60% or more, 70% or more, 75% or more, 80% or more, 85% or more, 90% or more, 95% or more, about 99% or more, about 40% to about 95%, about 50% to about 95%, about 30% to about 99%, about 40% to about 99%, about 50% to about 99%, about 60% to about 99%, about 70% to about 99%, about 80% to about 99%, about 97.5%, about 99.5%, about 99.75%, about 99.9%, about 99.95%, or about 99.9% (weight percentage, w/w) of the active ingredient (e.g., ASA).

5. Delivery of Dry Powders

In a dry powder inhalation technique, a patient can use a dry powder inhaler to inhale a powder formulation of a drug, such as a NSAID. The dose is effective to reduce a risk of a thromboembolic event in the patient.

Various types of inhalers can be used to provide the drug using a DPI or MDI delivery system. The dose administered can be effective to reduce a risk of a thromboembolic event in a patient.

For example, the dry powder inhaler can comprise a mouthpiece, a reservoir for receiving the dry powder composition comprising an API (e.g., NSAID), and an actuation member for making available the dry powder composition for inhalation by a patient through the mouthpiece.

The methods and systems of the present invention may be adapted for use with any DPI or MDI device, including, but not limited to the inhalers disclosed is U.S. Pat. Nos. 4,995,385 and 4,069,819, Spinhaler® (Fisons, Loughborough, U.K.), Rotahalers®, Diskhaler® and Diskus® (GlaxoSmithKline, Research Triangle Technology Park, N.C.), Ellipta™, Handihaler®, FlowCapss®, Neohaler®, Pressair™, Rotahaler®, Turbuhaler®, Twisthaler®, XCaps (Hovione, Loures, Portugal), Inhalators® (BoehringerIngelheim, Germany), Aerolizer® (Novartis, Switzerland), CDMHaler, and Podhaler™, (see, e.g., http://www.nationaljewish.org/healthinfo/medications/devices/dry-powder).

The methods and systems of the invention provide an apparatus and method for providing a therapeutically effective dose of an API (e.g., an NSAID) in order to reduce the risk of a thromboembolic event. As discussed above, the general approach is to deliver an NSAID in a pharmaceutically acceptable powdered form (e.g., Acetylsalicylic acid, and/or derivatives thereof) by means of an inhaler.

With respect to the particle size distribution (PSD) and aerodynamic particle size distribution (APSD), the dry powder compositions disclosed herein may contain particles having same (or similar) size distribution, or particles having different size distributions. The particle sizes of the dry powder compositions disclosed herein may have a mono-modal, bimodal or multimodal distribution. As a result, the dry powder compositions disclosed herein may produce mono-modal, bimodal or multimodal absorption. In other words, administration of the dry powder compositions disclosed herein may result in a mono-modal, bimodal or multimodal concentration-time profile.

For example, the dry powder compositions disclosed herein may contain one, two or three groups of the following: particles with a median aerodynamic diameter in a range from about 1 µm to about 5 µm or from about 2 µm to about 3 µm, particles with a median aerodynamic diameter in a range from about 5 µm to about 15 µm, and particles with a median aerodynamic diameter greater than about 15 µm, Mixing particles of the same API (e.g., acetylsalicylic acid), using batches of particles having different size distributions, may reduce bridging. For example, while a composition having a relatively uniform particle size will aggregate, providing a blended composition having some particles with a median aerodynamic diameter in a range from about 1 µm to about 5 µm, other particles with a median aerodynamic diameter in a range from about 5 µm to about 15 µm, and still other particles with a median aerodynamic diameter greater than about 15 µm, may inhibit aggregation and maintain the deposition characteristics of the preparation. In effect, the pharmaceutically active compound is used to replace the function of an excipient (such as lactose) with respect to preventing aggregation during storage of the medicament.

In addition, by selecting the proportions of the various particle sizes, one can provide formulations that are faster or slower acting, based on the location of where the drug is ultimately deposited. For example, some embodiments provide a preparation that comprises 80% acetylsalicylic acid particles with a median aerodynamic diameter of about 1 µm to about 5 µm, and about 20% of particles with a median aerodynamic diameter of at least 15 µm. Other combinations are possible as well, and those of skill in the art will readily appreciate that faster acting preparations will comprise proportionately more smaller particles, while slower acting preparations will comprise proportionately more large particles. Thus, using the apparatus and methods described herein it is therefore possible to provide a therapeutically effective dose of an API (e.g., an NSAID such as acetylsalicylic acid) via the respiratory tract, at least as rapidly as can be achieved by oral dosing.

Where a slower acting dosage form is desired, the formulation may include increasing fractions of particles with a median aerodynamic diameter in the range from about 5 µm to about 10 µm, or 15 µm or greater. These preparations would result in deposition in either the airways or oral cavity and pharynx and thus provide a more gradual increase in circulating levels of acetylsalicylic acid and its metabolic derivatives.

Accordingly, one aspect of the subject technology provides a dry powder that comprises a mixture of particles of various sizes.

For example, the dry powder or the dry powder compositions disclosed herein can comprise particles of large sizes, as measured by VMGD (e.g., VMGD≥15 µm, such as ≥20 µm or 20-30 µm) and of small sizes, as measured by VMGD (e.g., VMGD≤5 µm, such as 1-3 µm) at a ratio (w:w) of: about 1:1, about 1:2, about 1:3, about 1:4, about 1:5, about 1:6, about 1:7, about 1:8, about 1:10, about 1:15, about 1:20, about 1:25, about 1:30, about 1:40, about 1:50, about 1:100, about 2:1, about 3:1, about 4:1, about 5:1, about 6:1, about 7:1, about 8:1, about 9:1, about 10:1, about 15:1, about 20:1, about 25:1, about 30:1, about 40:1, about 50:1, or about 100:1, etc.

Alternatively, the dry powder or the dry powder compositions disclosed herein can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having VMGD of about 10 µm or less, preferably about 5 µm or less. Particles of 10 µm or less generally can reach lungs, and particles of 5 µm or less (e.g., 1-3 µm) generally can reach alveoli.

In another embodiment, the dry powder or the dry powder compositions disclosed herein can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having VMGD of between about 5 µm to about 20 µm, preferably between about 5 µm to about 15 µm, or between about 5 µm to about 10 µm.

Alternatively, the dry powder or the dry powder compositions disclosed herein can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having VMGD of about 15 µm, 20 µm or more.

The above features can be combined. For example, the dry power or the dry powder compositions disclosed herein can comprise about 50% of particles of about 5 μm or less (VMGD), about 25% of particles of about 5 to about 15 μm (VMGD), and about 25% of particles of about 15 μm or more (VMGD).

The dry powder or the dry powder compositions disclosed herein can also comprise a mixture of particles having various mass median aerodynamic diameters (MMAD). For example, the dry powder or the dry powder compositions disclosed herein can comprise particles of large sizes (e.g., MMAD 2: 15 μm, such as 2:20 μm or 20-30 μm) and of small sizes (e.g., MMAD: 5 μm, such as 1-3 μm) at a ratio (w:w) of: about 1:1, about 1:2, about 1:3, about 1:4, about 1:5, about 1:6, about 1:7, about 1:8, about 1:10, about 1:15, about 1:20, about 1:25, about 1:30, about 1:40, about 1:50, about 1:100, about 2:1, about 3:1, about 4:1, about 5:1, about 6:1, about 7:1, about 8:1, about 9:1, about 10:1, about 15:1, about 20:1, about 25:1, about 30:1, about 40:1, about 50:1, or about 100:1, etc.

Alternatively, the dry powder or the dry powder compositions disclosed herein can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having MMAD of about 10 μm or less, preferably about 5 μm or less. Particles of 10 μm or less generally can reach lungs, and particles of 5 μm or less (e.g., 1-3 μm) generally can reach alveoli.

In another embodiment, the dry powder or the dry powder compositions disclosed herein can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having MMAD of between about 5 μm to about 20 μm, preferably between about 5 μm to about 15 μm, or between about 5 μm to about 10 μm.

In another embodiment, the dry powder or the dry powder compositions disclosed herein can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having MMAD of about 15 μm or more, preferably 20 μm or more.

The above features can be combined. For example, the dry power can comprise about 50% of particles of about 5 μm or less (MMAD), about 25% of particles of about 5 to about 15 μm (MMAD), and about 25% of particles of about 15 μm or more (MMAD).

In certain embodiments, the dry powder compositions disclosed herein may not have excipients other than MgST, which may be an anti-aggregation (or anti-bridging) excipient.

The dry powder compositions disclosed herein can comprise a mixture of particles of various sizes, and is effective to substantially prevent or reduce particle bridging. In certain embodiments, at least about 40%, at least about 45%, at least about 50%, at least about 55%, at least about 60%, at least about 65%, at least about 70%, at least about 75%, at least about 80%, at least about 85%, or at least about 90% of the API (e.g., NSAID (such as acetylsalicylic acid)) in the dry powder is delivered to the alveolar spaces of a lung.

6. Methods for Preparing Dry Powders and Dry Particles

The dry particles and dry powder compositions disclosed herein can be prepared using any suitable method. Many suitable methods for preparing dry powders and particles are conventional in the art, and include single and double emulsion solvent evaporation, spray drying, milling (e.g., jet milling), blending, solvent extraction, solvent evaporation, phase separation, simple and complex coacervation, interfacial polymerization, suitable methods that involve the use of supercritical carbon dioxide ($CO_2$), co-micronization, and other suitable methods. Dry particles can be made using methods for making microspheres or microcapsules known in the art. These methods can be employed under conditions that result in the formation of dry particles having the desired aerodynamic properties (e.g., aerodynamic diameter and geometric diameter) and unexpected stability as disclosed herein. If desired, dry particles with desired properties, such as size and density, can be selected using suitable methods, such as sieving.

Co-Micronization

The API/MgST dry powder compositions disclosed herein can be prepared by co-micronization. Suitable co-micronization techniques are described, for example, by Stank and Stechel, "Physico-chemical characterization of surface modified particles for inhalation," International Journal of Pharmaceutics, 2013, 448:9-18, which is herein incorporated by reference in its entirety.

In certain embodiments, the micronized powders are rested for 24 hours and packaged.

Other Excipients

The API/MgST dry powder compositions disclosed herein can be encapsulated, e.g., by another pharmaceutical excipient such as lactose, sugar, or a polymer. In certain embodiments, the other pharmaceutical excipient is hydrophobic. In certain embodiments, the other pharmaceutical excipient is a fatty acid with about 10 to about 30 carbons, or about 19 to about 30 carbons.

In addition, the API/MgST dry powder compositions disclosed herein can be mixed and/or coated with various pharmaceutically acceptable excipients. Excipients can be included in order to improve aerodynamic performance of the active drug, to improve bioavailability, increase stability, to modulate pH, to provide sustained release properties, to provide taste-masking of an irritating drug and/or to improve pharmacokinetic performance.

With dry powder compositions, excipients can also provide a carrier function to reduce clumping of the active pharmaceutical ingredient and to improve suspension of the formulation in the airflow as the pharmaceutical preparation is being inhaled. Such carriers can include substances such as, but not limited to, sugars/sugar alcohols such as glucose, saccharose, lactose and fructose, starches or starch derivatives, oligosaccharides such as dextrins, cyclodextrins and their derivatives, polyvinylpyrrolidine, alginic acid, tylose, silicic acid, cellulose, cellulose derivatives, sugar alcohols such as mannitol or sorbitol, calcium carbonate, calcium phosphate, lactose, lactitol, dextrates, dextrose, maltodextrin, saccharides including monosaccharides, disaccharides, polysaccharides; sugar alcohols such as arabinose, ribose, mannose, sucrose, trehelose, maltose and dextran.

In some cases, an excipient can be provided in order to coat the active pharmaceutical ingredient, thus "masking" it.

Masking is especially useful when the unmodified active pharmaceutical is irritating or otherwise unpleasant to the recipient. For example, in some cases it has been shown that coating a bitter molecule with a hydrogenated oil and surfactant combination is effective to cover the otherwise unpleasant taste of the active ingredient.

Non-limiting examples of pharmaceutically acceptable excipients include phospholipids. The phospholipids may or may not have surfactant properties. Examples of suitable phospholipid excipients include, without limitation, phosphatidylcholines, phosphatidylethanolamines, phosphatidylinositol, phosphatidylserines, sphingomyelin or other ceramides, as well as phospholipid containing oils such as lecithin oils. Combinations of phospholipids, or mixtures of a phospholipid(s) and other substance(s), may be used. In one embodiment, the phospholipids used as excipients are soy lecithin. In another embodiment, the phospholipid is endogenous to the lung.

Non-limiting examples of the phospholipids that may be used in the present composition include, soy lecithin, dipalmitoylphosphatidylcholine (DPPC), distearoylphosphatidylcholine (DSPC), dilaurylolyphosphatidylcholine (DLPC), dimyristoylphosphatidylcholine (DMPC), dioleoylphosphatidylcholine (DOPC), dilaurylolylphosphatidylglycerol (DLPG), dimyristoylphosphatidylglycerol (DMPG), dipalmitoylphosphatidylglycerol (DPPG), distearoylphosphatidylglycerol (DSPG), dioleoylphosphatidylglycerol (DOPG), dimyristoyl phosphatidic acid (DMPA), dimyristoyl phosphatidic acid (DMPA), dipalmitoyl phosphatidic acid (DPPA), dipalmitoyl phosphatidic acid (DPPA), dimyristoyl phosphatidylethanolamine (DMPE), dipalmitoyl phosphatidylethanolamine (DPPE), dimyristoyl phosphatidylserine (DMPS), dipalmitoyl phosphatidylserine (DPPS), dipalmitoyl sphingomyelin (DPSP), and distearoyl sphingomyelin (DSSP).

In one embodiment, soy lecithin, dipalmitoyl phosphatidylcholine (DPPC), distearoyl phosphatidylcholine (DSPC) or a mixture thereof are used as an excipient.

An excipient may be used to in the present composition. The excipient(s) may be present at levels ranging from about 0% to about 99% (w/w), from about 0.01% to about 80% (w/w), from about 0.05% to about 70% (w/w), from about 0.1% to about 60% (w/w), from about 0.1% to about 50% (w/w), from about 0.1% to about 40% (w/w), from about 0.1% to about 30% (w/w), from about 0.1% to about 20% (w/w), from about 0.1% to about 10% (w/w), from about 0.05% to about 8% (w/w), from about 0.1% to about 6% (w/w), from about 5% to about 10% (w/w), from about 3% to about 8% (w/w), from about 2% to about 6% (w/w), from about 0.1% to about 5% (w/w), from about 0.1% to about 4% (w/w), from about 0.1% to about 3% (w/w), from about 0.1% to about 2% (w/w), from about 0.1% to about 1% (w/w), from about 1% to about 6% (w/w), from about 1% to about 5% (w/w), from about 1% to about 4% (w/w), or from about 1% to about 3% (w/w) of the particles. In certain embodiments, one or more excipients (e.g., one or more phospholipids) are present at levels in a range from about 0.1% to about 10% (w/w), from about 1% to about 5% (w/w), about 0.1%, about 5% (w/w), about 3%, or about 10% (w/w) of the particles.

In addition, in some embodiments, the surfactant can be provided in combination with one or more additional excipients including absorbents, acidifiers, alkalizers, buffers, antimicrobial agents, antioxidants, binders, solubilizing agents, solvents, viscosity modifiers, humectants and combinations thereof. In some embodiments the formulation includes salts in amounts effective to render the dissolved formulation isosmotic with the lung.

Respirable dry particles and dry powder compositions disclosed herein can be fabricated and then separated, for example, by filtration or centrifugation by means of a cyclone, to provide a particle sample with a preselected size distribution. For example, greater than about 30%, greater than about 40%, greater than about 50%, greater than about 60%, greater than about 70%, greater than about 80%, or greater than about 90% of the respirable dry particles in a sample can have a diameter within a selected range. The selected range within which a certain percentage of the respirable dry particles fall can be, for example, any of the size ranges described herein, such as between about 0.1 to about 3 µm VMGD.

The diameter of the respirable dry particles, for example, their VMGD, can be measured using an electrical zone sensing instrument such as a Multisizer lie, (Coulter Electronic, Luton, Beds, England), or a laser diffraction instrument such as a HELOS system (Sympatec, Princeton, N.J.). Other instruments for measuring particle geometric diameter are well known in the art. The diameter of respirable dry particles in a sample will range depending upon factors such as particle composition and methods of synthesis. The distribution of size of respirable dry particles in a sample can be selected to permit optimal deposition within targeted sites within the respiratory system.

Experimentally, aerodynamic diameter can be determined using time of flight (TOF) measurements. For example, an instrument such as the Model 3225 Aerosizer DSP Particle Size Analyzer (Amherst Process Instrument, Inc., Amherst, Mass.) can be used to measure aerodynamic diameter. The Aerosizer measures the time taken for individual respirable dry particles to pass between two fixed laser beams.

Aerodynamic diameter also can be experimentally determined directly using conventional gravitational settling methods, in which the time required for a sample of respirable dry particles to settle a certain distance is measured. Indirect methods for measuring the mass median aerodynamic diameter include the Andersen Cascade Impactor (ACI) and the multi-stage liquid impinger (MSLI) methods. Another method of measuring the aerodynamic diameter is with a Next Generation Impactor (NGI). The NGI operates on similar principles of inertial impaction as the ACI. The NGI consists of seven stages and can be calibrated at flow rates of 30, 60, and 100 LPM. In contrast to the ACI, for which the impactor stages are stacked, the stages of the NGI are all in one plane. Collection cups are used to collect the particles below each stage of the NGI. U.S. Pat. No. 8,614, 255. The methods and instruments for measuring particle aerodynamic diameter are well known in the art. Unless otherwise specified, the NGI characterizations disclosed herein are obtained according to USP <601> NGI (apparatus 5) method requiring a 4k Pa pressure drop (see, e.g., www.pharmacopeia.cn/v29240/
usp29nf24s0_c601_viewall.html, which is incorporated herein by reference).

The dry powder compositions disclosed herein comprise substantially dry particles having a mass median aerodynamic diameter (MMAD) within a range of about 0.5 µm to about 10 µm, or about 2 µm to about 3 µm, wherein the dry powder compositions disclosed herein further comprises one or more phospholipids in an amount ranging from about 0.1% (w/w) to about 10% (w/w) of the dry particles. The particles may have an MMAD size distribution where the particles exhibit: (i) a DV90 less than about 20 µm, a DV50 less than about 7 µm, and a DV10 less than about 2 µm; (ii) a DV90 less than about 10 µm, a DV50 less than about 4 µm, and a DV10 less than about 1 µm; or (iii) a DV90 less than about 6 µm, a DV50 less than about 3 µm, and a DV10 less than about 1 µm.

The dry powder compositions disclosed herein may comprise particles coated with a pharmaceutically acceptable excipient. The pharmaceutically acceptable excipient can be a phospholipid having surfactant properties, such as dipalmitoyl phosphatidylcholine (DPPC), distearoyl phosphatidylcholine (DSPC) or soy lecithin, in an amount ranging from about 0.1% to about 10% w/w or in an amount ranging from about 1% to about 5% w/w. In one embodiment, the weight percentage of the DSPC on the dry particles is 5% w/w. In another embodiment, the respirable dry powder of the soy lecithin of the dry particles is 0.1% w/w.

In certain embodiments, the drug delivery system disclosed herein is effective in reducing the risk of a thromboembolic event or treat thrombosis. The dose of acetylsalicylic acid may be present at amounts ranging from about 5 mg to about 40 mg. The formulation my further comprise clopidogrel. The respirable dry powders can have an emitted dose ranging from about 75% to about 95%.

In certain embodiments, the dry powder composition disclosed herein (e.g., ASA/MgST) substantially comprise dry particles having a MMAD ranging from about 2.0 to about 3.0 µm and an emitted dose ranging from about 55% to about 85%, about 58% to about 85%, or about 70% to about 85%. In this embodiment, the mass percent of API (e.g., ASA) collected (compared to the ED in API mass) in each stage or combinations thereof in an NGI testing apparatus of the dry powder compositions disclosed herein are at, stage 1 about 5% to about 12%, about 5% to about 10%, about 6% to about 9%, about 7% to about 8.5%, about 9.85%, about 8.54%, about 7.73%, about 7.63%, about 7.5%, about 6.79%, or about 5.89%; at stage 2 about 10% to about 25%, about 10% to about 20%, about 10% to about 17%, about 10% to about 15%, about 10% to about 12%, about 22.25%, about 21.56%, about 20.43%, about 20.06%, about 19.6%, about 17.42%, or about 16.52%; at stage 3 about 10% to about 30%, about 15% to about 25%, about 20% to about 25%, about 25.89%, about 25.79%, about 24.70%, about 23.26%, about 22.56%, about 20.63%, about 18.47%, or about 9.87%; at stage 4, about 10% to about 25%, about 15% to about 25%, about 17% to about 25%, about 20% to about 25%, about 21.30%, about 19.29%, about 18.8%, about 17.47%, about 17.17%, or about 12.77%; at stage 5 about 5% to about 10%, about 9.74%, about 9.39%, about 8.63%, about 7.98%, about 7.73%, about 7.22%, or about 4.86%; at stages 2-3 about 20% to about 50%, about 30% to about 50%, about 35% to about 50%, about 40% to about 50%, about 45% to about 50%, about 48.04%, about 44.82%, about 44.76%, about 43.30%, about 42.99%, about 40.14%, about 34.99%, or about 19.96%; at stages 4-6 about 10% to about 35%, about 20% to about 35%, about 20% to about 30%, about 25% to about 30%, about 32.11%, about 31.92%, about 31.39%, about 27.93%, about 27.25%, about 26.31%, about 18.93%, or about 10.15%; and at stages 7-8 about 1% to about 20%, about 1% to about 10%, about 1% to about 5%, about 1% to about 3%, about 16.9%, about 1.64%, about 1.49%, about 1.46%, about 1.29%, about 1.21%, or about 0.88%; and fine particle fraction (FPF) ranges from about 30% to about 50%, about 35% to about 45%, about 40% to about 45%, about 43.63%, about 39.51%, about 39.17%, about 37.55%, about 35.21%, about 33.83%, or about 32.67%. Ranges between 90%-110% or 80%420% of actual percentages set forth above are encompassed within each embodiment.

Tap density is a measure of the envelope mass density characterizing a particle. The envelope mass density of a particle of a statistically isotropic shape is defined as the mass of the particle divided by the minimum sphere envelope volume within which it can be enclosed. Features which can contribute to low tap density include irregular surface texture and porous structure. Tap density can be measured by using instruments known to those skilled in the art such as the Dual Platform Microprocessor Controlled Tap Density Tester (Vankel, N.C.), a GeoPyc™ instrument (Micrometries Instrument Corp., Norcross, Ga.), or SOTAX Tap Density Tester model TD2 (SOTAX Corp., Horsham, Pa.). Tap density can be determined using the method of USP Bulk Density and Tapped Density, United States Pharmacopia convention, Rockville, Md., $10^{th}$ Supplement, 4950-4951, 1999.

Fine particle fraction (FPF) can be used as one way to characterize the aerosol performance of a dispersed powder. Fine particle fraction describes the size distribution of airborne respirable dry particles. Gravimetric analysis, using a Cascade impactor, is one method of measuring the size distribution, or fine particle fraction, of airborne respirable dry particles. The Andersen Cascade Impactor (ACI) is an eight-stage impactor that can separate aerosols into nine distinct fractions based on aerodynamic size. The size cutoffs of each stage are dependent upon the flow rate at which the ACI is operated. The ACI is made up of multiple stages consisting of a series of nozzles (i.e., a jet plate) and an impaction surface (i.e., an impaction disc). At each stage an aerosol stream passes through the nozzles and impinges upon the surface. Respirable dry particles in the aerosol stream with a large enough inertia will impact upon the plate. Smaller respirable dry particles that do not have enough inertia to impact on the plate will remain in the aerosol stream and be carried to the next stage. Each successive stage of the ACI has a higher aerosol velocity in the nozzles so that smaller respirable dry particles can be collected at each successive stage.

The subject technology also relates to a respirable dry powder or respirable dry particles produced using any of the methods described herein.

The dry particles or dry powder compositions disclosed herein can also be characterized by the chemical stability of the salts or the excipients that the dry particles comprise. The chemical stability of the constituent salts can affect important characteristics of the particles including shelf-life, proper storage conditions, acceptable environments for administration, biological compatibility, and effectiveness of the salts. Chemical stability can be assessed using techniques well known in the art. One example of a technique that can be used to assess chemical stability is reverse phase high performance liquid chromatography (RP-HPLC).

If desired, the dry particles and dry powder compositions described herein can be further processed to increase stability. An important characteristic of pharmaceutical dry powders is whether they are stable at different temperature and humidity conditions. Unstable powders will absorb moisture from the environment and agglomerate, thus altering particle size distribution of the powder.

Excipients, such as maltodextrin, may be used to create more stable particles and powders. The maltodextrin may act as an amorphous phase stabilizer and inhibit the components from converting from an amorphous to crystalline state. Alternatively, a post-processing step to help the particles through the crystallization process in a controlled way (e.g., on the baghouse at elevated humidity) can be employed with the resultant powder potentially being further processed to restore their dispersibility if agglomerates formed during the crystallization process, such as by passing the particles through a cyclone to break apart the agglomerates. Another possible approach is to optimize around process conditions that lead to manufacturing particles that are more crystalline and therefore more stable. Another approach is to use different excipients, or different levels of current excipients to attempt to manufacture more stable forms of the salts.

The respirable dry particles and dry powders described herein are suitable for inhalation therapies. The respirable dry particles may be fabricated with the appropriate material, surface roughness, diameter, and tap density for localized delivery to selected regions of the respiratory system such as the deep lung or upper or central airways. For example, higher density or larger respirable dry particles may be used for upper airway delivery, or a mixture of varying size respirable dry particles in a sample, provided with the same or a different formulation, may be administered to target different regions of the lung in one administration.

In order to relate the dispersion of powder at different inhalation flow rates, volumes, and from inhalers of different resistances, the energy required to perform the inhalation maneuver can be calculated. Inhalation energy can be calculated from the equation $E=R^2Q^2V$ where E is the inhalation energy in Joules, R is the inhaler resistance in $kPa^{1/2}/LPM$, Q is the steady flow rate in L/min and V is the inhaled air volume in L.

Healthy adult populations are predicted to be able to achieve inhalation energies ranging from 2.9 to 22 Joules by using values of peak inspiratory flow rate (PIFR) measured by Clarke et al. (Journal of Aerosol Med, 6(2), p. 99-110, 1993) for the flow rate Q from two inhaler resistances of 0.02 and 0.055 kPa½/LPM, with a inhalation volume of 2 L based on both FDA guidance documents for dry powder inhalers and on the work of Tiddens et al. (Journal of Aerosol Med, 19, (4), p. 456-465, 2006) who found adults averaging 2.2 L inhaled volume through a variety of DPIs.

7. Methods of Treatment

In other aspects, the subject technology is a method for treating (including prophylactic treatment or reducing the risk) of a cardiovascular disease (such as thrombosis), comprising administering to the respiratory tract of a subject in need thereof an effective amount of the dry particles or dry powder compositions described herein. In certain embodiments, the dry particles or dry powder compositions disclosed herein are delivered by the DPI or MDI as disclosed herein. In certain embodiment, the dry particles or dry powder compositions disclosed herein are delivered by actuating a dry delivery system comprising the DPI or MDI as disclosed herein and the dry particles or dry powder compositions disclosed herein.

Cardiovascular diseases include, for example, atherosclerosis, coronary artery disease (CAD), angina pectoris (commonly known as "angina"), thrombosis, ischemic heart disease, coronary insufficiency, peripheral vascular disease, myocardial infarction, cerebrovascular disease (such as stroke), transient ischemic attack, arteriolosclerosis, small vessel disease, elevated cholesterol, intermittent claudication or hypertension.

The respirable dry particles and dry powder compositions disclosed herein can be administered to the respiratory tract of a subject in need thereof using any suitable method, such as instillation techniques, and/or an inhalation device, such as a dry powder inhaler (DPI) or metered dose inhaler (MDI). A number of DPIs are available, such as, the inhalers disclosed is U.S. Pat. Nos. 4,995,385 and 4,069,819, Spinhaler® (Fisons, Loughborough, U.K.), Rotahalers®, Diskhaler® and Diskus® (GlaxoSmithKline, Research Triangle Technology Park, N.C.), Ellipta™, Handihaler®, Flow-Capss®, Neohaler®, Pressair™, Rotahaler®, Turbuhaler®, Twisthaler®, XCaps (Hovione, Loures, Portugal), Inhalators® (BoehringerIngelheim, Germany), Aerolizer® (Novartis, Switzerland), CDMHaler, Podhaler™, and others known to those skilled in the art.

Generally, inhalation devices (e.g., DPIs) are able to deliver a maximum amount of dry powder or dry particles in a single inhalation, which is related to the capacity of the blisters, capsules (e.g. size 000, 00, OE, 0, 1, 2, 3, and 4, with respective volumetric capacities of 1.37 ml, 950 μl, 770 μl, 680 μl, 480 μl, 360 μl, 270 μl, and 200 μl) or other means that contain the dry particles or dry powders within the inhaler. Accordingly, delivery of a desired dose or effective amount may require two or more inhalations. Preferably, each dose that is administered to a subject in need thereof contains an effective amount of respirable dry particles or dry powder and is administered using no more than about 4 inhalations. For example, each dose of respirable dry particles or dry powder can be administered in a single inhalation or 2, 3, or 4 inhalations. The respirable dry particles and dry powders are preferably administered in a single, breath-activated step using a breath-activated DPI. When this type of device is used, the energy of the subject's inhalation both disperses the respirable dry particles and draws them into the respiratory tract.

The respirable dry particles or dry powders can be delivered by inhalation to a desired area within the respiratory tract, as desired. It is well known that particles with an MMAD of about 1 μm to about 3 μm, can be effectively delivered to the deep lung regions such as the alveolar spaces. Larger aerodynamic diameters, for example, from about 3 μm to about 5 μm can be delivered to the central and upper airways.

For dry powder inhalers, oral cavity deposition is dominated by inertial impaction and so characterized by the aerosol's Stokes number (DeHaan et al. Journal of Aerosol Science, 35 (3), 309-331, 2003). For equivalent inhaler geometry, breathing pattern and oral cavity geometry, the Stokes number, and so the oral cavity deposition, is primarily affected by the aerodynamic size of the inhaled powder. Hence, factors that contribute to oral deposition of a powder include the size distribution of the individual particles and the dispersibility of the powder. If the MMAD of the individual particles is too large, e.g. above 5 μm, then an increasing percentage of powder will deposit in the oral cavity. Likewise, if a powder has poor dispersibility, it is an indication that the particles will leave the dry powder inhaler and enter the oral cavity as agglomerates. Agglomerated powder will perform aerodynamically like an individual particle as large as the agglomerate, therefore even if the individual particles are small (e.g., MMAD of about 5 μm or less), the size distribution of the inhaled powder may have an MMAD of greater than about 5 μm, leading to enhanced oral cavity deposition.

Certain embodiments provide a powder in which the particles are small (e.g., MMAD of 5 μm or less, e.g. between about 1 μm to 5 μm), and are highly dispersible (e.g. ¼ bar or alternatively, 0.5/4 bar of 2.0, and preferably less than 1.5). The respirable dry powder may be comprised of respirable dry particles with an MMAD between 1 to 4 μm or 1 to 3 μm, and have a ¼ bar less than 1.4, or less than 1.3, and more preferably less than 1.2.

The absolute geometric diameter of the particles measured at 1 bar using the HELOS system is not critical provided that the particle's envelope density is sufficient such that the MMAD is in one of the ranges listed above, wherein MMAD is VMGD times the square root of the envelope density (MMAD=VMGD*sqrt (envelope density)). If it is desired to deliver a high unit dose of salt using a fixed volume-dosing container, then, particles of higher envelop density are desired. High envelope density allows for more mass of powder to be contained within the fixed volume-dosing container. Preferable envelope densities are greater than 0.1 g/cm$^3$, greater than 0.25 g/cm$^3$, greater than 0.4 g/cm$^3$, greater than 0.5 g/cm$^3$, and greater than 0.6 g/cm$^3$.

The dry powder compositions disclosed herein can be employed in compositions suitable for drug delivery via the respiratory system. For example, such compositions can include blends of the respirable dry particles of the subject technology and one or more other dry particles or powders, such as dry particles or dry powder compositions that contain another active agent, or that consist of or consist essentially of one or more pharmaceutically acceptable excipients.

The dry powder compositions disclosed herein suitable for the methods disclosed herein can travel through the upper airways (i.e., the oropharynx and larynx), the lower airways, which include the trachea followed by bifurcations into the bronchi and bronchioli, and through the terminal bronchioli which in turn divide into respiratory bronchiole leading then to the ultimate respiratory zone, the alveoli or the deep lung. In one embodiment of the subject technology, most of the mass of respirable dry powders or particles deposit in the deep lung. In another embodiment of the subject technology, delivery is primarily to the central airways. In another embodiment, delivery is to the upper airways.

The dry powder compositions disclosed herein can be delivered by inhalation at various parts of the breathing cycle (e.g., laminar flow at mid-breath). An advantage of the high dispersibility of the dry powder compositions disclosed herein is the ability to target deposition in the respiratory tract. For example, breath controlled delivery of nebulized solutions is a recent development in liquid aerosol delivery (Dalby et al. in Inhalation Aerosols, edited by Hickey 2007, p. 437). In this case, nebulized droplets are released only during certain portions of the breathing cycle. For deep lung delivery, droplets are released in the beginning of the inhalation cycle, while for central airway deposition, they are released later in the inhalation.

The dry powder compositions disclosed herein provide advantages for targeting the timing of drug delivery in the breathing cycle and also location in the human lung. Because dry powder compositions disclosed herein can be dispersed rapidly, such as within a fraction of a typical inhalation maneuver, the timing of the powder dispersal can be controlled to deliver an aerosol at specific times within the inhalation.

With a highly dispersible powder, the complete dose of aerosol can be dispersed at the beginning portion of the inhalation. While the patient's inhalation flow rate ramps up to the peak inspiratory flow rate, a highly dispersible powder will begin to disperse already at the beginning of the ramp up and could completely disperse a dose in the first portion of the inhalation. Since the air that is inhaled at the beginning of the inhalation will ventilate deepest into the lungs, dispersing the most aerosol into the first part of the inhalation is preferable for deep lung deposition. Similarly, for central deposition, dispersing the aerosol at a high concentration into the air which will ventilate the central airways can be achieved by rapid dispersion of the dose near the mid to end of the inhalation. This can be accomplished by a number of mechanical and other means such as a switch operated by time, pressure or flow rate that diverts the patient's inhaled air to the powder to be dispersed only after the switch conditions are met.

Aerosol dosage, formulations and delivery systems may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6: 273-313 (1990); and in Moren, "Aerosol Dosage Forms and Formulations," in Aerosols in Medicine, Principles, Diagnosis and Therapy, Moren, et al., Eds., Esevier, Amsterdam (1985).

Suitable intervals between doses that provide the desired therapeutic effect can be determined based on the severity of the condition, overall well-being of the subject and the subject's tolerance to respirable dry particles and dry powders and other considerations. Based on these and other considerations, a clinician can determine appropriate intervals between doses. Respirable dry particles and dry powders may be administered once, twice or three times a day or on an as needed basis.

In various embodiments, the amount of API (e.g., NSAID, such as acetylsalicyclic acid), delivered to the respiratory tract (e.g., lungs, respiratory airway) is about 0.001 mg/kg body weight/dose to about 2 mg/kg body weight/dose, about 0.002 mg/kg body weight/dose to about 2 mg/kg body weight/dose, about 0.005 mg/kg body weight/dose to about 2 mg/kg body weight/dose, about 0.01 mg/kg body weight/dose to about 2 mg/kg body weight/dose, about 0.02 mg/kg body weight/dose to about 2 mg/kg body weight/dose, about 0.05 mg/kg body weight/dose to about 2 mg/kg body weight/dose, about 0.075 mg/kg body weight/dose to about 2 mg/kg body weight/dose, about 0.1 mg/kg body weight/dose to about 2 mg/kg body weight/dose, about 0.2 mg/kg body weight/dose to about 2 mg/kg body weight/dose, about 0.5 mg/kg body weight/dose to about 2 mg/kg body weight/dose, or about 0.75 mg/kg body weight/dose to about 2 mg/kg body weight/dose.

In certain embodiments, at least about 50%, at least about 60%, at least about 70%, at least about 75%, at least about 80%, at least about 85%, at least about 90%, at least about 95%, or at least about 99%, of the administered API (e.g., NSAIDs such as acetylsalicyclic acid) reaches the systemic circulation of a subject within about 60 minutes upon administration, or within about 40 minutes upon administration, or within about 30 minutes upon administration, or within about 20 minutes upon administration, or within about 15 minutes upon administration, or within about 5 minutes upon administration.

The dosing of API (e.g., NSAID such as acetylsalicyclic acid) may be adjusted so that PGI2 synthesis capacity of the nasal, bronchial or pulmonary epithelial of endothelial cells, including nasal mucosa cells, is not inhibited.

In certain embodiments, the method and delivery devices described herein can deliver acetylsalicylic acid, and pharmacologically active metabolic byproducts of acetylsalicylic acid thereof, to the systemic circulation, at levels that are substantially the same, or higher as compared to those delivered by oral administration of about 30 mg of acetylsalicylic acid, about 40 mg of acetylsalicylic acid, about 50 mg of acetylsalicylic acid, about 80 mg of acetylsalicylic acid or about 160 mg of acetylsalicylic acid.

The doses of acetylsalicylic acid administered in order to achieve a level (or an average level among a population of patients) that is substantially the same, or higher as compared to those delivered by oral administration of about 30 mg, about 40 mg, about 50 mg, about 80 mg, or about 160 mg of acetylsalicylic acid can be determined by conventional methods. The dosing, administration techniques and schedules are known in the art and are within the ability of the skilled clinician. For example, the serum level of acetylsalicylic acid, or a metabolite thereof, in a subject (or average serum level among a population of subjects) can be determined by conventional pharmacokinetic or pharmacodynamics studies.

In certain embodiments, the method and delivery devices described herein can deliver acetylsalicylic acid to the systemic circulation such that the circulating plasma level of acetylsalicylic acid is at least about 1 µg/mL, at least about 2 µg/mL, at least about 3 µg/mL, at least about 4 µg/mL, at least about 5 µg/mL, oat least about 6 µg/mL, within about 60 minutes upon administration, or within about 40 minutes upon administration, or within about 30 minutes upon administration, or within about 20 minutes upon administration, or within about 15 minutes upon administration, or within about 5 minutes upon administration.

In other embodiments, the method and delivery devices described herein can deliver acetylsalicylic acid to the systemic circulation such that circulating plasma level of salicylate is about 8 µg/mL, about 9 µg/mL, about 10 µg/mL, about 11 µg/mL, about 12 µg/mL, or about 15 µg/mL, within about 60 minutes upon administration, or within about 40 minutes upon administration, or within about 30 minutes upon administration, or within about 20 minutes upon administration, or within about 15 minutes upon administration, or within about 5 minutes upon administration.

If desired or indicated, the respirable dry particles and dry powders described herein can be administered with one or more other therapeutic agents. The other therapeutic agents can be administered by any suitable route, such as orally, parenterally (e.g., intravenous, intraarterial, intramuscular, or subcutaneous injection), topically, by inhalation (e.g., intrabronchial, intranasal or oral inhalation, intranasal drops), rectally, vaginally, and the like. The respirable dry particles and dry powders can be administered before, substantially concurrently with, or subsequent to administration of the other therapeutic agent. Preferably, the respirable dry particles and dry powders and the other therapeutic agent are administered so as to provide substantial overlap of their pharmacologic activities.

The following examples of specific aspects for carrying out the present invention are offered for illustrative purposes only, and are not intended to limit the scope of the present invention in any way.

Example 1 Preparation of Co-Micronized ASA/MgST Dry Powder Compositions

ASA and MgST were individually dissolved into a solution, respectively. ASA and MgST were blended and co-micronized via air-jet microniser. The micronized powder was rested for 24 hours and packaged for further analysis, as described in Examples 2-4.

Example 2: ASA Remained Unexpectedly Stable in the Co-Micronized ASA Compositions with Various Concentration of MgST Prepared According to Example 1

The co-micronized ASA compositions with MgST concentration of 10.00%, 5.00%, 1.00%, 0.50%, 0.25%, 0.10%, 0.05%, and 0.01% were prepared according to the co-micronization method described in Example 1, and stored at various condition for up to 12 months. Then the co-micronized ASA/MgST compositions were analyzed by HPLC using a Phenomenex C18 column (250×4.6 mm, 5 µm) at 25° C., at flow rate of 1.0 mL/min, with injection volume of 10 µL. UV at 237 nm was used for detection. The mobile phase/diluent was prepared by adding 2 mL phosphoric acid into a mixture of 400 mL acetonitrile and 600 water. The sample was dissolved in acetonitrile and calibrated with standards to provide the assay % (w/w) of ASA in the sample by the following Equation 1:

$$\text{Assay (\% w/w)} = \frac{\text{Weight}_{std} \times \text{Area}_{samp} \times Vol_{samp} \times \text{Purity}_{std} \times 100}{\text{Area}_{std} \times \text{Volume}_{std} \times \text{weight}_{samp} \times 100} \quad \text{Equation 1}$$

wherein Std=standard, Samp=sample, Vol=Volume (mL), purity=purity of reference standard material (%).

The co-micronized ASA/MgST compositions showed unexpectedly high ASA stability in compositions with all MgST concentrations tested. It is well known that MgST is incompatible with ASA as it can further facilitate the hydrolysis of ASA. Thus, it is unexpected that the ASA in the co-micronized ASA compositions with MgST concentration remained stable after 12 months under 15-20° C./35-45% RH (Table 2).

TABLE 2

ASA showed unexpected high stability in co-micronized ASA compositions with various concentrations of MgST prepared according to Example 1 and stored at 15-20° C./35-45% RH for 12 months.

| MgSt (%) | Ave. of three runs | | |
|---|---|---|---|
| | ASA % w/w | SA % w/w | Other impurities % w/w |
| 10.00 | 98.98 | 1.30 | <0.05 |
| 5.00 | 99.41 | 0.28 | <0.05 |
| 1.00 | 101.80 | 0.40 | <0.05 |
| 0.50 | 102.62 | 0.14 | <0.05 |
| 0.25 | 101.38 | 0.17 | <0.05 |
| 0.10 | 102.81 | 0.18 | <0.05 |
| 0.05 | 103.04 | 0.18 | <0.05 |
| 0.01 | 84.84 | 0.16 | <0.05 |

Example 3: ASA Remained Unexpectedly Stable in the Co-Micronized ASA Compositions with Various Concentration of MgST Prepared According to Example 1, 8 Weeks Under 20° C./40% RH, 30° C./60% RH, and 40° C./75% RH The co-micronized ASA compositions with MgST concentration of 0.50 were prepared under 12 PPH, according to the co-micronization method described in Example 1, and stored under 20° C./40% RH, 30° C./60% RH, and 40° C./75% RH for up to 8 weeks. Then the co-micronized ASA/MgST compositions were analyzed by HPLC using a ZORBAX Eclipse Plus C18 column (3 mm×100 mm, 3.5 µm) at 25° C., at flow rate of 1.0 mL/min, with injection volume of 20 µL, and the auto-sampler temperature was 5° C. UV at 275 nm was used for detection. The mobile phase/diluent was water:methanol:TFA=72:28:0.2 (v/v). The sample was dissolved in the mobile phase/diluent and calibrated with standards to provide the assay % (w/w) of ASA in the sample using Equation 1 of Example 2.

As shown in Tables 3A and 3B, ASA remained stable and hardly degraded into SA.

TABLE 3A

ASA showed unexpected high stability in co-micronized ASA compositions with 10% MgST prepared according to Example 1 and stored under 20° C./40% RH, 30° C./60% RH, and 40° C./75% RH for up to 8 weeks.

| | Assay (%) ASA | | | | |
|---|---|---|---|---|---|
| Sample | Initial | T = 2 weeks | T = 4 weeks | T = 6 weeks | T = 8 weeks |
| 20° C./40% RH | 99.73 (0.47) | 98.25 (0.73) | 98.55 (0.33) | 97.92 (0.56) | 97.28 (0.58) |
| 30° C./60% RH | | 98.42 (0.40) | 98.19 (0.42) | 98.75 (0.35) | 97.77 (0.89) |
| 40° C./75% RH | | 97.99 (0.52.) | 98.76 (0.52) | 98.52 (0.38) | 97.42 (0.55) |

TABLE 3B

SA found in co-micronized ASA/MgST compositions with 10% MgST prepared according to Example 1 and stored under 20° C./40% RH, 30° C./60% RH, and 40° C./75% RH for up to 8 weeks.

| | Peak Area (%) SA | | | | |
|---|---|---|---|---|---|
| Sample | Initial | T = 2 weeks | T = 4 weeks | T = 6 weeks | T = 8 weeks |
| 20° C./40% RH | 1.48 | 1.52 | 1.68 | 2.39 | 2.44 |
| 30° C./60% RH | | 1.55 | 1.78 | 2.42 | 2.52 |
| 40° C./75% RH | | 1.59 | 1.82 | 2.58 | 2.82 |

Example 4. Aerodynamic Particle Size Distribution and Particle Size Distribution Stability of ASA/MgST Dry Powder Compositions A) Aerodynamic Particle Size Distribution Stability of ASA/MgST Dry Powder Compositions with Various MgST Concentrations Prepared as Described in Example 1 at 50° C./75% RH.

Aerodynamic diameter of ASA/MgST dry powder compositions prepared as described in Example 1 may be characterized by a Next Generation Impactor (NGI). The NGI consisted of seven stages and can be calibrated at flow rates of 30, 60, and 100 LPM. The stages of the NGI were all in one plane. Collection cups were used to collect the particles below each stage of the NGI. See U.S. Pat. No. 8,614,255, which is incorporated herein by reference for its entirety.

ASA/MgST formulations with MgST concentration of 0.5% w/w, 0.05% w/w, 0.01% w/w, and 0.1% w/w were filled into size 3 capsules and packaged in HDPE bottles that were then aluminium foil wrapped. Then the formulations were stored at 50° C./75% RH and characterized by NGI for their aerodynamic particle size distribution (APSD) stability profile after storage for 5, 15, and 30 days (FIGS. 2A-2D).

Figure 2A:
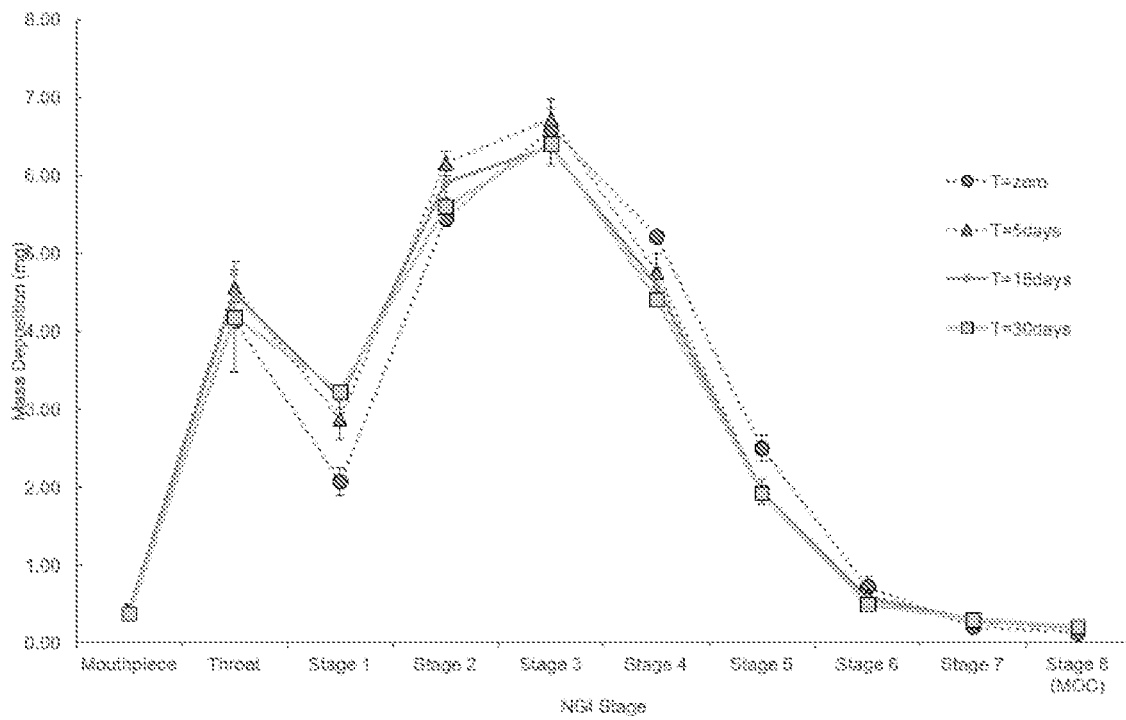
FIGS. 2A-2D: Aerodynamic particle size distribution stability profile of examples of ASA/MgST formulations with various MgST concentrations (0.01%-0.5%) at 50° C./75% RH.
Figure 2B:
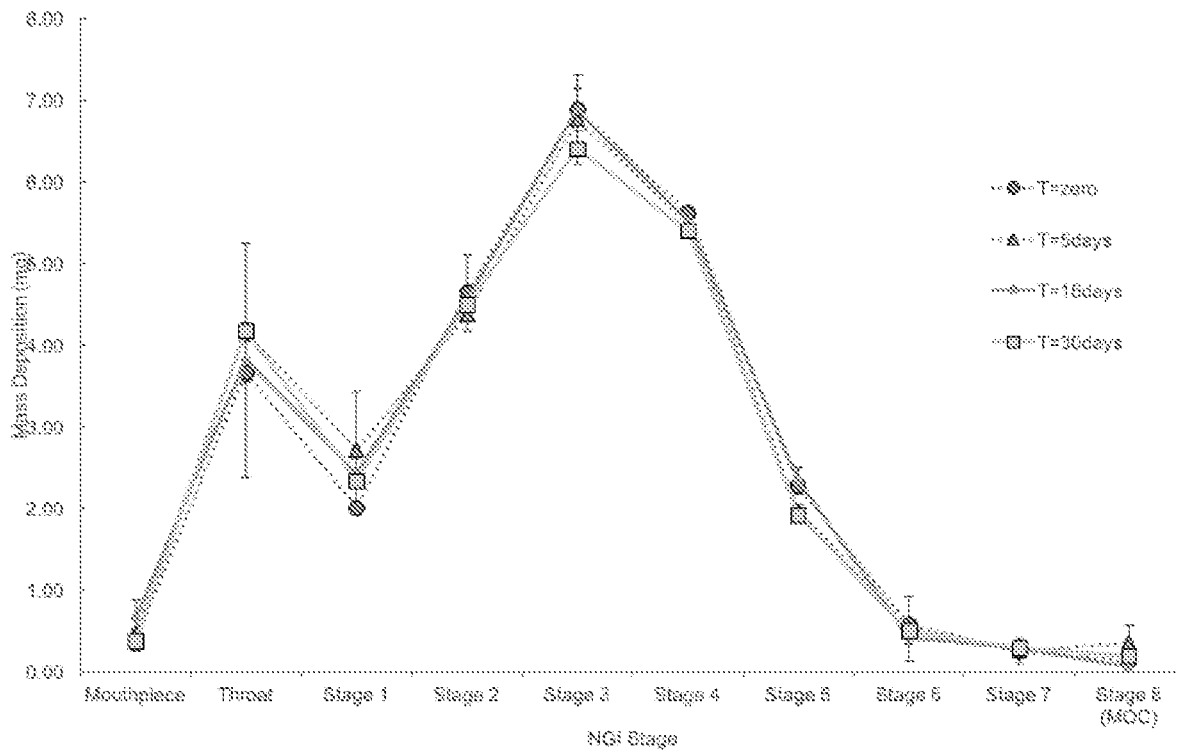
Figure 2C:
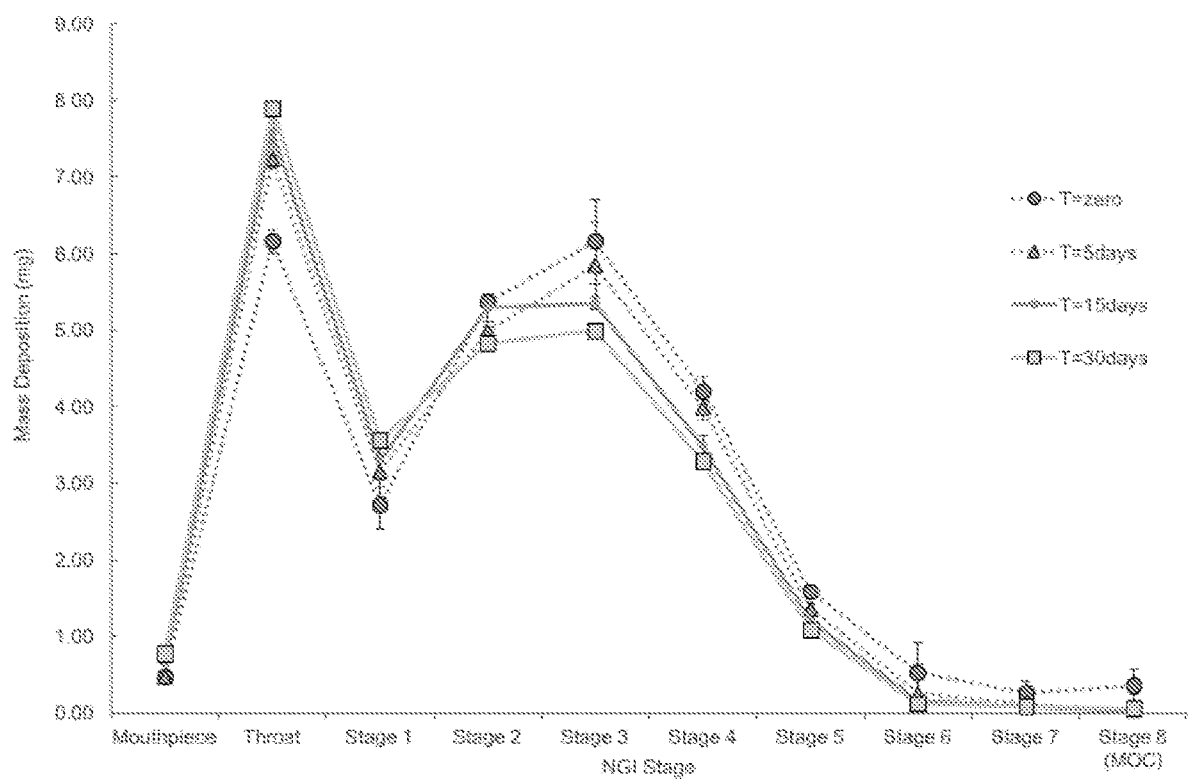
Figure 2D:
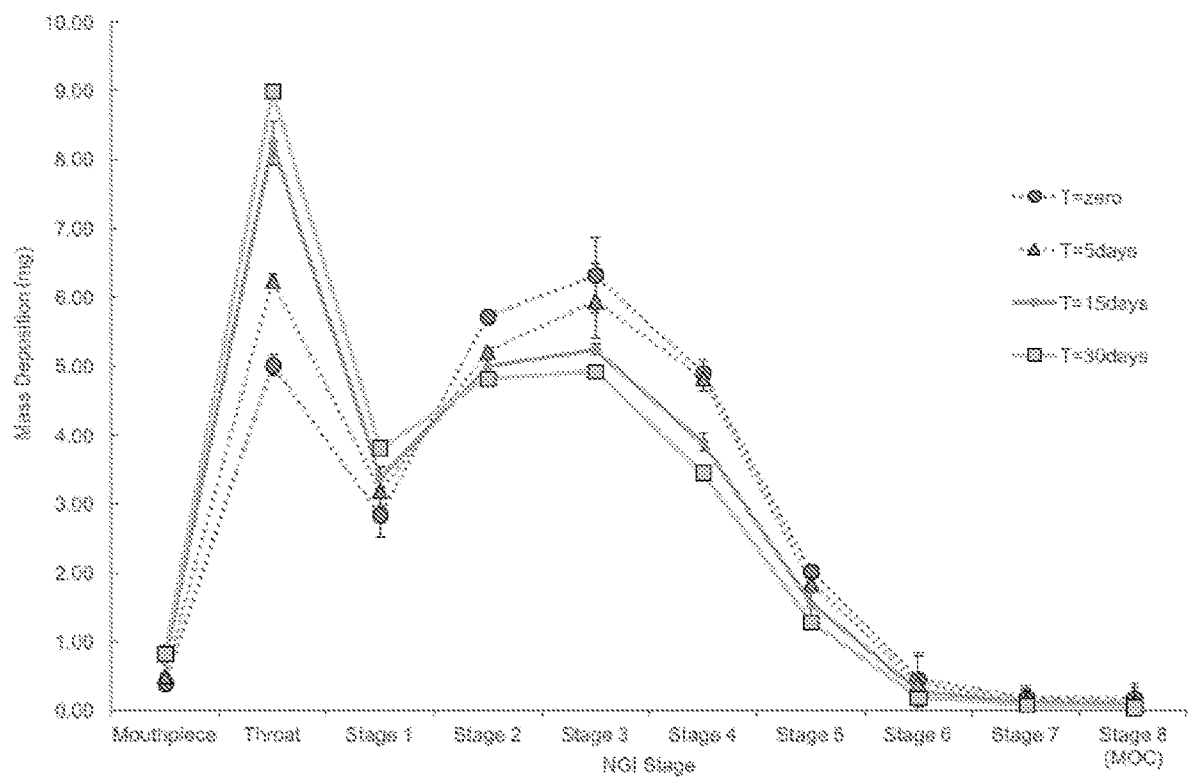

The APSD data for the 0.5% w/w and 0.05% w/w MgST/ASA compositions suggested that the respective aerodynamic particle size distribution of the formulations was stable across the stress stability time-points (FIGS. 2A-2B). In comparison, the APSD of ASA/MgST dry powder compositions containing 0.01% w/w and 0.1% w/w MgST were negatively impacted upon stress stability storage (FIGS. 2C-2D). By 15-days stress stability, the FPM of both formulations had decreased by 20% and there was a significant coarsening of the MMAD, which was indicated by the shift in the APSD.

B) Particle Size Distribution (PSD) Stability of ASA/MgST Dry Powder Compositions with 10% w/w MgST Prepared as Described in Example 1 Under 20° C./40% RH, 30° C./60% RH, and 40° C./75% RH for Up to 8 Weeks.

Particle size distribution of the ASA/MgST compositions were measured by wet dispersion using Spraytec along with the Wet Dispersion Unit (Malvern Instruments, Malvern, UK) (Table 3C). Mie and Fraunhofer scattering were analysed. Data were acquired at 10$k$ Hz for the rapid mode, and at 1 Hz for the continuous mode, and the maximum measurement time was 30 seconds for the rapid mode and 60 minutes for the continuous mode. The internal measurement triggering was based on transmission or light scattering levels; and the external measurement triggering was based on TTL input or simple switch trigger. Light source was Max 4 mW He—Ne laser at 632.8 nm. The lens arrangement was fourier (parallel beam) and the lens forcal length was 300 mm and 750 mm. The measurement range was 150 mm at 0.5 µm, extending to greater than 1 m above 5 µm. 300 mm lens was for size 0.1-900 µm (DV50:0.5-600 µm), and 750 mm lens was for size 2-2,000 µm (DV50:5-1600 µm). The software SOP was for wet cell measurement: 300 mm lens, timed measure/1 s, sampling period/15 sec. The measurement for background took 15 second. ASA refractive index was 1.57±0.10, density was 1.00, and the refractive Index for cyclohexane was 1.43 Detector range was 1-Last, and the scattering threshold was 1. Stirrer/pump was at 3,000 rpm, obscuration was 5-15%, and internal sonication time was 1 min. About 100 mL of dispersant was added in circulation with the pump at 3,000 rpm. The unit was switched off for a brief period to allow trapped air to rise out of the system. The light energy was below 100 and the laser intensity was between 70-95%. Sample (about 10.0±1 mg powder) was dispersed in around 4 mL of cyclohexane by internal ultra-sonication for 1 min. Then the sample was added to the system until obscuration level was between 5-15% for measurements.

Figure 3:
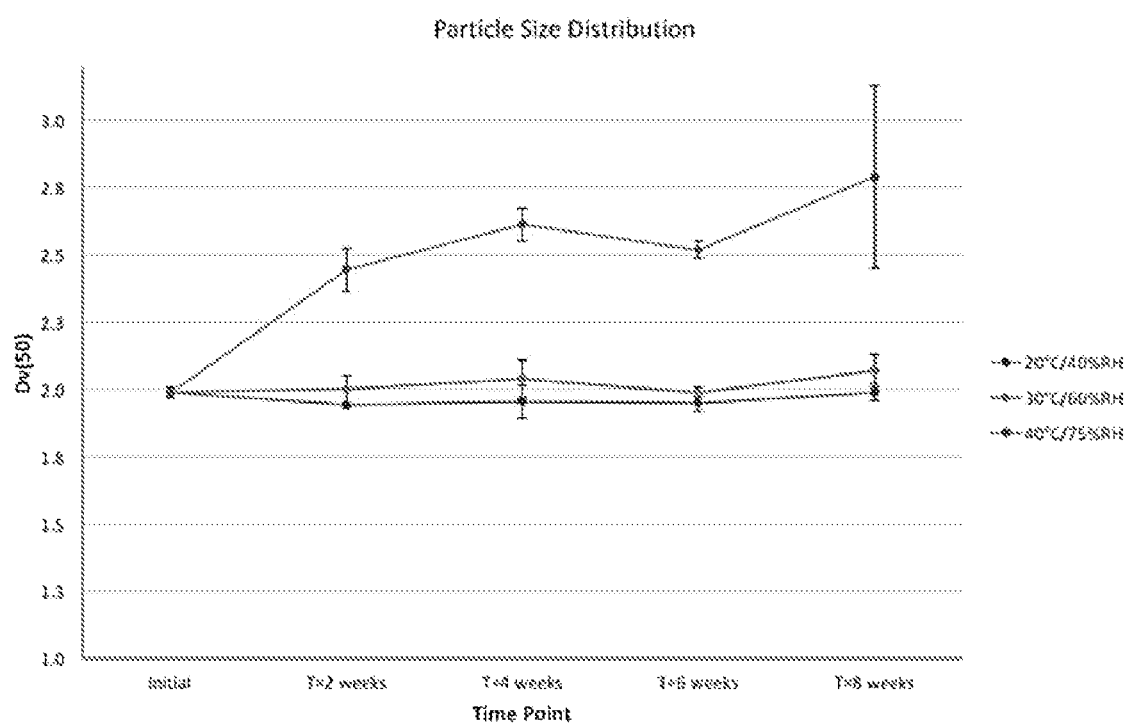
FIG. 3: PSD (Dv50) stability profile of an example of ASA/MgST 10.0% w/w Formulation under 20° C./40% RH, 30° C./60% RH, and 40° C./75% RH.

The results showed that the PSD of the ASA/MgST dry powder composition having 10% MgST remained relatively stable at under 20° C./40% RH and 30° C./60% RH, while the particle sizes increased after storage under 40° C./75% RH for a long timer (FIG. 3).

TABLE 4

PSD of co-micronized ASA/MgST compositions with 10% MgST prepared according to Example 1
and stored under 20° C./40% RH, 30° C./60% RH, and 40° C./75% RH for up to 8 weeks.
PSD BY WET DISPERSION

| BATCH NUMBER | T (W) | DV(10)/ μM | DV(50)/ μM | DV(90)/ μM | DV(99)/ μM | % V < 1 μM/% | % V < 3 μM/% | % V < 5 μM/% | OBS (%) |
|---|---|---|---|---|---|---|---|---|---|
| 20°/40% | 0 | 1.04 | 1.99 | 3.79 | 5.77 | 8.40 (0.35) | 78.70 | 97.30 | 9.57 |
|  |  | (0.01) | (0.02) | (0.06) | (0.12) |  | (0.75) | (0.29) | (1.18) |
|  | 2 | 1.04 | 1.94 | 3.62 | 5.44 | 8.57 (0.18) | 80.87 | 98.10 | 7.25 |
|  |  | (0.00) | (0.00) | (0.03) | (0.08) |  | (0.38) | (0.18) | (1.48) |
|  | 4 | 1.01 | 1.96 | 3.75 | 5.71 | 9.55 (1.06) | 79.45 | 97.44 | 13.66 |
|  |  | (0.03) | (0.06) | (0.12) | (0.15) |  | (1.80) | (0.46) | (1.89) |
|  | 6 | 1.01 | 1.95 | 3.76 | 5.91 | 9.54 (0.46) | 79.6 | 97.23 | 10.76 |
|  |  | (0.01) | (0.03) | (0.17) | (0.64) |  | (1.73) | (1.12) | (2.1) |
|  | 8 | 1.04 | 1.99 | 3.78 | 5.75 | 8.52 (0.29) | 78.86 | 97.34 | 11.35 |
|  |  | (0.01) | (0.03) | (0.08) | (0.16) |  | (1.09) | (0.4) | (1.85) |
| 30°/60% | 0 | 1.04 | 1.99 | 3.79 | 5.77 | 8.40 (0.35) | 78.70 | 97.30 | 9.57 |
|  |  | (0.01) | (0.02) | (0.06) | (0.12) |  | (0.75) | (0.29) | (1.18) |
|  | 2 | 1.06 | 2.00 | 3.79 | 5.76 | 7.92 (0.58) | 78.60 | 97.30 | 9.27 |
|  |  | (0.02) | (0.05) | (0.12) | (0.21) |  | (1.68) | (0.58) | (0.21) |
|  | 4 | 1.05 | 2.04 | 4.00 | 9.42 | 8.15 (1.07) | 76.48 | 95.91 | 11.24 |
|  |  | (0.03) | (0.07) | (0.21) | (5.49) |  | (2.53) | (1.28) | (0.51) |
|  | 6 | 1.05 | 1.99 | 3.77 | 5.75 | 8.28 (0.47) | 78.93 | 97.36 | 10.35 |
|  |  | (0.01) | (0.02) | (0.04) | (0.06) |  | (0.61) | (0.18) | (0.73) |
|  | 8 | 1.08 | 2.07 | 3.96 | 6.04 | 7.22 (0.41) | 76.26 | 96.46 | 9.31 |
|  |  | (0.01) | (0.06) | (0.2) | (0.4) |  | (2.47) | (1.14) | (1.17) |
| 40°/75% | 0 | 1.04 | 1.99 | 3.79 | 5.77 | 8.40 (0.35) | 78.70 | 97.30 | 9.57 |
|  |  | (0.01) | (0.02) | (0.06) | (0.12) |  | (0.75) | (0.29) | (1.18) |
|  | 2 | 1.15 | 2.45 | 5.47 | 14.77 | 5.85 (0.45) | 62.88 | 87.30 | 2.33 |
|  |  | (0.02) | (0.08) | (0.45) | (8.17) |  | (2.62) | (2.56) | (0.32) |
|  | 4 | 1.21 | 2.61 | 5.71 | 10.84 | 4.71 (0.30) | 58.75 | 85.45 | 5.41 |
|  |  | (0.02) | (0.06) | (0.23) | (1.31) |  | (1.61) | (1.39) | (1.82) |
|  | 6 | 1.23 | 2.52 | 5.13 | 8.2 | 3.98 (0.14) | 61.99 | 89.08 | 4.86 |
|  |  | (0.01) | (0.03) | (0.12) | (0.34) |  | (0.98) | (0.85) | (0.63) |
|  | 8 | 1.23 | 2.79 | 6.06 | 10.76 | 4.78 (0.78) | 55.36 | 82.93 | 3.26 |
|  |  | (0.04) | (0.34) | (1.08) | (2.43) |  | (8.16) | (7.23) | (1.97) |

Example 5: Aerodynamic Particle Size Distribution (APSD) of ASA/MgST Dry Powder Compositions Prepared as Described in Example 1

Figure 4A:
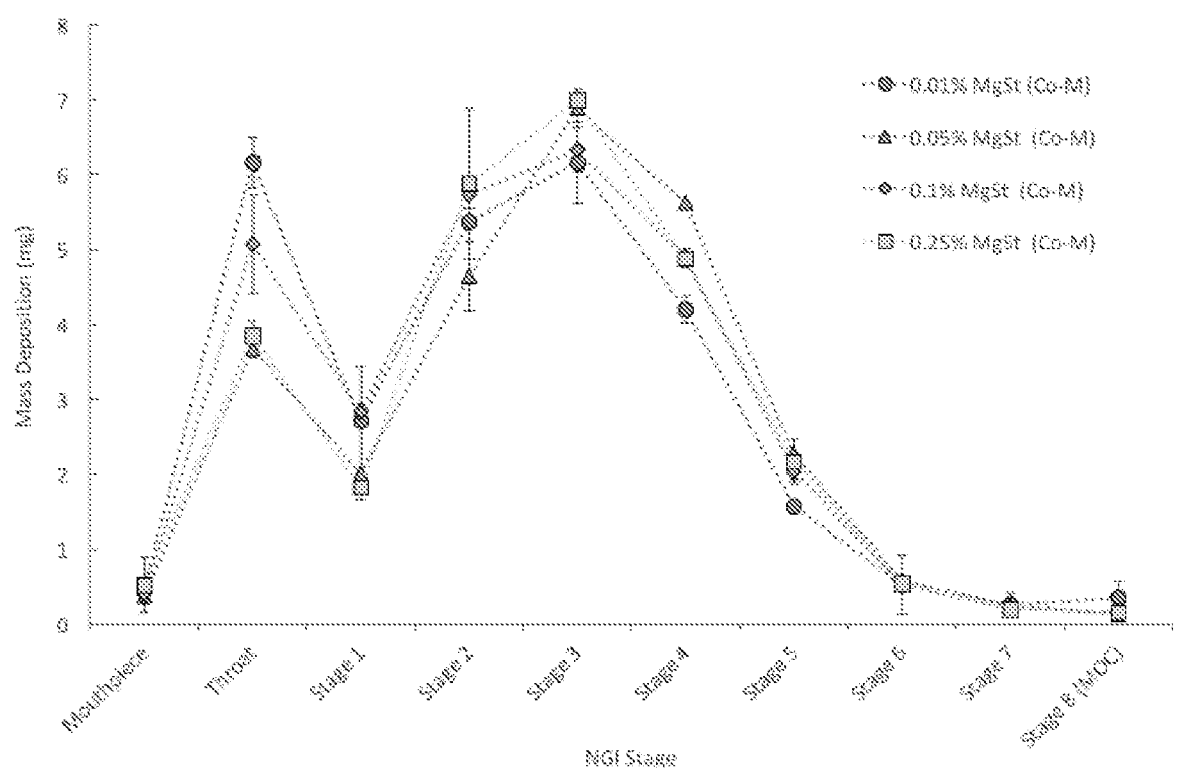
FIGS. 4A-4D: Aerodynamic particle size distribution (APSD) performance of examples of co-micronized ASA with different concentrations (0.01-10% w/w) of MgST (Co-M)
Figure 4B:
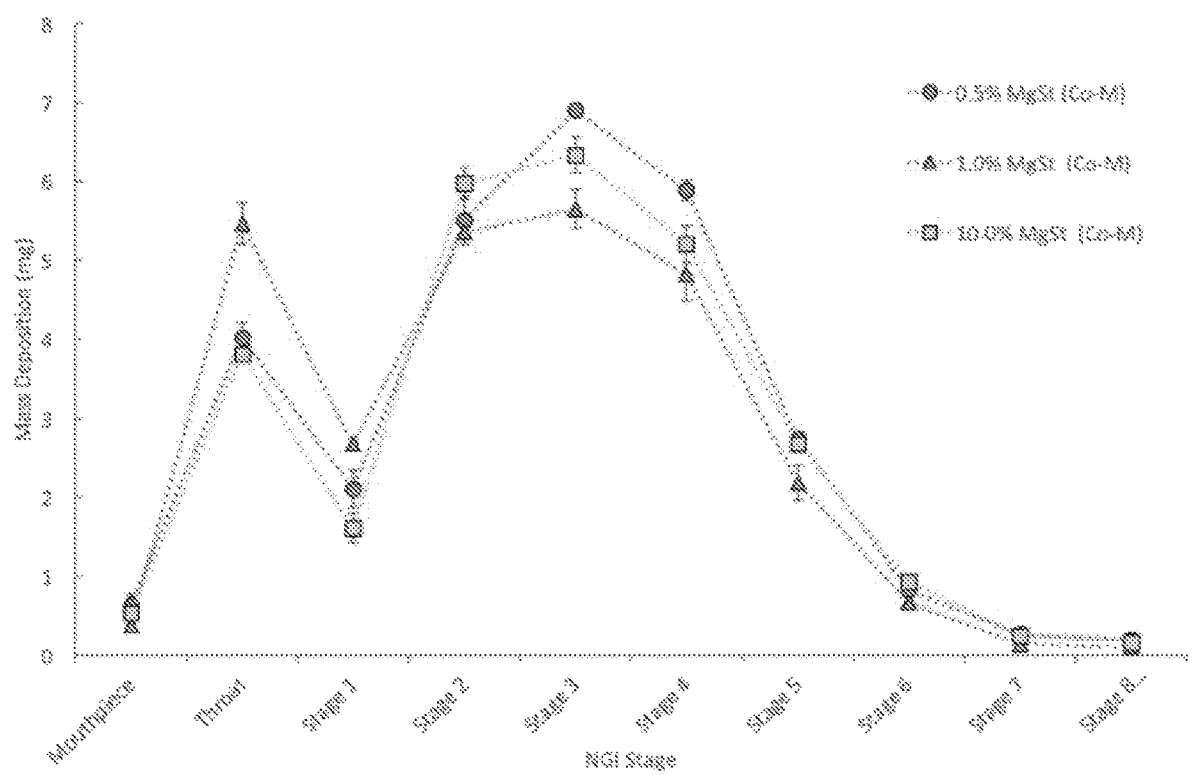
Figure 4C:
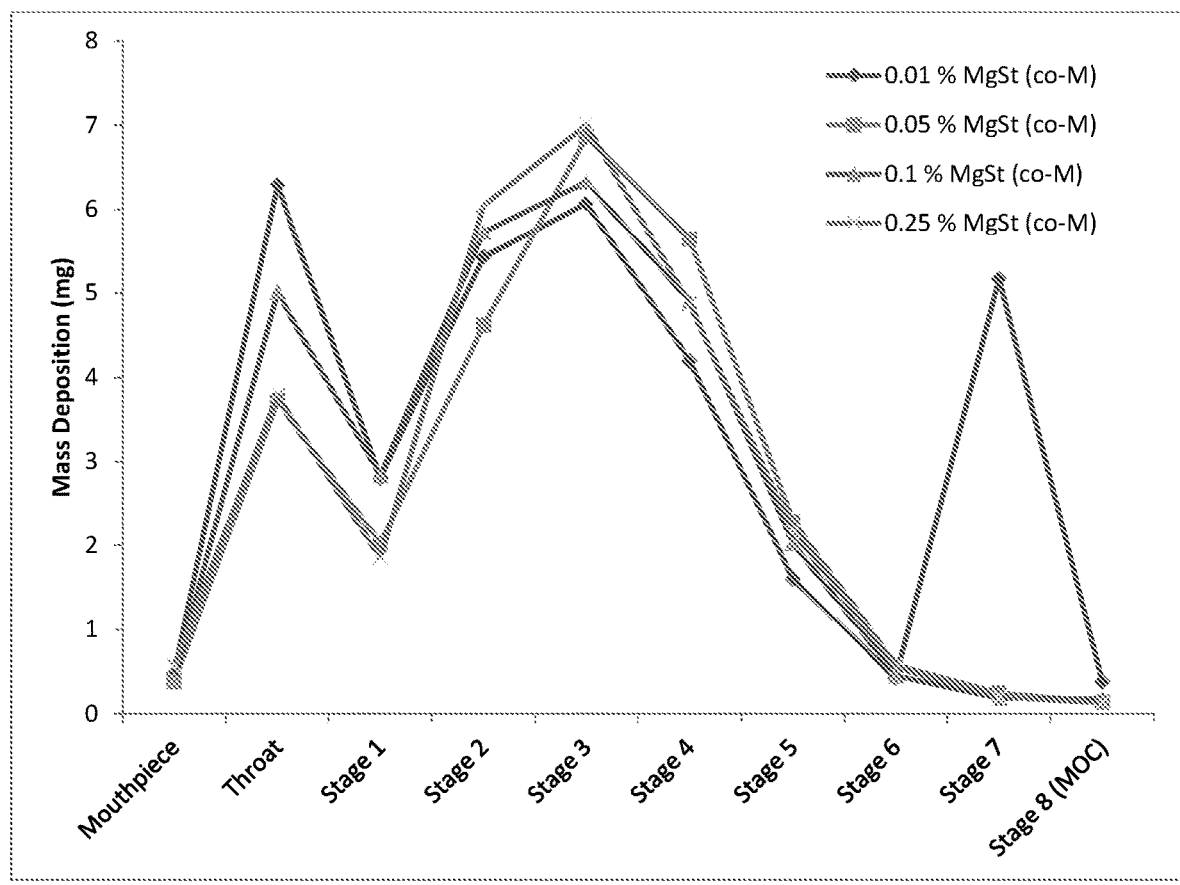
Figure 4D:
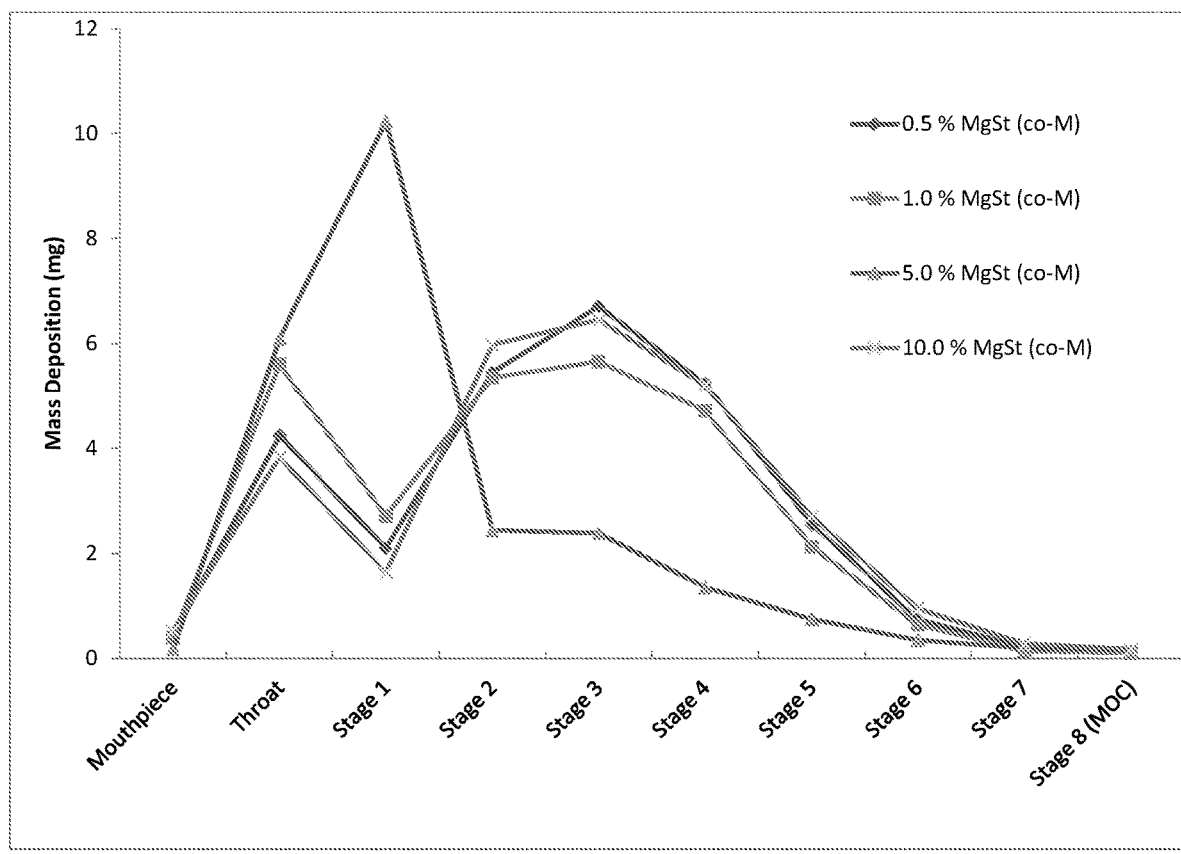

APSD of ASA/MgST dry powder concentrations with various MgST concentrations were characterized by the Next Generation Impactor (NGI). The NGI consisted of seven stages and can be calibrated at flow rates of 30, 60, and 100 LPM. The stages of the NGI were all in one plane. Collection cups were used to collect the particles below each stage of the NGI. See U.S. Pat. No. 8,614,255, which is incorporated herein by reference for its entirety. The results were shown in average from three runs of NGI measurements on each ASA/MgSt dry powder composition (FIGS. 4A and 4B and Tables 5A-5B showing NGI results of a first batch of the dry powder compositions prepared as described in Example 1, and FIGS. 4C and 4D and Tables 5C and 5D showing NGI results of a second batch of the dry powder compositions prepared as described in Example 1).

TABLE 5A

APSD of ASA/MgST dry powder composition with 0.01%, 0.05% 0.1% and 0.25% w/w MgST

| MgST % | 0.01: Ave. (SD) | 0.05: Ave. (SD) | 0.1: Ave. (SD) | 0.25: Ave. (SD) |
|---|---|---|---|---|
| ED(μg) | 27.79 (2.00) | 26.45 (0.98) | 28.19 (0.04) | 27.03 (1.64) |
| MMAD (μm) | 3.02 (0.14) | 2.67 (0.05) | 3.40 (0.32) | 3.27 (0.18) |
| GSD | 1.96 (0.13) | 1.89 (0.03) | 1.98 (0.024) | 1.79 (0.04) |
| FPM(mg) | 13.17 (0.99) | 15.75 (0.27) | 14.16 (0.61) | 14.95 (0.11) |
| FPF(%) | 32.69 (7.08) | 39.42 (0.96) | 35.49 (2.13) | 37.61 (3.11) |

TABLE 5B

APSD of ASA/MgST dry powder composition with 0.5%, 1.0%, and 10.0% w/w MgST

| MgST % | 0.5: Ave. (SD) | 1.0: Ave. (SD) | 10.0: Ave. (SD) |
|---|---|---|---|
| ED(μg) | 29.09 (0.33) | 27.45 (0.61) | 27.51 (0.02) |
| MMAD (μm) | 2.67 (0.07) | 2.90 (0.07) | 3.02 (0.38) |
| GSD | 1.90 (0.01) | 2.00 (0.00) | 1.83 (0.01) |
| FPM(mg) | 16.81 (0.17) | 13.57 (0.84) | 15.57 (0.45) |
| FPF(%) | 42.24 (0.98) | 34.26 (1.94) | 43.24 (1.65) |

TABLE 5C

APSD of ASA/MgST dry powder composition with 0.01%, 0.05% 0.1% and 0.25% w/w MgST

| | MgST % | | | | | | | | | | | |
|---|---|---|---|---|---|---|---|---|---|---|---|---|
| | 0.01 | | | 0.05 | | | 0.1 | | | 0.25 | | |
| NGI Stage | Ave | RSD | SD | Ave | RSD | SD | Ave | RSD | SD | Ave | RSD | SD |
| Mouthpiece | 0.49 | 7.20 | 0.03 | 0.38 | 21.59 | 0.08 | 0.40 | 0.78 | 0.00 | 0.57 | 48.70 | 0.28 |
| Throat | 6.29 | 26.02 | 1.64 | 3.72 | 3.19 | 0.12 | 5.01 | 9.51 | 0.48 | 3.79 | 4.63 | 0.18 |
| Stage 1 | 2.81 | 18.95 | 0.53 | 2.02 | 1.18 | 0.02 | 2.84 | 2.60 | 0.07 | 1.85 | 6.70 | 0.12 |
| Stage 2 | 5.43 | 2.05 | 0.11 | 4.62 | 7.19 | 0.33 | 5.73 | 2.32 | 0.13 | 6.04 | 12.63 | 0.76 |
| Stage 3 | 6.07 | 6.89 | 0.42 | 6.86 | 2.74 | 0.19 | 6.33 | 3.31 | 0.21 | 7.01 | 1.26 | 0.09 |
| Stage 4 | 4.20 | 3.03 | 0.13 | 5.65 | 0.68 | 0.04 | 4.90 | 0.67 | 0.03 | 4.87 | 1.88 | 0.09 |
| Stage 5 | 1.60 | 3.93 | 0.06 | 2.29 | 0.85 | 0.02 | 2.02 | 3.71 | 0.08 | 2.17 | 9.81 | 0.21 |
| Stage 6 | 0.43 | 76.79 | 0.33 | 0.58 | 2.04 | 0.01 | 0.45 | 25.71 | 0.12 | 0.55 | 9.79 | 0.05 |
| Stage 7 | 5.17 | 164.61 | 8.51 | 0.25 | 6.73 | 0.02 | 0.19 | 42.64 | 0.08 | 0.20 | 14.13 | 0.03 |
| Stage 8 (MOC)* | 0.38 | 43.01 | 0.17 | 0.14 | 8.35 | 0.01 | 0.17 | 19.59 | 0.03 | 0.13 | 60.29 | 0.08 |
| MB(%) | 82.17 | 27.08 | 22.25 | 66.30 | 2.64 | 1.75 | 70.16 | 0.95 | 0.67 | 68.11 | 4.36 | 2.97 |
| ED(mg) | 32.87 | 27.08 | 8.90 | 26.51 | 2.64 | 0.70 | 28.04 | 0.95 | 0.27 | 27.17 | 4.36 | 1.19 |
| ISM(mg) | 23.28 | 36.12 | 8.41 | 20.38 | 2.56 | 0.52 | 19.79 | 2.99 | 0.59 | 20.97 | 3.20 | 0.67 |
| MMAD (μm) | 3.05 | 3.55 | 0.11 | 2.70 | 2.08 | 0.06 | 3.31 | 8.20 | 0.27 | 3.25 | 4.09 | 0.13 |
| GSD | 1.97 | 4.81 | 0.09 | 1.89 | 1.22 | 0.02 | 1.98 | 0.96 | 0.02 | 1.79 | 1.45 | 0.03 |
| FPM(mg) | 13.07 | 5.36 | 0.70 | 15.80 | 1.33 | 0.21 | 14.07 | 3.27 | 0.46 | 14.98 | 0.66 | 0.10 |
| FPF(%) | 32.67 | 5.36 | 1.75 | 39.51 | 1.33 | 0.52 | 35.21 | 3.27 | 1.15 | 37.55 | 0.66 | 0.25 |

*MOC: micro-orifice collector

TABLE 5D

APSD of ASA/MgST dry powder composition with 0.5%, 1.0%, 5.0%, and 10.0% w/w MgST

| | MgST % | | | | | | | | | | | |
|---|---|---|---|---|---|---|---|---|---|---|---|---|
| | 0.5 | | | 1.0 | | | 5.0 | | | 10.0 | | |
| NGI Stage | Ave | RSD | SD | Ave | RSD | SD | Ave | RSD | SD | Ave | RSD | SD |
| Mouthpiece | 0.42 | 25.55 | 0.11 | 0.39 | 6.96 | 0.03 | 0.18 | 5.27 | 0.01 | 0.53 | 5.33 | 0.03 |
| Throat | 4.24 | 17.67 | 0.75 | 5.61 | 5.48 | 0.31 | 6.10 | 20.38 | 1.24 | 3.84 | 1.44 | 0.06 |
| Stage 1 | 2.10 | 9.87 | 0.21 | 2.70 | 1.65 | 0.04 | 10.22 | 7.69 | 0.79 | 1.63 | 8.80 | 0.14 |
| Stage 2 | 5.45 | 1.26 | 0.07 | 5.35 | 0.97 | 0.05 | 2.44 | 5.44 | 0.13 | 2.44 | 3.14 | 0.14 |
| Stage 3 | 6.71 | 2.21 | 0.15 | 5.66 | 3.07 | 0.17 | 2.38 | 6.20 | 0.15 | 6.45 | 3.97 | 0.26 |
| Stage 4 | 5.24 | 0.44 | 0.02 | 4.71 | 6.40 | 0.30 | 1.35 | 4.38 | 0.06 | 5.21 | 3.13 | 0.16 |
| Stage 5 | 2.55 | 5.90 | 0.15 | 2.12 | 9.07 | 0.19 | 0.75 | 11.08 | 0.08 | 2.70 | 1.56 | 0.04 |
| Stage 6 | 0.74 | 18.64 | 0.14 | 0.64 | 6.95 | 0.04 | 0.35 | 7.97 | 0.03 | 0.95 | 3.11 | 0.03 |
| Stage 7 | 0.21 | 18.37 | 0.04 | 0.14 | 7.23 | 0.01 | 0.20 | 6.13 | 0.01 | 0.28 | 16.66 | 0.05 |
| Stage 8 (MOC) | 0.14 | 24.92 | 0.03 | 0.10 | 3.95 | 0.00 | 0.16 | 15.67 | 0.03 | 0.18 | 6.86 | 0.01 |
| MB(%) | 69.85 | 1.94 | 1.35 | 69.27 | 1.57 | 1.08 | 63.49 | 2.90 | 1.84 | 77.07 | 1.49 | 1.15 |
| ED(mg) | 27.80 | 1.94 | 0.54 | 27.43 | 1.57 | 0.43 | 24.13 | 2.90 | 0.70 | 27.74 | 1.49 | 0.41 |
| ISM(mg) | 21.04 | 2.67 | 0.56 | 18.73 | 3.89 | 0.73 | 7.63 | 3.51 | 0.27 | 21.74 | 1.77 | 0.38 |
| MMAD (μm) | 2.75 | 1.61 | 0.04 | 2.90 | 1.71 | 0.05 | 8.54 | 14.67 | 1.25 | 3.08 | 9.21 | 0.28 |
| GSD | 1.88 | 1.82 | 0.03 | 2.00 | 0.35 | 0.01 | 3.88 | 7.03 | 0.27 | 1.82 | 0.63 | 0.01 |
| FPM (mg) | 15.59 | 3.19 | 0.50 | 13.40 | 4.97 | 0.67 | 5.12 | 2.51 | 0.13 | 15.71 | 2.57 | 0.40 |
| FPF (%) | 39.17 | 3.19 | 1.25 | 33.83 | 4.97 | 1.68 | 13.48 | 2.51 | 0.34 | 43.63 | 2.57 | 1.12 |

As shown by the fine particle fraction (FPM), fine particle dose (FPD) and mass median aerodynamic diameter (MMAD) of the various ASA/MgST dry powder compositions (FIGS. 4A-4D; Tables 5A-5D), the ASA/MgST dry powder compositions with 0.05% and 0.5% w/w MgST were preferred for the inhaled delivery of ASA. Both dry powder compositions had MMAD of approximately 2.7 μm, which is largely due to higher amount of material deposited on stage 4 of the impactor. The particles in the stage 4 fraction were between 1.4-1.6 μm, which are likely to deposit in the peripheral airway. The ASA/MgST dry powder compositions with 0.05% and 0.5% w/w MgST had much lower throat deposition than the other formulations. Thus, these formulation systems had excellent aerosolization efficiency and were likely to have low mouth-throat deposition.

Particle size distribution of ASA/MgST dry powder composition with 0.5%, 1%, 5%, and 10% w/w MgST, spray-dried Aspirin 85%/Leucine 15% Formulation (036 or 36)>Aspirin 95%/Leucine 5% Formulation (046 or 46), and micronized ASA were measured by Spraytec using low resistance device, at 90 L/min flow rate with 2.7 second actuation time with a ste0up of device/mouthpiece/USP/throat/IC/DUSA, and 5 tests for each composition (Table 5E).

addition of fine lactose particles or coating the coarse lactose particles with low energy force control agents (FCA) such as magnesium stearate. In high-payload DPI systems, the delivered dose of drug substance is a few miligrams and are formulated as carrier free systems. In these systems, the excipient content is low and major governing force that influences aerosolization efficiency are the cohesive (drug-drug interactions).

Co-micronisation of the ASA with magnesium stearate (MgST) was used in formulating a high-payload DPI formulation of acetylsalicylic acid (ASA), as described in Example 1. Aerosolization performance of this formulation is better than that of micronized ASA and spray-dried

TABLE 5E

Particle Size Distribution of ASA/MgST dry powder composition with 0.5%, 1%, 5%, and 10% w/w MgST measured by Spraytec.
Spraytec Data

| Batch Number | Dv(10)/μm | Dv(50)/μm | Dv(90)/μm | % V < 5 μm/% | % V < 10 μm/% | Trans [%] |
|---|---|---|---|---|---|---|
| O36 | 3.52 (0.7) | 12.28 (2.75) | 32.86 (10.4) | 17.12 (4.32) | 41.66 (9.23) | 46.53 (3.65) |
| O46 | 2.21 (0.13) | 6.94 (1.08) | 16.95 (2.78) | 35.07 (6.93) | 69.09 (8.19) | 50.62 (4.74) |
| Micronized ASA | 1.9 (0.08) | 4.62 (0.24) | 10.32 (0.65) | 54.7 (3.15) | 88.99 (2.05) | 67.92 (1.89) |
| 0.5% MgSt Micronized | 1.12 (0.26) | 2.67 (0.49) | 5.8 (1.71) | 86.43 (10.58) | 98.59 (1.75) | 52.64 (4.71) |
| 0.5% MgSt Micronized (Conditioned) | 1.27 (0.1) | 3.04 (0.15) | 6.65 (0.32) | 78.37 (2.26) | 98.33 (0.61) | 42.23 (3.99) |
| 1% MgSt Micronized | 1.04 (0.43) | 3.75 (0.39) | 9.2 (1.55) | 65.34 (6.3) | 92.19 (4.18) | 38.85 (4.57) |
| 5% MgSt Micronized | 1.89 (0.29) | 6.19 (1.55) | 21.79 (6.05) | 42.69 (10.65) | 69.79 (10.01) | 72.8 (8.09) |
| 10% MgSt Micronized | 0.45 (0.05) | 5.67 (0.76) | 15.55 (3.05) | 45.1 (5.08) | 75.66 (5.95) | 25.08 (2.14) |

Comparison of NGI and Spraytec data is shown in Table 5F:

TABLE 5F

NGI v. Spraytec

| | NGI | | Spraytec Data | |
|---|---|---|---|---|
| Batch Number | MMAD/μm | FPF/% | DV(50)/μm | % V < 5 μm/% |
| O36 | 5.14 | 36.35 | 12.28 (2.75) | 17.12 (4.32) |
| O46 | 4.37 | 44.86 | 6.94 (1.08) | 35.07 (6.93) |
| Micronized ASA | 4.86 | 20.71 | 4.62 (0.24) | 54.7 (3.15) |
| 0.5% MgSt Micronized | 2.64 | 62.87 | 2.67 (0.49) | 84.43 (10.58) |
| 0.5% MgSt Micronized (Conditioned) | 2.74 | 57.09 | 3.04 (0.15) | 78.37 (2.26) |
| 1% MgSt Micronized | 3.04 | 57.97 | 3.75 (0.39) | 65.34 (6.3) |
| 5% MgSt Micronized | 8.92 | 21.16 | 6.19 (1.55) | 42.69 (10.65) |
| 10% MgSt Micronized | 3.02 | 57.73 | 5.67 (0.76) | 45.1 (5.08) |

Example 6: Cohesion Characterizations of ASA/MgST Dry Powder Composition

The formulation performance of all DPI systems is controlled by the cohesive/adhesive surface interfacial properties of the particles. Since, the particles present in DPI systems are below 10 the forces that govern their cohesive/adhesive properties are van der Waals, electrostatic and capillary forces. In order to generate an aerosol from DPI systems the devices must help to overcome the cohesive/adhesive forces. Hence, the properties of the powder must be tailored to enable the device to generate an aerosol on the patient's inhalation.

Figure 5:
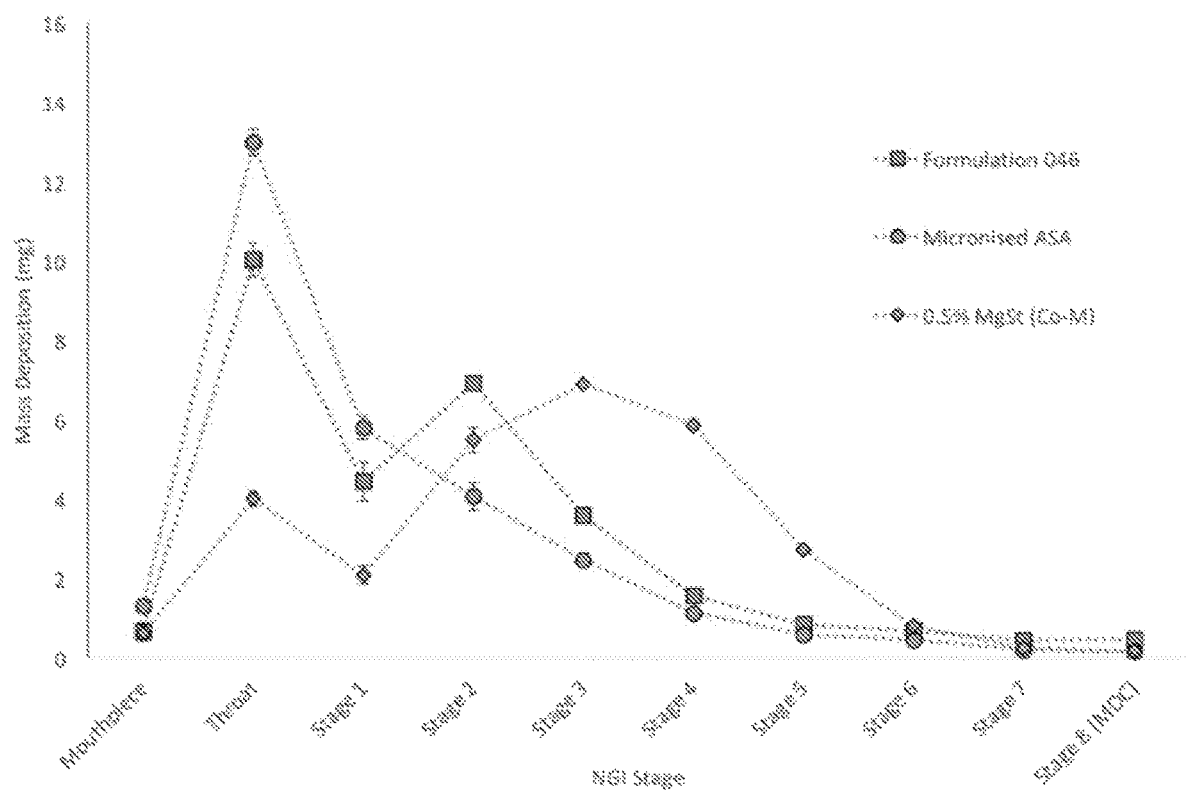
FIG. 5: APSD performance of examples of spray-dried ASA/Leucine (Formulation 046), micronized ASA and co-micronized ASA with 0.5% w/w MgST (Co-M).

In carrier-based DPI formulations that utilize coarse lactose carrier particles, these Forces are modulated through the ASA/leucine (FIG. 5). The ASA/MgST dry powder compositions showed lower cohesive force and enhanced aerosolization efficiency.

Figure 6:
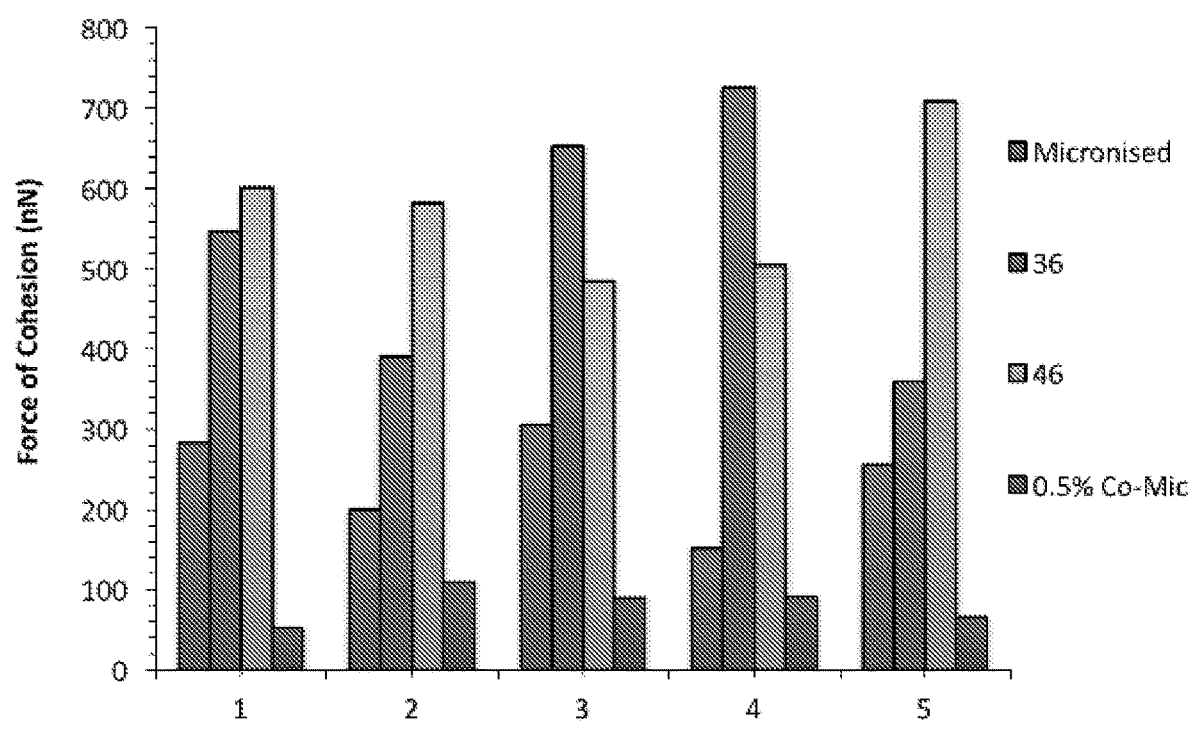
FIG. 6: Force of cohesion measurements of 5 different probes made from examples of spray-dried ASA/Leucine (Formulation 36 and 46), micronized ASA (micronized) and co-micronized ASA with 0.5% w/w MgST (0% Co-Mic).

Colloid-probe atomic force microscopy studies (AFM) was used to measure the cohesive surface interfacial forces (FIG. 6). Five individual particles from each of powder formulation was attached to tipless cantilevers. These were designated as drug probes, which were then interacted with a smooth surface of crystalline aspirin. In this way, it was possible to measure the force of cohesion of the particles of the different formulations (FIG. 6), which followed the following rank order:

Aspirin 85%/Leucine 15% Formulation (36)>Aspirin 95%/Leucine 5% Formulation (46)>Micronised ASA>ASA co-micronised with 0.5% magnesium stearate.

Powder permeability tests using a FT4 Powder Rheometer (Freeman Technologies, Gloucester, UK) were performed on various ASA formulations as described supra.

Powder permeability measurements of powder systems investigate the relationship between the effect of applied stress on the cohesivity of powder. The test was performed by applying different normal stresses to the powder, whilst trying to maintain a fixed flow rate of air through the powder. The measured pressure drop across the powder was therefore a measurement of the materials cohesivity. The pressure drop across the powder bed increases as more normal stress is applied to the powder, which is to be expected since the application of normal stress reduces the void spaces between particles, therefore, reducing the channels for the air to tunnel through the powder bed. Hence, powders with high cohesivity, which have lower bulk density, will generate higher pressure drops.

Figure 7:
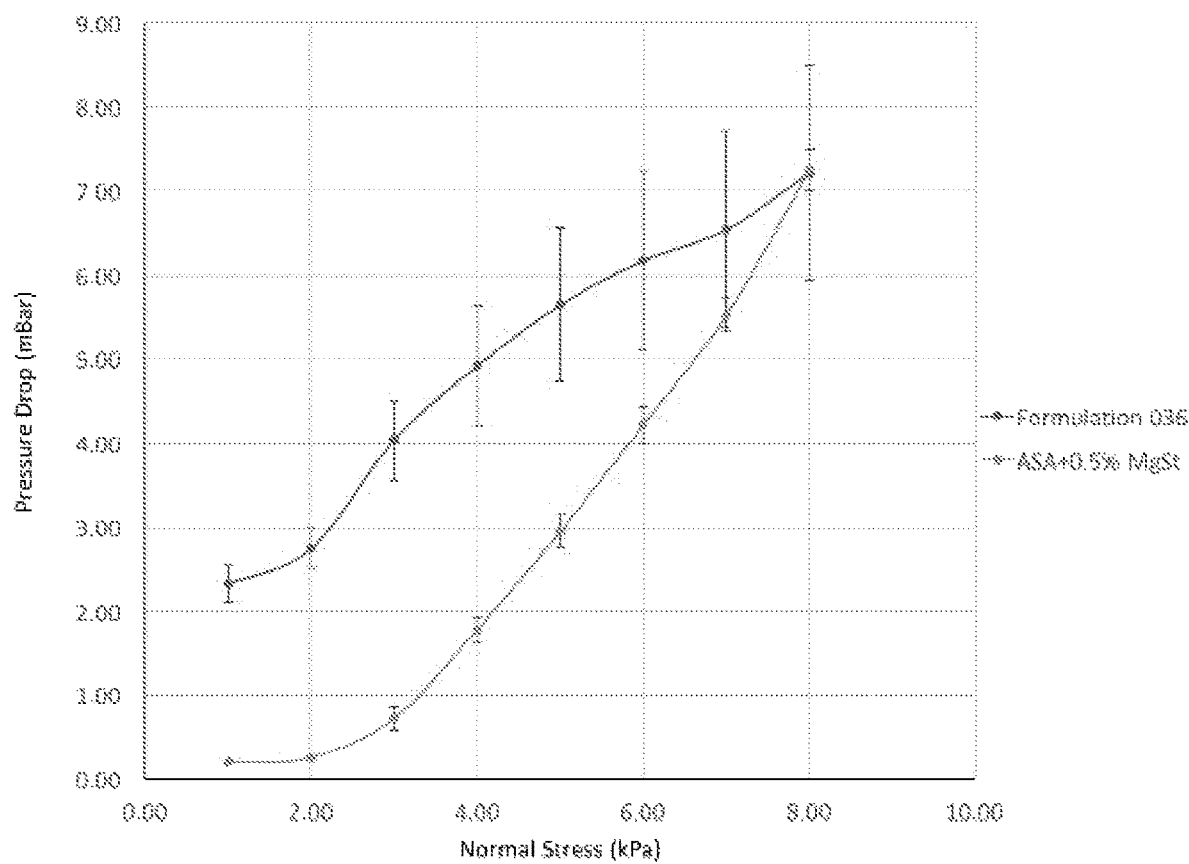
FIG. 7: Powder permeability measurements of formulation 036 and co-micronized formulation of ASA/MgST.

The pressure drop versus applied normal stress profile of formulation 036 and co-micronized ASA/MgST formulation is shown in FIG. 7. These data show that between applied normal stresses of 0.5-6.0 kPa, the pressure drop across the co-micronized ASA/MgST formulation were significantly lower than the 036 formulation. These data suggest that the cohesivity of the MgST formulation was significantly lower than the 036 formulation.

Based on both cohesion measurements, the introduction of 0.5% w/w MgST to ASA assisted to reduce the cohesivity of the formulation system, which would help to increase aerosolization efficiency as shown in FIG. 5.

Example 7: Pharmacokinetic Studies of ASA/MgST Dry Powder Composition

The pharmacokinetic profile of an ASA/MgST dry powder composition following a single inhalation administration to a dog was determined and compared to a commercially available acetylsalicylic acid tablet (Aspirin®) following a single oral administration to the same dog.

The ASA/MgST dry powder composition was administered to 3 dogs once by inhalation (Day 1) for 10 minutes and a commercially available acetylsalicylic acid tablet (Aspirin®) was administered to the same 3 dogs after a 7-day washout period (on Day 8) as follows:

A series of 10 blood samples (approximately 0.75 mL each) were collected from each dog on each of Days 1 and 8 of the treatment period as follows:

On Day 1: at pre-dose, Immediately Post 10-min Exposure (IPE±2 minutes), 20, 30 and 40 min, 1, 2, 4, 6, and 24 hours from the beginning of exposure, On Day 8: at pre-dose, 10, 20, 30, 40 min, 1, 2, 4, 6 and 24 hours post-dose.

The pharmacokinetic (PK) profiles of the ASA/MgST dry powder composition comprising 0.5% MgST in Beagle dogs were determined from ASA and salicylic acid (SA) plasma concentration data sets obtained on Days 1 and 8 following a single inhalation administration and a commercially available acetylsalicylic acid tablet (Aspirin®) following a single oral administration. ASA and SA plasma concentration were modeled using the Phoenix WinNonlin 6.4 software.

ASA plasma concentration maximum mean concentration levels ($C_{max}$) were reached within 0.2 and 0.3 hours post administration for inhalation and oral exposure, respectively. Two out of the three dogs showed a longer $T_{max}$ after oral administration (0.3 hr) than after inhalation administrations (0.2 hr), while one dog showed similar $T_{max}$ after oral and inhalation administrations (0.2 hr). After $T_{max}$, the plasma concentrations declined rapidly with a mean estimated $t_{1/2}$ value of 0.23 and 0.21 hours for the inhalation and oral route of exposure, respectively.

The SA plasma concentration maximum mean concentration levels ($C_{max}$) were reached within 0.4 and 1.7 hours post administration for inhalation and oral exposure, respectively. Subjects has a significantly shorter $T_{max}$ after inhalation administration (0.4 hr by average) than after oral administration (1.7 hr by average). After $T_{max}$, the plasma concentrations declined at a mean estimated $t_{1/2}$ value of 1.72 and 3.86 hours for the inhalation and oral route of exposure, respectively The ASA exposure by inhalation was higher than the oral exposure as evidenced by the ratios, which ranged from 2.7 to 6.7 for the AUC's and $C_{max}$, respectively, while no $t_{1/2}$ difference could be observed between the two administration routes.

No major administration-related difference could be observed in the SA exposure as evidenced by the ratios, which ranged from 0.7 to 1.5 for the AUC's and $C_{max}$ pharmacokinetic parameters, respectively.

TABLE 6A

Administration regime

| Group No. | Study Phase | Target Lung Dose Level of ASA[a] (mg/kg/day) | Target Inhaled Dose Level of ASA (mg/kg/day) | Target Aerosol Concentration of ASA (mg/L) | Target Oral Dose Level of Aspirin (mg per each dog) | Number of Male Dogs |
|---|---|---|---|---|---|---|
| 1 | Inhalation | 1.25 | 5 | 1.556 | NA | 3 |
|   | Oral | NA | NA | NA | 81 |   |

ASA = Acetylsalicylic acid

[a]Target lung dose levels are calculated assuming 25% lung deposition in dogs and based on an estimated body weight of 10 kg.

All dogs following last blood collection were released to the ITR spare colony on Day 9.

TABLE 6B

Individual and Group Mean Pharmacokinetic Parameters of Acetylsalicylic Acid (ASA) Based on Administration Route in Male Dogs

| Day | Group Designation | subject ID | $AUC_{0\text{-}Tlast}$ hr*ng/mL | $AUC_{INF}$ hr*ng/mL | AUC Extrap % | $T_{max}$ % | $C_{max}$ hr | $t_{1/2}$ ng/mL | $R^2$ adjusted |
|---|---|---|---|---|---|---|---|---|---|
| 1 | Inhalation 1.25 mg/kg | 1001A | 915.40 | 918.07 | 0.3 | 0.2 | 4351.20 | 0.29 | 1.0 |
|   |   | 1002A | 733.23 | 734.83 | 0.2 | 0.2 | 3305.26 | 0.26 | 1.0 |
|   |   | 1003A | 436.45 | 440.60 | 0.9 | 0.2 | 1723.52 | 0.14 | 1.0 |
|   |   | Mean  | 695.02 | 697.83 | 0.5 | 0.2 | 3126.66 | 0.23 | 1.0 |
|   |   | SE    | 139.574 | 139.071 | 0.23 | 0 | 763.784 | 0.046 | 0.01 |
|   |   | N     | 3 | 3 | 3 | 3 | 3 | 3 | 3 |
| 8 | Oral, 81 mg/animal | 1001A | 1443.73 | 1447.40 | 0.3 | 0.2 | 2622.05 | 0.22 | 1.0 |
|   |   | 1002A | 1666.33 | 1672.80 | 0.4 | 0.3 | 2708.90 | 0.23 | 0.9 |
|   |   | 1003A | 2418.57 | 2420.61 | 0.1 | 0.3 | 4691.21 | 0.18 | 1.0 |
|   |   | Mean  | 1842.88 | 1846.94 | 0.2 | 0.3 | 3340.72 | 0.21 | 1.0 |
|   |   | SE    | 294.932 | 294.126 | 0.087 | 0 | 675.709 | 0.017 | 0.03 |
|   |   | N     | 3 | 3 | 3 | 3 | 3 | 3 | 3 |

TABLE 6C

Individual and Group Mean Pharmacokinetic Parameters of Salicylic acid (SA) Based on Administration Route in Male Dogs

| Day | Group Designation | subject ID | $AUC_{0\text{-}Tlast}$ hr*ng/mL | $AUC_{INF}$ hr*ng/mL | AUC Extrap % | $T_{max}$ hr | $C_{max}$ ng/mL | $t_{1/2}$ hr | $R^2$ adjusted |
|---|---|---|---|---|---|---|---|---|---|
| 1 | Inhalation 1.25 mg/kg | 1001A | 12787.21 | 15837.84 | 19.3 | 0.5 | 4461.62 | 1.65 | 0.9 |
|   |   | 1002A | 11306.64 | 14611.84 | 22.6 | 0.2 | 3755.60 | 1.84 | 0.9 |
|   |   | 1003A | 13592.53 | 15044.86 | 9.7 | 0.5 | 4233.62 | 1.66 | 1.0 |
|   |   | Mean  | 12562.13 | 15164.85 | 17.2 | 0.4 | 4150.28 | 1.72 | 0.9 |
|   |   | SE    | 669.407 | 358.966 | 3.885 | 0 | 208.027 | 0.061 | 0.04 |
|   |   | N     | 3 | 3 | 3 | 3 | 3 | 3 | 3 |
| 8 | Oral, 81 mg/animal | 1001A | 73922.27 | NC | NC | 2.0 | 18823.22 | NC | NC |
|   |   | 1002A | 72565.10 | NC | NC | 2.0 | 17822.20 | NC | NC |
|   |   | 1003A | 102348.74 | 164959.08 | 38.0 | 1.0 | 23473.83 | 3.86 | 1.0 |
|   |   | Mean  | 82945.37 | 164959.08* | 38.0 | 1.7 | 20039.75 | 3.86* | 1.0 |
|   |   | SE    | 9709.592 | 0 | 0 | 0 | 1741.187 | 0 | 0.00 |
|   |   | N     | 3 | 1 | 1 | 3 | 3 | 1 | 1 |

*The $AUC_{INF}$ and $t_{1/2}$ should be interpreted with caution as values were obtained from only 1 animal.

TABLE 6D

Group Mean Pharmacokinetic AUC's and $C_{max}$ Parameters of Acetylsalicylic Acid (ASA) and Salicylic acid (SA) Normalized by Dose Concentration Based on Administration Route in Male Dogs

| | | | Normalized by Dose concentration | | |
|---|---|---|---|---|---|
| Analyte | Administration route | Dose concentration (mg/kg) | $AUC_{0\text{-}Tlast}$ (hr*ng/mL) | $AUC_{INF}$ (hr*ng/mL) | $C_{max}$ (ng/mL) |
| ASA | Inhalation | 1.25 | 556.02 | 558.27 | 2501.33 |
|     | Oral       | 9    | 204.76 | 205.22 | 371.19 |
| SA  | Inhalation | 1.25 | 9969.94 | 12035.59 | 3320.22 |
|     | Oral       | 9    | 9216.15 | 18328.79 | 2226.63 |

TABLE 6E

Exposure Route Ratios (Inhalation vs Oral) of Mean of Acetylsalicylic Acid (ASA) and Salicylic acid (SA) AUC's and $C_{max}$ in Dog Plasma

| | | Normalized ratio | | | | |
|---|---|---|---|---|---|---|
| Group Designation | Analyte | $AUC_{0\text{-}tlast}$ ratio | $AUC_{INF}$ ratio | $C_{max}$ ratio | $T_{max}$ ratio | $t_{1/2}$ ratio |
| Inhalation/Oral administration | ASA | 2.7 | 2.7 | 6.7 | 0.6 | 1.1 |
|  | SA | 1.1 | 0.7* | 1.5 | 0.2 | 0.4* |

*Ratio for this group should be interpreted with caution as values were obtained from only 1 animal.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

It is to be understood that, while the subject technology has been described in conjunction with the detailed description, thereof, the foregoing description is intended to illustrate and not limit the scope of the subject technology. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

The invention claimed is:

1. A drug delivery system for administering a formulation to a person in need thereof via the respiratory tract, said system comprising:
   (a) a dry powder composition comprising dry particles comprising acetylsalicylic acid (ASA), or a pharmaceutically acceptable salt thereof, co-micronized with magnesium stearate, wherein the magnesium stearate is in an amount of about 0.05% (w/w) to about 0.5% (w/w) of the dry powder composition, and ASA stability maintains about 95% or above after exposure to a condition selected from the group consisting of 15-20° C./35-45% relative humidity (RH), 20° C./40% RH, 30° C./60% RH, 40° C./75% RH, and 50° C./75% RH, for two weeks, four weeks, 30 days, a month, six weeks, eight weeks, or 12 months; and
   (b) a dry powder inhaler.

2. The drug delivery system of claim 1, wherein the dry powder composition further comprises clopidogrel.

3. The drug delivery system of claim 1, wherein the magnesium stearate is in an amount ranging from about 0.04% (w/w) to about 0.06% (w/w), or from about 0.4% (w/w) to about 0.6% (w/w), of the dry powder composition, wherein acetylsalicylic acid, or a pharmaceutically acceptable salt thereof, is in an amount of about 50% (w/w) or more of the thy powder composition.

4. The drug delivery system of claim 1, substantially free of carrier particles.

5. The drug delivery system of claim 1, wherein the dry particles have a median mass aerodynamic diameter (MMAD) within a range of about 1 µm to about 5 µm.

6. The drug delivery system of claim 5, wherein the dry particles have a MMAD within a range of about 2 µm to about 3 µm.

7. The drug delivery system of claim 1, wherein acetylsalicylic acid, or a pharmaceutically acceptable salt thereof, is in an amount of about 80% (w/w) or more of the dry powder composition.

8. The drug delivery system of claim 1, wherein the aerodynamic particle size distribution (APSD) of the dry powder composition as measured by mass deposition at stage 1 to stage 8 of a Next Generation Impactor varies by less than about 10% after the dry powder composition has been stored at 50° C./75% relative humidity for about 30 days when compared with the APSD at time, t, equals zero.

9. The drug delivery system of claim 5, wherein the MMAD of the dry particles varies by less than about 10% after the dry powder composition have been stored at 50° C./75% relative humidity for about 5 days when compared with the MMAD at time, t, equals zero.

10. The drug delivery system of claim 5, wherein the dry particles have an MMAD size distribution with a DV90 less than about 6 µm, a DV50 less than about 3 µm, and a DV10 less than about 1 µm.

11. The drug delivery system of claim 10, wherein the DV90, DV50 and/or DV10 vary less than about 10% after the composition is stored at 50° 075% relative humidity for about 15 days.

12. The drug delivery system of claim 1, wherein the dry powder inhaler comprises:
   a housing defining a chamber having one or more air inlets, and one or more air outlets;
   the chamber sized to receive a capsule which contains the dry powder composition;
   a puncturing mechanism in the housing for creating one or more openings in the capsule;
   an optional shield covering at least two but not all of the air inlets, wherein the optional shield comprises one or two or more covering portions, each covering portion covering at least one inlet, whereby the optional shield prevents blockage of at least two air inlets by a user grasping the apparatus; and
   an end section associated with the housing, the end section sized and shaped to be received in a user's mouth or nose so that the user may inhale through the end section to aerosolize the dry powder composition and to inhale aerosolized dry powder composition that has exited the capsule.

13. A method of treating inflammation or treating or reducing a risk of a thrombotic event, comprising administering to a subject in need thereof via the respiratory tract a dry powder composition comprising dry particles comprising acetylsalicylic acid (ASA), or a pharmaceutically acceptable salt thereof, co-micronized with magnesium stearate, wherein the magnesium stearate is in an amount of about 0.05% (w/w) to about 0.5% (w/w) of the dry powder composition, and ASA stability maintains about 95% or above after exposure to a condition selected from the group consisting of 15-20° C./35-45% RH, 20° C./40% RH, 30° C./60% RH, 40° C./75% RH, and 50° C./75% RH, for two weeks, four weeks, 30 days, a month, six weeks, eight weeks, or 12 months,
   wherein said dry powder composition is administered using a drug delivery system of claim 1.

14. The method of claim 13, wherein the thrombotic event comprises a myocardial infraction.

15. The method of claim 13, wherein the thrombotic event comprises a transient ischemic event.

16. The method of claim 13, wherein the thrombotic event comprises a stroke.

17. The method of claim 13, wherein the thrombotic event is treated within about 5 minutes of onset of the thrombotic event.

* * * * *